United States Patent
Kim et al.

(10) Patent No.: US 9,669,073 B2
(45) Date of Patent: Jun. 6, 2017

(54) USE OF PROINSULIN FOR IMMUNE SYSTEM MODULATION

(71) Applicant: Konkuk University Industrial Cooperation Corporation, Seoul (KR)

(72) Inventors: Soohyun Kim, Seoul (KR); Si-Young Lee, Seoul (KR); Eunsom Kim, Seoul (KR); Seunghyun Jo, Seoul (KR); Youngmin Lee, Busan (KR); Tania Azam, Aurora, CO (US); Suyoung Bae, Seoul (KR); Areum Kwak, Icheon-Si (KR); Jaewoo Hong, Seoul (KR); Hyun Jhung Jhun, Seoul (KR); Jong Ho Lee, Seoul (KR); Jungmin Lee, Seongnam-Si (KR); Sulah Youn, Daejeon (KR); Busun Kim, Aurora, CO (US)

(73) Assignee: Konkuk University Industrial Cooperation Corporation, Seoul (KR)

(*) Notice: Subject to any disclaimer, the term of this patent is extended or adjusted under 35 U.S.C. 154(b) by 0 days.

(21) Appl. No.: 14/674,590

(22) Filed: Mar. 31, 2015

(65) Prior Publication Data

US 2016/0184402 A1 Jun. 30, 2016

(30) Foreign Application Priority Data

Dec. 30, 2014 (KR) .......................... 10-2014-0194162

(51) Int. Cl.
*A61K 38/28* (2006.01)
*C07K 16/26* (2006.01)

(52) U.S. Cl.
CPC .............. *A61K 38/28* (2013.01); *C07K 16/26* (2013.01)

(58) Field of Classification Search
CPC ................................ A61K 38/28; C07K 16/26
See application file for complete search history.

(56) References Cited

U.S. PATENT DOCUMENTS 8,841,417 B2 9/2014 Wu et al.

OTHER PUBLICATIONS

Nordquist et al., Vasc. Health and Risk Management, 4: 1283-1288, 2008.*
Csorba, T.R. and Lyon, A.W., "Abnormal proinsulin congeners as autoantigens that initiate the pathogenesis of Type 1 diabetes", Medical Hypotheses, 2005, vol. 64, pp. 186-191.

* cited by examiner

*Primary Examiner* — Gyan Chandra
(74) *Attorney, Agent, or Firm* — Drinker Biddle & Reath LLP

(57) ABSTRACT

The present disclosure relates to a composition for promoting immune activity including a protein selected from the group consisting of dimeric proinsulin, C-peptide partially deleted mutant of dimeric proinsulin, and C-peptide partially deleted mutant of monomeric proinsulin as an effective component and a composition for immunosuppression including C-peptide site of proinsulin as an effective component, and the dimeric proinsulin, the C-peptide partially deleted mutant of dimeric proinsulin, and the C-peptide partially deleted mutant of monomeric proinsulin can be applied as immune enhancers to diabetic patients.

6 Claims, 59 Drawing Sheets

| INS-d/C1 | INS-d/C2 |
|---|---|
| IL-1α VCLAGGP<br>∶ ∶ ∶ ∶ ∶<br>INS  VELGGGP | IL-1α  VCLAGGPPSITDFQIL<br>∶ ∶ ∶ ∶ ∶ ∶   ∶ ∶ ∶ ∶<br>INS   VELGGGP-GAGSLQPL |
| 71.4% identity in 7<br>amino acid overlap | 43.8% identity in 16<br>amino acid overlap |

FIG. 12A

Pro Insulin (83aa)
FVNQHLCGSHLVEALYLVCGERGFFYTPKTRREAEDLQVGQVELGGGPGAGSLQPLALEGSLQKRGIVEQCCTSICSLYQLENYCN Pro Insulin (74aa)
FVNQHLCGSHLVEALYLVCGERGFFYTPKTRREAEDLQVGQVELGGGPGAGSLQPLALEGSLQKRGIVEQCCTSICSLYQLENYCN

SEQUENCE LISTING

```
<160> NUMBER OF SEQ ID NOS: 17

<210> SEQ ID NO 1
<211> LENGTH: 86
<212> TYPE: PRT
<213> ORGANISM: Homo sapiens

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
                20                  25                  30

Glu Ala Glu Asp Leu Gln Val Gly Gln Val Glu Leu Gly Gly Gly Pro
            35                  40                  45

Gly Ala Gly Ser Leu Gln Pro Leu Ala Leu Glu Gly Ser Leu Gln Lys
        50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 2
```

<211> LENGTH: 79
<212> TYPE: PRT
<213> ORGANISM: Artificial Sequence
<220> FEATURE:
<223> OTHER INFORMATION: pINS-d/C1

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Gly Ala Gly Ser Leu Gln Pro
        35                  40                  45

Leu Ala Leu Glu Gly Ser Leu Gln Lys Arg Gly Ile Val Glu Gln Cys
    50                  55                  60

Cys Thr Ser Ile Cys Ser Leu Tyr Gln Leu Glu Asn Tyr Cys Asn
65                  70                  75

<210> SEQ ID NO 3
<211> LENGTH: 71
<212> TYPE: PRT
<213> ORGANISM: Artificial Sequence
<220> FEATURE:
<223> OTHER INFORMATION: pINS-d/C2

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Ala Leu Glu Gly Ser Leu Gln
        35                  40                  45

Lys Arg Gly Ile Val Glu Gln Cys Cys Thr Ser Ile Cys Ser Leu Tyr
    50                  55                  60

Gln Leu Glu Asn Tyr Cys Asn
65                  70

<210> SEQ ID NO 4
<211> LENGTH: 83
<212> TYPE: PRT
<213> ORGANISM: Artificial Sequence
<220> FEATURE:
<223> OTHER INFORMATION: Mutant of pro-insulin monomer

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Val Gly Gln Val Glu Leu Gly Gly Gly Pro Gly Ala Gly
        35                  40                  45

Ser Leu Gln Pro Leu Ala Leu Glu Gly Ser Leu Gln Lys Arg Gly Ile
    50                  55                  60

Val Glu Gln Cys Cys Thr Ser Ile Cys Ser Leu Tyr Gln Leu Glu Asn
65                  70                  75                  80

Tyr Cys Asn

<210> SEQ ID NO 5
<211> LENGTH: 74
<212> TYPE: PRT

<213> ORGANISM: Artificial Sequence
<220> FEATURE:
<223> OTHER INFORMATION: Mutant of pro-insulin monomer

<400> SEQUENCE: 5

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Gly Ser Leu Gln Pro Leu Ala Leu Glu Gly
        35                  40                  45

Ser Leu Gln Lys Arg Gly Ile Val Glu Gln Cys Cys Thr Ser Ile Cys
    50                  55                  60

Ser Leu Tyr Gln Leu Glu Asn Tyr Cys Asn
65                  70

<210> SEQ ID NO 6
<211> LENGTH: 7
<212> TYPE: PRT
<213> ORGANISM: Homo sapiens

<400> SEQUENCE: 6

Val Cys Leu Ala Gly Gly Pro
1               5

<210> SEQ ID NO 7
<211> LENGTH: 7
<212> TYPE: PRT
<213> ORGANISM: Homo sapiens

<400> SEQUENCE: 7

Val Glu Leu Gly Gly Gly Pro
1               5

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
ggtggggcag ggtgcaggca                                              20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
tgcctgcacc ctgccccacc                                              20

<210> SEQ ID NO 10
<211> LENGTH: 19
<212> TYPE: DNA
<213> ORGANISM: Artificial Sequence
<220> FEATURE:
<223> OTHER INFORMATION: primer

<400> SEQUENCE: 10
ggtggggcag gccctggag                                               19

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
cctccagggc ctgccccacc                                                    20

<210> SEQ ID NO 12
<211> LENGTH: 16
<212> TYPE: PRT
<213> ORGANISM: Homo sapiens

<400> SEQUENCE: 12

Val Cys Leu Ala Gly Gly Pro Pro Ser Ile Thr Asp Phe Gln Ile Leu
1               5                   10                  15

<210> SEQ ID NO 13
<211> LENGTH: 15
<212> TYPE: PRT
<213> ORGANISM: Homo sapiens

<400> SEQUENCE: 13

Val Glu Leu Gly Gly Gly Pro Gly Ala Gly Ser Leu Gln Pro Leu
1               5                   10                  15

<210> SEQ ID NO 14
<211> LENGTH: 159
<212> TYPE: PRT
<213> ORGANISM: Homo sapiens

<400> SEQUENCE: 14

Ser Ala Pro Phe Ser Phe Leu Ser Asn Val Lys Tyr Asn Phe Met Arg
1               5                   10                  15

Ile Ile Lys Tyr Glu Phe Ile Leu Asn Asp Ala Leu Asn Gln Ser Ile
                20                  25                  30

Ile Arg Ala Asn Asp Gln Tyr Leu Thr Ala Ala Ala Leu His Asn Leu
            35                  40                  45

Asp Glu Ala Val Lys Phe Asp Met Gly Ala Tyr Lys Ser Ser Lys Asp
        50                  55                  60

Asp Ala Lys Ile Thr Val Ile Leu Arg Ile Ser Lys Thr Gln Leu Tyr
65                  70                  75                  80

Val Thr Ala Gln Asp Glu Asp Gln Pro Val Leu Leu Lys Glu Met Pro
                85                  90                  95

Glu Ile Pro Lys Thr Ile Thr Gly Ser Glu Thr Asn Leu Leu Phe Phe
            100                 105                 110

Trp Glu Thr His Gly Thr Lys Asn Tyr Phe Thr Ser Val Ala His Pro
        115                 120                 125

Asn Leu Phe Ile Ala Thr Lys Gln Asp Tyr Trp Val Cys Leu Ala Gly
    130                 135                 140

Gly Pro Pro Ser Ile Thr Asp Phe Gln Ile Leu Glu Asn Gln Ala
145                 150                 155

<210> SEQ ID NO 15
<211> LENGTH: 33
<212> TYPE: PRT
<213> ORGANISM: Homo sapiens

<400> SEQUENCE: 15

-continued

```
Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln Lys
                20                  25                  30

Arg

<210> SEQ ID NO 16
<211> LENGTH: 83
<212> TYPE: PRT
<213> ORGANISM: Homo sapiens

<400> SEQUENCE: 16

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
                20                  25                  30

Glu Ala Glu Val Gly Gln Val Glu Leu Gly Gly Gly Pro Gly Ala Gly
            35                  40                  45

Ser Leu Gln Pro Leu Ala Leu Glu Gly Ser Leu Gln Lys Arg Gly Ile
        50                  55                  60

Val Glu Gln Cys Cys Thr Ser Ile Cys Ser Leu Tyr Gln Leu Glu Asn
65                  70                  75                  80

Tyr Cys Asn

<210> SEQ ID NO 17
<211> LENGTH: 74
<212> TYPE: PRT
<213> ORGANISM: Homo sapiens

<400> SEQUENCE: 17

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
                20                  25                  30

Glu Ala Glu Asp Leu Gln Gly Ser Leu Gln Pro Leu Ala Leu Glu Gly
            35                  40                  45

Ser Leu Gln Lys Arg Gly Ile Val Glu Gln Cys Cys Thr Ser Ile Cys
        50                  55                  60

Ser Leu Tyr Gln Leu Glu Asn Tyr Cys Asn
65                  70
```

USE OF PROINSULIN FOR IMMUNE SYSTEM MODULATION

CROSS-REFERENCE TO RELATED APPLICATIONS

This application is based on and claims priority from Korean Patent Application No. 10-2014-0194162, filed on Dec. 30, 2014, with the Korean Intellectual Property Office, the disclosure of which is incorporated herein in its entirety by reference.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_213143_0002. The size of the text file is 9 KB, and the text file was created on Jan. 12, 2017.

TECHNICAL FIELD

The present disclosure relates to a composition for promoting immune activity including a protein selected from the group consisting of dimeric proinsulin (hereinafter, referred to as "pINS-d"), C-peptide partially deleted mutant of dimeric proinsulin, and C-peptide partially deleted mutant of monomeric proinsulin as an effective component and a composition for immunosuppression including C-peptide site of proinsulin as an effective component.

BACKGROUND

Diabetes is a chronic systemic disease characterized by disorders in metabolism of insulin, carbohydrates, fats and proteins and in the structure and function of blood vessels. The primary symptom of acute diabetes is hyperglycemia, often accompanied by diabetes, the presence in urine of large amounts of glucose, and polyuria, the excretion of large volumes of urine. Additional symptoms including degeneration of the walls of blood vessels arise in chronic or long standing diabetes. Although many different human organs are affected by these vascular changes, the eyes and kidneys appear to be the most susceptible. As such, long-standing diabetes mellitus, even when treated with insulin, is a leading cause of blindness.

There are three recognized types of diabetes mellitus. Type I diabetes or insulin dependent diabetes mellitus (IDDM) is typically of juvenile onset; ketosis develops early in life with much more severe symptoms and has a near-certain prospect of later vascular involvement. Control of Type I diabetes is difficult and requires exogenous insulin administration. Type II diabetes or non-insulin dependent diabetes mellitus (NIDDM) is ketosis-resistant, generally develops later in life, is milder and has a more gradual onset. Gestational diabetes is related to type II diabetes and associated with an increased risk of later development of that disease. Type III diabetes is malnutrition-related diabetes.

Insulin (hereinafter, referred to as "INS") is a hormone secreted from particular β cells of the pancreas that regulates carbohydrate and fat metabolism in the body by triggering cells to absorb glucose. Human recombinant polypeptide A and B chains of mature INS or pINS were synthesized in *E. coli* as the result of cloning rat and human INS cDNA. To date, INS therapy has been solely focused on reducing blood glucose levels.

Therefore, it is necessary to provide an unknown immunological function of INS.

CITATION LIST

Patent Document 1: U.S. Pat. No. 8,841,417

SUMMARY

The present disclosure has been made in an effort to provide an unknown immunological function of INS.

An exemplary embodiment of the present disclosure provides a composition for promoting immune activity including a protein selected from the group consisting of dimeric proinsulin, C-peptide partially deleted mutant of dimeric proinsulin, and C-peptide partially deleted mutant of monomeric proinsulin.

In an exemplary embodiment of the present disclosure, preferably, the composition induces proinflammatory cytokines, and preferably, the proinflammatory cytokines are cytokines selected from the group consisting of interleukin (hereinafter, referred to as "IL")-6, IL-1β, IL-2, IL-10, IL-22, interferon γ, and TNFα, but are not limited thereto.

In an exemplary embodiment of the present disclosure, preferably, the proinsulin is formed of amino acids with SEQ ID No. 1, but all of the mutants that achieve the effect of the present disclosure by one or more substitutions, deletions, additions, and the like in the sequence are included in the scope of the present disclosure.

In another exemplary embodiment of the present disclosure, preferably, the C-peptide partially deleted mutant of dimeric proinsulin is a dimer of a peptide formed of amino acids with SEQ ID No. 2 or 3, but all of the mutants that achieve the effect of the present disclosure by one or more substitutions, deletions, additions, and the like in the sequence are included in the scope of the present disclosure.

In yet another exemplary embodiment of the present disclosure, preferably, the C-peptide partially deleted mutant of monomeric proinsulin is formed of amino acids with SEQ ID No. 4 or 5, but all of the mutants that achieve the effect of the present disclosure by one or more substitutions, deletions, additions, and the like in the sequence are included in the scope of the present disclosure.

In an example of the present disclosure, the composition prevents infection by improving immunity of a diabetic patient.

Another exemplary embodiment of the present disclosure provides a composition for immunosuppression including a C-peptide site of proinsulin.

In an exemplary embodiment of the present disclosure, preferably, the C-peptide site of the proinsulin is formed of amino acids with SEQ ID No. 6 or 7, but all of the mutants that achieve the effect of the present disclosure by one or more substitutions, deletions, additions, and the like in the sequence are included in the scope of the present disclosure.

In an example of the present disclosure, the composition prevents the onset of diabetes by immunosuppressing side effects caused by immune enhancement of dimeric proinsulin and thus suppressing early progression of diabetes.

Yet another exemplary embodiment of the present disclosure provides a composition for immunosuppression including an antibody against dimeric proinsulin.

In an example of the present disclosure, the antibody prevents the onset of diabetes by neutralizing apoptosis of pancreas β cells and thus suppressing early progression of diabetes.

Hereinafter, the present disclosure will be described.

The inventors of the present disclosure investigated the biological activity of recombinant INS. Dimeric proinsulin (hereinafter, referred to as "pINS-d") was a potent immune stimulus that induced proinflammatory cytokines IL-6, IL-1β, and TNFα, but monomeric pINS (hereinafter, referred to as "pINS-m") and mature commercial INS (comINS) were unable to induce an immune response. The activity of pINS-d in different cells corresponded with IL-1α activity, but not with IL-1β. Analysis of the pINS sequence revealed that the existence of an insulin/IL-1α motif in the C-terminus which does not exist in IL-1β or other members of the IL-1 cytokine family. Surprisingly, the insulin/IL-1α motif was independently recognized by monoclonal antibody-raised against IL-1α or pINS-d. The deletion of the insulin/IL-1α motif changed the biological activity of pINS-d and IL-1α, with activity varying across different cell types. Further in vivo and in vitro experiments with IL-1 receptor (IL-1R) 1 deficient mice demonstrated that pINS-d promotes immune responses through IL-1R1.

The inventors of the present disclosure expressed recombinant INS protein to investigate its activity. Two distinctive peaks of recombinant INS (not shown) were observed after the second step of HPLC purification where pINS-m and pINS-d were pooled in order to test biological activities. The results were repeated with various cell types, and this demonstrates that pINS-d possesses the immunological capability to induce proinflammatory cytokines. This data provides direct evidence for the first time that INS induces proinflammatory cytokines.

A careful analysis of the pINS sequence revealed an INS/IL-1α homology motif. The C1 motif of 7 amino acid residues in the C-peptide of pINS shares very high homology (71.4%) with IL-1α at the C-terminus (FIG. 5). Deletion of the motif changed the biological activities of pINS-d and IL-1α and suggests critical role of the motif in immunological activities (FIGS. 3 and 4). The data demonstrates that pINS-d/C1 and C2 as well as IL-1α/C1 and C2 mutant are able to enhance or reduce their activities depending on the cell type.

The cross-reactivity of the mAb raised an independent antigen that was able to recognize the motif in both pINS-d and IL-1α which corresponded to that the immunological functions of pINS-d is very similar to IL-1α. Their similarity was further validated by using Wish IL-1R1 stable clones to demonstrate that pINS-d uses IL-1 receptor 1 (hereinafter, referred to as "IL-1R1") as a receptor. The IL-1R1-reconstituted Wish cells lacking IL-1R1 had dramatically increased IL-6 production, which was reversed by IL-1 receptor antagonist (hereinafter, referred to as "IL-1Ra") (FIGS. 2e to 2h). In addition, IL-1R1 deficient mice had lower pINS-d-mediated proinflammatory cytokine production compared to production in wild type (hereinafter, referred to as "WT") mice in vitro and in vivo (FIG. 8).

It is supposed that the reason why an immune response is different between cells in the present disclosure may be that there is a difference in receptor expression because unlike IL-1β, IL-1α is limitedly inhibited in non-immune cells by IL-1Ra (IL-1 receptor antagonist).

The polypeptide described in the present disclosure may be used for preparing an immunogenic composition (for example, a vaccine composition) induces or enhances an immune response against an antigen included in the composition when administered to a subject (for example, a mammal). This response may include antibody formation (for example, by stimulation of B cells) or T cell-basic response (for example, cytolysis). These responses may be or may not be protective or neutral. A protective or neutral immune response is harmful to an infective organism (for example, from which the antigen is induced) serving as the antigen but beneficial to the subject (for example, by reducing or preventing infection). The protective or neutral antibody used in the present disclosure is reactive to a corresponding dimeric proinsulin (or its fragment) when tested to an animal and may suppress immune enhancement of corresponding pINS-d. An immunogenic composition that induces a protective or neutral immune response when administered to a host can be considered as a vaccine.

The composition includes an immunogenic polypeptide in an amount sufficient to induce an immune response when administered to the subject. An immunogenic composition used as a vaccine includes immunogenic polypeptide in an immunological effective amount and also includes any other component if necessary. The term "immunological effective amount" means that administration of that amount to a subject, either in a single dose or as part of a series, is effective for treatment or prevention.

In the composition formed of two, three or more immunogenic polypeptides, preferably, the polypeptide components are compatible and combined in appropriate ratios to avoid antigenic interference and optimize any possible synergies. For example, the amount of each component may be in a range of about 5 μg to about 500 μg per dose, 5 μg to about 100 μg per dose, or 25 μg to about 50 μg per dose, and preferably, the amount of each antigen component may be in a range of 5 or 6 μg to 50 μg per dose.

The compositions of the present disclosure may be administered by an appropriate administration route, for example, by percutaneous (for example, intramuscular, intravenous, intraperitoneal, or subcutaneous), transdermal, mucosal (for example, intranasal), or topical administration route in amounts and in regimens determined to be appropriate by those skilled in the art. For example, 1 to 250 μg or 10 to 100 μg of the composition may be administered. The composition may be administered 1, 2, 3, 4 or more times for the purposes of prophylaxis or therapy. In one example, the one or more administrations may occur as part of a "prime-boost" protocol. When multiple doses are administered, the doses can be separated from one another by, for example, one week, one month or several months.

The compositions (for example, vaccine compositions) of the present disclosure may be administered in the presence or absence of an adjuvant. Adjuvants generally are substances that can enhance the immunogenicity of antigens. Adjuvants may play a role in both acquired and innate immunity (for example, toll-like receptors) and may function in various ways, not all of which are understood.

Many substances (both natural and synthetic) have been exhibited to function as adjuvants. For example, adjuvants may include, but are not limited to, mineral salts, squalene mixtures, muramyl peptide, saponin derivatives, mycobacterium cell wall preparations, certain emulsions, monophosphoryl lipid A, mycolic acid derivatives, nonionic block copolymer surfactants, Quil A, cholera toxin B subunit, polyphosphazene and derivatives, immunostimulating complexes (ISCOMs), cytokine adjuvants, MF59 adjuvant, lipid adjuvants, mucosal adjuvants, certain bacterial exotoxins and other components, certain oligonucleotides, PLG, and the like. These adjuvants may be used in the compositions and methods described in the present disclosure.

The pharmaceutical formulations of the compositions of the present disclosure may also optionally include one or more excipients (for example, diluents, thickeners, buffers, preservatives, surfactants, adjuvants, detergents and/or immunostimulants) which are well known in the art. Suitable excipients will be compatible with the antigen and with the aluminum adjuvant as is known in the art. Examples of diluents include binder, disintegrants, or dispersants (for example, starch, cellulose derivatives, phenol, polyethylene glycol, propylene glycol, or glycerin). Pharmaceutical formulations may also include one or more active ingredients such as antimicrobial agents, antiinflammatory agents, and anesthetics. Examples of detergents include a Tween (polysorbate) such as Tween 80. Appropriate excipients for inclusion in the compositions of the present disclosure are well known in the art.

Hereinafter, the present disclosure will be described in detail.

A Dimeric Proinsulin (pINS-d) Induces Immune Cytokines.

The inventors of the present disclosure expressed recombinant INS to investigate its role in the immune response. Two distinct molecular sizes of monomeric proinsulin (pINS-m) and dimeric proinsulin (pINS-d) were observed by silver staining after the second step of purification using high-performance liquid chromatography (HPLC). The inventors of the present disclosure used each fraction to stimulate human umbilical vein endothelial cells (HUVEC). Prominent induction of interleukin-6 (IL-6) was observed where pINS-d fractions appeared (FIG. 8A). The pINS-m and pINS-d fractions were pooled as shown at the bottom of FIGS. 1A and 1B. The pINS-m, pINS-d, and a mature commercial INS (comINS) were used to stimulate various cell types. The results were consistent with the preliminary HUVEC assay (FIG. 8A). The pINS-d was highly effective in inducing IL-6, while the pINS-m and comINS were ineffective (FIGS. 1C to 1F). Because IL-6 production was most reliable across different cell types, inventors of the present disclosure chose to monitor IL-6 regulation by pINS-d (FIGS. 8 G to 8I).

This data suggests that only pINS-d has the ability to stimulate immunological activities, but the pINS-m and mature comINS were not able to stimulate immune, epithelial, and endothelial cells to produce IL-6 (FIG. 1). The pINS-d-mediated proinflammatory cytokine production in various cell types precisely overlapped with IL-1α activity, but not with IL-1β activity (FIGS. 8D to 8F). For example, although activity levels varied across different cell types, pINS-d and IL-1α were active in all types of cells used for the cytokine assays (FIGS. 8D to 8F). In contrast, IL-1β was not active in whole blood cell (WBC), polymorphonuclear (PMN), or THP-1 cells (FIGS. 8E and 8F).

The Immunological Activity of pINS-d Via IL-1R1

The inventors of the present disclosure tested whether the IL-1 receptor antagonist (IL-1Ra) competes with pINS-d because the pattern of pINS-d-mediated IL-6 induction was highly similar to induction by IL-1α. INS-d-mediated IL-6 production was completely inhibited by IL-1Ra in A549 epithelial and HUVEC endothelial cells in a dose-dependent manner (FIGS. 2A and 2B). In immune cells, pINS-d-mediated IL-6 production was only partially inhibited even at high concentrations of IL-1Ra (FIGS. 2C and 2D). Interestingly, IL-1β-mediated cytokines productions were inhibited by IL-1Ra in primary WBC, including THP-1 cells (FIGS. 8B and 8D), and the inhibition was not dependent on the cell type. This data further confirmed the existence of common activity between pINS-d and IL-1α, and support pattern found in earlier testing with INS and IL-1α-induced IL-6 production in different cell types.

Next, the inventors of the present disclosure reconstituted IL-1R1 in Wish cells in order to prove the role of IL-1R1 directly in pINS-d activity. IL-1R1 expression was not detected in mock Wish clone (FIG. 2E, lane 1); however, IL-1R1 expression in Wish C-3 and C-18 was confirmed by RT-PCR (FIG. 2E). In addition, protein expression of IL-1R1 was verified with western blotting (FIG. 2F) as well as with FACS analysis (FIG. 10A). The inventors of the present disclosure first examined whether the expression of IL-1R1 in Wish IL-1R1 clones restored its activity. IL-1α and IL-1β dramatically enhanced IL-6 production upon the reconstitution of IL-1R1 but the control mock remained inactive (FIGS. 10B and 10C). IL-6 was significantly increased in Wish IL-1R1/C-3 and /C-18 after pINS-d stimulation in a manner, similar to the enhancement of IL-1α and IL-1β activity, but the mock control clone did not respond to pINS-d (FIG. 10D). Dose-dependent pINS-d-mediated IL-6 production (FIG. 2G) was reversed by IL-1Ra (FIG. 2H) in Wish IL-1R1/C-3. This further verified that pINS-d utilizes IL-1R1. The pattern of IL-1Ra inhibition in Wish IL-1R1/C-3 was notably similar to the results of the A549 and HUVEC assay (FIGS. 2A and 2B).

Identifying a Motif of Insulin/Interleukin-1α (INS/IL-1α)

IL-6 production by pINS-d in A549 cells increased in a time dependent manner (FIG. 3A) while IL-1α levels decreased with prolonged incubation time (FIG. 3B). The inventors of the present disclosure used an IL-1α enzyme-linked immunosorbent assay (ELISA) to detect IL-1α levels in the A549 cell culture supernatant. The IL-1α ELISA was developed with a mAb raised against mature IL-1α as a capture antibody and an affinity-purified rabbit polyclonal antibody raised against the same antigen as the detection antibody (see Examples). The inventors of the present disclosure then performed a western blot with the supernatant of pINS-d-treated A549 cells by using the rabbit polyclonal antibody. Surprisingly, the polyclonal antibody accurately detected bands in the pINS-d-treated A549 cells but not in those cells treated with comINS (FIG. 3C). The inventors of the present disclosure compared the results of our IL-1α ELISA to the results from a commercial IL-1α ELISA kit. The IL-1α ELISA detected pINS-d while the commercial kit failed to detect pINS-d (FIG. 11A). No IL-6 induction was observed in the presence of trypsin. An additional experiment where trypsin was used to degrade pINS-d prior to detection the pINS-d band by western blotting (FIG. 11B) suggests that the added recombinant pINS-d protein is responsible for IL-6 induction in A549 cell assay (FIG. 11C).

These results illustrate that pINS likely shares an epitope with IL-1α that is recognized by the rabbit polyclonal antibody or mouse mAb raised against IL-1α. A sequence analysis of pINS and IL-1α revealed an INS/IL-1α motif of 7 amino acid residues "VELGGGP" (SEQ ID NO: 7) with 71.4% identity or 16 amino acid residues with 43.8% identity in the C-peptide of pINS (FIG. 12A and FIG. 12B). Alternatively, a dot-blot experiment demonstrated that the mAb anti-IL-1α recognized pINS-d but failed to recognize mature comINS (FIG. 3D, upper line). The INS/IL-1α homology motif in C-peptide does not exist in the comINS which lacks the C-peptide. The mAb raised against IL-1α recognized both precursor and mature IL-1α (FIG. 3D), but failed to recognize mature IL-1β (FIG. 4C).

In order to verify the presence of an anti-IL-1α mAb in the C-peptide (FIGS. 12A and 12B), the motif of INS/IL-1α C1 and C2 in the C-peptide of pINS was deleted by using a PCR mutagenesis method (Kim, S H et al., Proc Natl Acad Sci USA 98 (6), 3304-3309 (2001)). The recombinant proteins of the pINS-d wild type (WT), pINS-d/C1, and pINS-d/C2 were expressed and purified as shown in FIG. 3E. The inventors of the present disclosure examined whether mAb anti-IL-1α recognizes the pINS-d/C1 and pINS-d/C2 motifs. As expected, mAb anti-IL-1α recognized the motif of INS/IL-1α in FIG. 3F. The pINS-d/C1 of 7 amino acids was found to be more critical compared to the pINS-d/C2 with 16 amino acids deletion in the recognition of mAb anti-IL-1α.

Activity of INS/IL-1α Motif Mutants Varied Between Cell Types

The recombinant pINS-d/WT, pINS-d/C1 and pINS-d/C2 were used to stimulate A549 and HUVEC cells to examine biological activity. pINS-d/C1 and pINS-d/C2 were more effective in enhancing activity compared to pINS-d/WT, with pINS-d/C2 exhibiting the highest activity (FIGS. 3G and 3H). Interestingly, pINS-d/C2 entirely lost its activity in WBC and PMN cells, but pINS-d/C1 was greatly enhanced compared to the activity of pINS-d/WT (FIGS. 3I and 3J). The biological activity of pINS-d/WT, pINS-d/C1, and pINS-d/C2 varied across cell types.

The INS/IL-1α homology motif at the C-terminus of IL-1α (FIGS. 12A and 12B) was also deleted in the same manner that the motif was deleted in the pINS-d mutants. The recombinant proteins of IL-1α/WT, IL-1α/C1, and IL-1α/C2 were expressed and purified with HPLC as shown in FIGS. 4a and 4b. IL-1α/WT exists as a dimeric form in its non-reduced condition and the underlined cysteine residue in the homology motif "VCLAGGP" (SEQ ID NO: 6) is responsible for an inter disulfide bond (FIG. 4A). In its reduced condition with dithiothreitol (DTT), IL-1α/WT adopts monomer form similar to those of IL-1α/C1 and/C2 which both lack the cysteine residue (FIG. 4B). IL-1α/WT and two mutants were checked with the mAb raised against IL-1α. Surprisingly, the recognition pattern was similar to that of pINS-d in FIG. 3F, but the sensitivity of IL-1α/C2 by mAb anti-IL-1α was slightly higher than that of IL-1α/WT (FIG. 4C). As expected, the mAb anti-IL-1α failed to recognize IL-1β (FIG. 4C, bottom line).

The inventors of the present disclosure then examined the biological activities of three IL-1α forms. IL-1α/C1 and C2 lost their activities in A549 and HUVEC cells (FIGS. 4D and 4E), while pINS-d/C1 and C2 did not (FIGS. 3G and 3H). However, IL-1α/C2 significantly increased its activity in WBC (FIG. 4F) while pINS-d/C2 did not (FIG. 3I). In PMN, IL-1α/WT and IL-1α/C2 exhibited normal activity, but IL-1α/C1 remained inactive (FIG. 4G).

Cross Reaction of INS/IL-1α Motif by a Monoclonal Antibody Raised Against pINS-d or IL-1α Independently Next, the inventors of the present disclosure developed mAb against pINS-d. The inventors of the present disclosure identified a specific mAb against pINS-d after extensive epitope screening with comINS, pINS-m, and pINS-d (not shown). As shown in FIG. 5A, the mAb raised against pINS-d specifically recognized pINS-d/WT, but failed to recognize pINS-m and comINS (FIG. 5A, bottom two lines). The inventors of the present disclosure also compared pINS-d/C1 and C2 with pINS-d/WT in the same blot. Surprisingly, the recognition pattern by mAb anti-pINS-d was cognate with that of mAb anti-IL-1α (FIG. 3F). The mAb anti-pINS-d detected pINS-d/WT with highest sensitivity while detection of pINS-d/C1 was weakest (FIG. 5A, upper three lines). The inventors of the present disclosure also blotted IL-1α mutants with mAb anti-pINS-d (FIG. 5B) and, surprisingly, the result was consistent with the results for mAb anti-IL-1α (FIG. 4C), but the sensitivity of IL-1α/C2 was lower than that of IL-1α/WT.

Incomplete Inhibition of mAb Developed Against pINS-d or IL-1α

The mAb anti-pINS-d was examined to determine whether it would be able to inhibit pINS-d-mediated IL-6 production. With A549 and HUVEC cells, mAb anti-pINS-d incompletely suppressed IL-6 (FIGS. 5C and 5D) while IL-1Ra completely suppressed IL-6 (FIGS. 2A and 2B). The suppression of IL-6 production in Wish IL-1R1/C-3 was more effective when compared to suppression in other cell types (FIG. 5E), which is very similar to the inhibitory activity of IL-1Ra (FIGS. 2A, 2B, and 2H). In WBC, mAb anti-pINS-d inhibited IL-6 sufficiently but not in a dose-dependent manner (FIG. 5F). However, mAb anti-pINS-d failed to block IL-6 in the PMN assay (FIG. 5G). In addition, the mAb anti-pINS-d was used for IL-1α-mediated IL-6 inhibition (FIG. 13). The pattern of inhibition was similar to that of pINS-d except for a reversed dose response in WBC (FIG. 13D).

Next, the mAb anti-IL-1α which recognizes pINS-d was tested for inhibitory effects on pINS-d-induced IL-6 production. The effect of the mAb anti-IL-1α in FIGS. 6A to 6E was similar to that of mAb anti-pINS-d with a minor difference in the PMN assay (FIGS. 5C to 5G). The mAb anti-pINS-d suppressed IL-6 production in PMN (FIG. 6E), but this inhibition was not observed with mAb anti-IL-1α (FIG. 5G). Similar to the Wish IL-1R1/C-3 with mAb anti-pINS-d (FIG. 5E), the inhibitory activity of mAb anti-IL-1α increased in a dose-dependent manner (FIG. 6C). With further examination of IL-1α activity, it was found that IL-6 was suppressed by mAb anti-IL-1α in A549 and Wish/IL-1R1 C-3 but was much less effective compared to pINS-d (FIGS. 14A and 14C). The mAb anti-IL-1α failed to inhibit IL-1α-mediated IL-6 in HUVEC, WBC, and PMN (FIGS. 14B, 14D, and 14E).

Specific Biological Activity of pINS-d In Vivo

The inventors of the present disclosure investigated the pINS-d mediated immune response with in vivo experiments using IL-1R1 deficient mice. The pINS-d/C1 was most active among different pINS-d proteins in WT mice (FIG. 7A). As shown in FIGS. 7B to 7D, INS-d/WT, INS-d/C1, and INS-d/C2 mediated mouse IL-6 levels were significantly reduced in IL-1R1 deficient mice. This data further confirmed that pINS-d elaborates IL-1R1 to induce immune cytokines in vivo. The inventors of the present disclosure validated the organ specific responsiveness of pINS-d with mouse primary cells in vitro. The pattern of IL-6 production in IL-1R1 deficient mice (FIGS. 7F to 7J) was similar to that of in vivo experiment. The inventors of the present disclosure first examined mouse IL-1R1 mRNA expression in the lung of WT and IL-1R1 deficient mice. As shown in FIG. 7E, IL-1R1 expression was observed in WT mice but not in IL-1R1 deficient mice. Next, the inventors of the present disclosure performed in vitro experiment to compare the responsiveness of IL-1R1 deficient mice to WT mice. As expected, IL-1R1 deficient mice produced much less IL-6 after stimulation with pINS-d/WT and mutants (FIGS. 7F to 7J). The pINS-d/WT and two mutants induced IL-6 in a similar manner in the mouse WBC assay (FIGS. 7F to 7H); however, pINS-d/WT-induced IL-6 was most significantly reduced in IL-1R1 deficient mice. In BM cells experiments, pINS-d/C2 was highly active (FIG. 7J), but there was no induction of IL-6 with pINS-d/WT (not shown). The activity of pINS-d/C1 was very weak compared to that of pINS-d/C2 (FIG. 7I). The inventors of the present disclosure further examined mouse IL-1α and IL-1β activities with IL-1R1 deficient mice. The induction of mouse IL-6 and TNFα by IL-1α in WT mice was far more effective than induction by IL-1β, but mouse IL-6 and TNFα was not induced in IL-1R1 deficient mice (FIGS. 15A and 15B). In the mouse WBC assay, both IL-1α and IL-1β induced mouse IL-6 in WT mice, while there was a significant reduction of IL-6 in IL-1R1 deficient mice (FIGS. 15C and 15D). Only IL-1α showed activity in BM cells while the IL-6 reduction in IL-1R1 deficient mice was ineffective compared to IL-6 reduction in WBC (FIG. 15E).

In addition, the negative effect of synthetic peptide of the INS/IL-1α motif on pINS-d and IL-1α activity is corresponded to natural occurred two insulin isoforms. The synthetic peptides suppressed both pINS-d and IL-1α activity in WBC, while not in PMN (FIGS. 16B to 16E). Like pINS-d/C1, two natural splice variants, which were deleted amino acid residues as underlined, (FIG. 16F) increased their activities compared to pINS (86aa) (FIG. 16G). In summary, the data above suggests that mature INS regulates glucose uptake and pINS-d induces immune responses via IL-1R1 (FIG. 7K).

According to the exemplary embodiments of the present disclosure, since the pINS-d of the present disclosure has immunological activity, the pINS-d can be applied as an immune enhancer to diabetic patients.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

In FIG. 1A, recombinant pINS-m A/B, and in FIG. 1B pINS-d protein were pooled from HPLC fractions as indicated at the bottom and visualized by silver staining. The purity and concentration was compared to BSA on the right side. Biological activity of pINS-m, pINS-d, and comINS was examined with A549 (FIG. 1C), HUVEC (FIG. 1D), primary human WBC (FIG. 1E), PBMC (FIG. 1F), and PMN (FIG. 1G). Data in FIGS. 1C to 1G are comparisons between the control and pINS-d treatment. Data are mean±SEM; #, p<0.001 (from three replicates). All data shown are representative of at least five independent experiments.

In FIG. 2A pINS-d-induced IL-6 in A549, and in FIG. 2B HUVEC cells, was effectively suppressed with low concentrations of IL-1Ra while pINS-d-induced IL-6 of (FIG. 2C) primary WBC and (FIG. 2D) PMN was only partially inhibited even with high concentrations of IL-1Ra. FIGS. 2E to 2H illustrate reconstitution of IL-1R1 and IL-1Ra activity in Wish IL-1R1/Clone 3 (C-3). IL-1R1 was not detected in the mock Wish in the left lane but IL-1R1 expression was shown in C-3 and C-18 by (FIG. 2E) RT-PCR and (FIG. 2F) western blot. In FIG. 2G, Wish IL-1R1/C-3 was tested with different concentrations of pINS-d including a high concentration of pINS-m as indicated on the x-axis. In FIG. 2H, pINS-d-mediated IL-6 in Wish IL-1R1/C-3 was specifically inhibited by IL-1Ra. Concentrations of IL-1Ra and pINS-d were defined at the bottom of the graph. Data in FIG. 2G is a comparison between the control and treatment as depicted in FIGS. 2A to 2D. FIG. 2H are comparisons between standalone pINS-d and IL-1Ra pretreated to the cells with different concentration as defined on the bottom. Data are mean±SEM; #, p<0.001 (from three replicates). All data shown are representative of at least five independent experiments.

In FIG. 3A, IL-6 levels in the supernatant of A549 cells treated with pINS-d was increased by prolonged incubation but in FIG. 3B IL-1α levels were decreased with prolonged incubation as measured by the IL-1α ELISA kit. Incubation time is indicated on the x-axis. In FIG. 3C, a Western blot with affinity-purified rabbit polyclonal antibody raised against IL-1α detected 26 and 75 kDa bands only where pINS-d was added and not where PBS or comINS was added. In FIG. 3D, is illustrated a dot blot of various INS proteins with the mAb anti-IL-1α. The mAb recognized pINS-d but failed to recognize comINS. ProIL-1α and mature IL-1α were detected by the mAb anti-IL-1α. In FIGS. 3E and 3F, deletion of motifs C1 (7 amino acids) and C2 (15 amino acids) in the C-peptide was shown. In FIG. 3E, the recombinant proteins of WT, C1, and C2 pINS-d were visualized by silver staining. The purity and concentrations were compared with BSA. In FIG. 3F, the dot blot shows that the detection sensitivity of mAb anti-IL-1α was reduced in pINS-d/C1 and /C2 when compared to that of pINS-d/WT. FIGS. 3G to 3J depict a bioassay of pINS-d/WT, /C1, and /C2. The recombinant pINS-d/WT, C1, and C2 proteins were used to treat A549 and HUVEC cells. In FIG. 3G, pINS-d/C1 and pINS-d/C2 were more active than pINS-d/WT in A549 cells, however; in FIG. 3H, only pINS-d/C2 was more active than pINS-d/WT in HUVEC cells. Interestingly, pINS-d/C2 completely lost its activity in both (FIG. 3I) primary WBC and (FIG. 3J) PMN while pINS-d/C1 remained highly active. Data in FIGS. 3A and 3B and FIGS. 3I and 3J are comparisons between the control and treatments and FIGS. 3G and 3H are comparisons between pINS-d/WT and the mutant. Mean±SEM; *, p<0.05; **, p<0.01; #, p<0.001 (from duplicates). All data shown are representative of at least five independent experiments.

In FIGS. 4A to 4C, deletion of the motif IL-1α/C1 (7 amino acids) and /C2 (16 amino acids) at C-terminus was shown in FIG. 12. Recombinant proteins of IL-1α/WT, /C1, and /C2 were visualized by silver staining in their (FIG. 4A) non-reduced and (FIG. 4B) reduced conditions. IL-1α/WT in its non-reduced form exists in a dimer form indicated by arrow. In FIG. 4C, the dot blot shows that the detection sensitivity of anti-IL-1α was reduced in IL-1α/C1 compared to IL-1α/WT, but IL-1α/C2 detection sensitivity was enhanced. The concentration is defined at the top. FIGS. 4D-4G show a bioassay of IL-1α/WT, /C1, and /C2. In FIGS. 4D and 4E, A549 and HUVEC cells were treated with IL-1α/WT, IL-1α/C1, and IL-1α/C2. Both IL-1α/C1 and IL-1α/C2 severely lost their activities compared to IL-1α/WT. In FIGS. 4F and 4G, surprisingly, the activity of IL-1α/C2 in WBC was greatly enhanced compared to IL-1α/WT while IL-1α/C1 remained inactive in PMN. Concentrations were indicated at the bottom of each graph. Data in FIGS. 4D to 4G are comparisons between pINS-d/WT and mutant. Mean±SEM; *, p<0.05; #, p<0.001 (from duplicates). All data shown are representative of at least five independent experiments.

In FIG. 5A, various pINS-d proteins were blotted with mAb anti-INS-d. pINS-m and comINS were not detected as shown in the bottom, but pINS-d/WT, pINS-d/C1, and pINS-d/C2 were recognized. The detection sensitivity of mAb anti-INS-d against pINS-d/C1 had reduced compared to pINS-d/WT and pINS-d/C2. B, IL-1α/WT, IL-1α/C1, and IL-1α/C2 were blotted with mAb anti-pINS-d and it was able to recognize the INS/IL-1α motif in IL-1α. The mAb anti-pINS-d failed to detect IL-1 cc/C1 while decreased detection sensitivity against pINS-d/C2 compared to pINS-d/WT. Concentrations were defined at the top. FIGS. 5C to 5G show an inhibition assay with mAb anti-pINS-d. The IL-6 levels by pINS-d in (FIG. 5C) A549, (FIG. 5D) HUVEC, and (FIG. 5E) Wish IL-1R1/C-3 were suppressed by mAb anti-pINS-d. Wish IL-1R1/C-3 was most sufficient with a dose-dependent manner. Concentrations of mAb anti-pINS-d were indicated on the x-axis. Data in FIGS. 5C to 5G are comparisons between standalone pINS-d and mAb anti-pINS-d premixed at different concentrations as defined at the bottom of graph. Data are mean±SEM; *, $p<0.05$; **, $p<0.01$; #, $p<0.001$ (from three replicates). All data shown are representative of at least four independent experiments.

(FIG. 6A) A549, (FIG. 6B) HUVEC, (FIG. 6C) Wish IL-1R1/C-3, (FIG. 6D) WBC, and (FIG. 6E) PMN were treated with mAb anti-IL-1α as defined on the x-axis. The observed suppression pattern of IL-6 production by mAb anti-IL-1α was similar to the suppression of mAb anti-pINS-d, but unlike its effect on PMN, mAb anti-IL-1α blocked IL-6 slightly at a high concentration. Concentrations of mAb anti-pINS-d were indicated on the x-axis. Data in FIGS. 6C to 6G are comparisons between standalone pINS-d and mAb anti-IL-1α premixed at different concentrations as defined at the bottom of each graph. Data are mean±SEM; *, $p<0.05$; **, $p<0.01$; #, $p<0.001$ (from duplicates). All data shown are representative of at least five independent experiments.

In FIG. 7A, pINS-d/WT, pINS-d/C1, and pINS-d/C2 (5 mg per mouse) were injected into WT mice to validate their activity. In FIGS. 7B to 7D, IL-1R deficient and WT mice were administered pINS-d/WT, pINS-d/C1, and pINS-d/C2 (5 mg per mouse) to verify the role of IL-1R1 in pINS-d-mediated immune responses in vivo. (FIG. 7B) pINS-d/WT, (FIG. 7C) pINS-d/C1, and (FIG. 7D) pINS-d/C2-induced mouse IL-6 production was significantly reduced in IL-1R deficient mice compared to WT mice. In FIG. 7E, RT-PCR of mouse IL-1R1 confirmed that IL-1R1 expression is absent in IL-1R deficient mice. In FIGS. 7F to 7J, validation of pINS-d-induced IL-6 with different immune cells in vitro. WBC of WT and IL-1R1 deficient mice were treated with (FIG. 7F) pINS-d/WT, (FIG. 7G) pINS-d/C1, and (FIG. 7H) pINS-d/C2 for mouse IL-6 induction. BM cells of WT and IL-1R1 deficient mice were treated with pINS-d/WT (not shown), (FIG. 7I) pINS-d/C1, and (FIG. 7J) pINS-d/C2. Concentrations of pINS-d were indicated on the x-axis. Data in FIGS. 7A to 7D and FIGS. 7F to 7J are comparisons of WT and IL-1R1−/−. Mean±SEM; *, $p<0.05$; **, $p<0.01$; #, $p<0.001$ (from duplicates). All data shown are representative of at least five independent experiments. FIG. 7K shows a schematic drawing of a distinct function of mature or pINS. PreproINS is produced from the pancreas by food uptake or other stimuli. Mature INS stimulates cells to uptake glucose while proINS-d induces immune responses in different cell types.

In FIG. 8A, pINS fractions from HPLC were used to treat HUVEC cells and significant induction of IL-6 was observed where dimeric pINS (pINS-d) appeared. Monomeric pINS (pINS-m) failed to induce IL-6. Numbers on the x-axis indicate pINS-d fractions possessing activity. In FIGS. 8B and 8C, the HPLC fractions of pINS-m from 41 to 44 and pINS-d from 45 to 60 were visualized by silver staining. pINS-d and pINS-m indicated by the arrow on the right. In FIG. 8D, several adherent epithelial cell lines and HUVEC endothelial cells highly sensitive to IL-1α and IL-1β were stimulated with 100 ng/ml of mature commercial INS (comINS), pINS-m, pINS-d, IL-1α, and IL-1β. HUVEC and A549 cells responded to pINS-d, IL-1α, and IL-1β, but comINS and pINS-m failed to respond. Hela and Wish cells remained inactive. In FIG. 8E, human primary whole blood cell (WBC), polymorphonuclear (PMN), and peripheral blood mononuclear cell (PBMC) were treated with the same stimuli as shown in FIG. 8D, but were treated with low concentrations of IL-1α and IL-1β (20 ng/ml) in PBMC (very high responsiveness). pINS-d and IL-1α exhibited similar activity on three different primary immune cells and IL-1α was twice as active as pINS-d. In WBC, the activity of IL-1β was lower compared to pINS-d and IL-1α while its activity remained intact in PBMC. Interestingly, a high concentration of IL-1β (100 ng/ml) was inactive in PMN. In FIG. 8F, a similar experiment was performed with THP-1 cells to confirm the inactivity of IL-1β was not due to variations between individuals. The data was consistent with the results of human primary immune cells. In FIGS. 8G to 8I, pINS-d or IL-1α-induced IL-1β, IL-6, and TNFα production in WBC (FIG. 8G), PMN (FIG. 8H), and PBMC (FIG. 8I) was examined. The concentrations are defined on the x-axis. FIGS. 8E and 8F illustrate comparisons between IL-1α and IL-1β-mediated cytokine inductions. FIGS. 8G, 8H and 8I illustrate comparisons between the control and pINS-d-mediated cytokine productions. The Data are mean±SEM; #, $p<0.001$ (from three replicates). All data shown are representative of at least six independent experiments. The responsiveness pattern of pINS in various cell types was highly similar to IL-1α, but not to IL-1β.

In FIG. 9A, IL-1α-induced IL-6 production in WBC was barely suppressed at high concentrations of IL-1Ra while in FIG. 9B, IL-1β-induced IL-6 was very sufficiently inhibited at low concentrations of IL-1Ra. In FIG. 9C, similar to WBC, IL-1Ra partially suppressed IL-1α-induced IL-6 in PMN. In FIG. 9D, THP-1 cells, pINS-d mediated IL-8 was not reduced by IL-1Ra, but IL-1β-induced IL-8 effectively inhibited by IL-1Ra. Although IL-1α-induced IL-8 in THP-1 cells was inhibited by IL-1Ra, there was no dose response. Data in FIGS. 9C and 9D are comparisons between stimuli in the absence and presence of IL-1Ra. Mean±SEM; *, $p<0.05$; **, $p<0.01$; #, $p<0.001$ (from three replicates). All data shown are representative of at least five independent experiments.

In FIG. 10A, FACS analysis verified the expression of IL-1R1 on the cell surface of Wish clone 3 and 18 and the lack of expression on the mock clone. In FIGS. 10B and 10C, the functional reconstitution of IL-1R1 on Wish IL-1R1/C3 and /C18 was confirmed by IL-1α and IL-1β. Compared to the mock control clone, a low concentration of IL-1α and IL-1β effectively increased IL-6 production. In FIG. 10D, Wish IL-1R1/C3, /C18, and mock clone were treated with pINS-m and pINS-d to test pINS-d activity depending on IL-1R1 expression. pINS-d greatly increased IL-6 production in Wish IL-1R1/C3 and /C18, but the mock control clone remained unresponsive. pINS-m was ineffective in inducing IL-6 in IL-1R1 reconstituted Wish clones. FIGS. 10B, 10C and 10D show data that are comparison between mock control and Wish IL-1R1 clones. Mean±SEM; #, p<0.001 (from three replicates). All data shown are representative of at least three independent experiments.

In FIG. 11A, anti-IL-1α mAb ELISA detected pINS-d, but failed to recognize comINS, which is mature INS lacking the C-peptide. A commercial IL-1α ELISA kit did not recognize pINS-d. In FIG. 11B, pINS-d was treated for 60 min in the presence or absence of trypsin (Sigma-Aldrich). pINS-d (loaded 100 ng/lane) was properly detected as a band of approximately 30 kDa, but pINS-d was not observed where trypsin was added. In FIG. 11C, the same batch of pINS-d in the presence or absence of trypsin was examined for IL-6 induction in A549 cells. The production of IL-6 was found to be due to pINS-d because trypsin abolished IL-6 production. Data in FIG. 11A are comparisons between a commercial IL-1α ELISA and IL-1α developed with the mAb anti-IL-1α. Data in FIG. 11C are comparisons between the presence and absence of trypsin. Mean±SEM; #, p<0.001 (from three replicates). All data shown are representative of at least three independent experiments.

FIGS. 12A and 12B illustrate identifying a motif in INS and IL-1α. Recognition of pINS-d by mAb generated against IL-1α suggests that IL-1α may share an epitope with pINS. The inventors of the present disclosure analyzed pINS and IL-1α by using an align program ch.embnet.org/software/LALIGN form.html). In FIG. 12A, there were two fragments of amino acid residues, a 7 amino acids named INS-d/C1 (71.4% identity; IL-1α: SEQ ID NO: 6; INS: SEQ ID NO: 7) and a 15 amino acids named INS-d/C2 (43.8% identity; IL-1α: SEQ ID NO: 12; INS: SEQ ID NO: 13). In FIG. 12B, the location of C1 and C2 was defined in mature human IL-1α (SEQ ID NO: 14) and pINS (SEQ ID NO: 1).

FIGS. 13A and 13B show that although IL-1α-induced IL-6 in A549 was inhibited significantly by anti-pINS-d mAb (from 0.3 to 1 mg/ml), there was no dose response. Significant inhibition was observed only at a high concentration (1 mg/ml) in HUVEC cells. FIG. 13C shows that anti-pINS-d mAb was most effective in inhibiting IL-6 induced by IL-1α in Wish IL-1R1/C-3. FIG. 13D shows that interestingly, the anti-pINS-d mAb was more effective in suppressing IL-6 at a low concentration and its effectiveness decreased with increasing concentration (1 mg/ml) in WBC. FIG. 13E shows that however, the anti-pINS-d mAb was ineffective in suppressing IL-6 production by IL-1α in PMN. Data in FIGS. 13A to 13E are comparisons between the absence and presence of anti-pINS-d mAb. Mean±SEM; *, p<0.05 (from three replicates). All data shown are representative of at least four independent experiments.

In FIGS. 14A and 14B, IL-1α-induced IL-6 in A549 was reduced significantly by anti-IL-1α mAb at a high concentration. No significant inhibition was observed in HUVEC. In FIG. 14C, the anti-IL-1α mAb sufficiently suppressed IL-6 production by IL-1α in Wish IL-1R1/C-3. In FIGS. 14D and 14E, as in HUVEC, the anti-IL-1α mAb was ineffective in suppressing IL-6 induced by IL-1α in WBC and PMN. Data in FIGS. 14A to 14E are comparisons between the absence and presence of anti-IL-1α mAb. Mean±SEM; *, p<0.05; **, p<0.01 (from three replicates). All data shown are representative of at least four independent experiments.

In FIGS. 15A and 15B, Mouse IL-1α and IL-1β were administrated into WT and IL-1R deficient mice. In FIG. 15A, IL-1α-induced mouse IL-6 was much stronger than that of IL-1β in vivo. In FIG. 15B, although TNFα level was much lower than IL-6 production, similar patterns of mouse TNFα induction were observed. FIGS. 15C and 15D illustrate an in vitro experiment defined IL-1α and IL-1β activity with different immune cell types. WBC, BM, spleen, thymus, lymph node cells were stimulated with mouse IL-1α and IL-1β. IL-1α—(FIG. 15C) and (FIG. 15D) IL-1β-stimulated WBC produced IL-6. IL-1α was twice as active as IL-1β, but WBC from IL-1R1 deficient remained inactive. In FIG. 15E, IL-1α was active in BM while IL-1β was inactive (not shown). Other immune cells, spleen, thymus, lymph node cells, did not exhibit responsiveness to IL-1α and IL-1β. Each concentration of treated IL-1α and IL-1β in vivo and in vitro is defined on the x-axis. Data in FIGS. 15A to 15E are comparisons between WT and IL-1R deficient mice. Mean±SEM; *, p<0.05; **, p<0.01; #, p<0.001 (from duplicates). All data shown are representative of at least five independent experiments.

FIG. 16A shows the amino acid sequence of three synthetic peptides. VCL (SEQ ID NO: 6) is the 7 amino acid residues of INS/IL-1α motif at C-terminal of IL-1α. VEL (SEQ ID NO: 7) is the 7 amino acid residues of INS/IL-1α motif in the C-peptide of INS. The C-pep (SEQ ID NO: 15) is the amino acid residues in pINS. The effect of the synthetic peptide on pINS-d (FIG. 16B) and IL-1α (FIG. 16C) mediated IL-6 in WBC was exhibited. VCL and VEL suppressed both pINS-d and IL-1α-induced IL-6 production, while the C-peptide weakly inhibited pINS-d-induced IL-6 production. In FIGS. 16D and 16E, there was no inhibitory effects on both pINS-d and IL-1α-induced IL-6 production in PMN. In FIG. 16F, two natural splice variants of INS sequence was shown by green bolded letters, which were underlined (Pro Insulin (83aa): SEQ ID NO: 16; Pro Insulin (74aa): SEQ ID NO: 17. The variants of human INS were expressed (not shown). In FIG. 16G, the recombinant protein of pINS (83aa) and pINS (74aa) activity was compared to pINS (86aa), which is known as INS2. pINS (74aa) was the most active in both monomeric and dimeric forms, but the monomeric form of pINS (83aa) and pINS (83aa) remained inactive. The activity of both pINS (83aa) and pINS (74aa) was higher than pINS (86aa) in THP-1 cells. Data in FIGS. 16B to 16E are comparisons between stimuli in the absence and presence of synthetic peptide (0.5 g/ml). Data in FIGS. 16D to 16G are comparisons between pINS-d (86aa) and splice variant. Mean±SEM; *, p<0.05; **, p<0.01; #, p<0.001 (from duplicates). All data shown are representative of at least three independent experiments.

DETAILED DESCRIPTION

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

Hereinafter, the present disclosure will be described in detail with reference to non-limited Examples. However, the following Examples are provided for the purpose of illustrating the present disclosure, but the scope of the present disclosure cannot be construed as being limited to the following Examples.

Example 1: Construction of Plasmid Vector

The inventors of the present disclosure obtained human INS cDNA from Dharmacon (Lafayette, Colo.) and transferred the open reading frame of pINS without the hydrophobic signal peptide of 24 amino acid residues into pProEx/HTa (Life Technologies, Grand Island, N.Y.) possessing a his-tag at N-terminus. Human precursor IL-1α, IL-1β and IL-1Ra cDNA were cloned as described in Hong, J. et al., *J Biol Chem* 286 (22), 20078-20086 (2011). Mature IL-1α 159 amino acid residues and IL-1β 153 amino acid residues at the C-terminus were transferred into the same vector for *E. coli* expression. However, mature IL-1Ra 153 amino acid residues was transferred into pET21a (Novagen, Madison, Wis.) possessing a his-tag at C-terminus because the N-terminal fusion peptide of pProEx/HTa disturbed IL-1Ra activity (not shown). Mouse IL-1α and IL-1β cDNA isolated from LPS-induced Raw 264.7 cells (not shown) and then processed for expression vector. The cDNA of IL-1R1 was cloned from A549 cells and then transferred into a mammalian expression vector pCAGGs/Neo for Wish cell stable clones. The sequence of the constructed vectors was confirmed by CosmoGen (Seoul, Korea).

Example 2: Mutagenesis

Figure 12B:
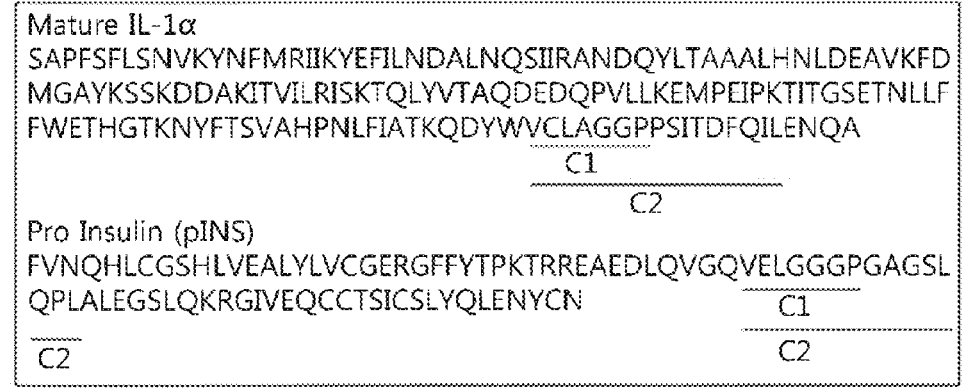
Figure 13A:
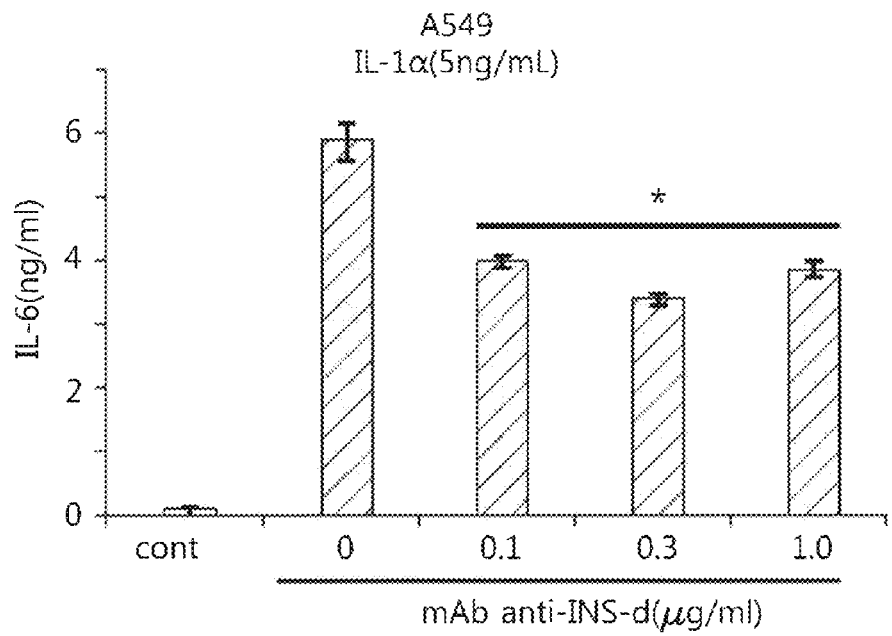
FIGS. 13A-13E illustrate the suppression of IL-1α-mediated IL-6 production by mAb raised against pINS-d in various cell types.
Figure 13B:
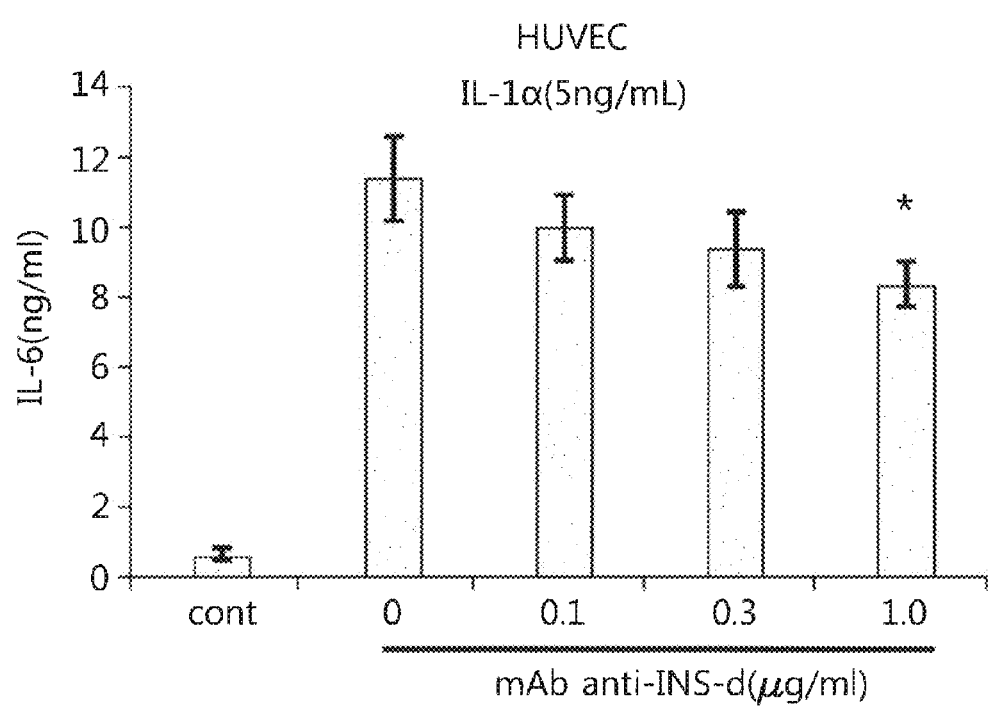
Figure 13C:
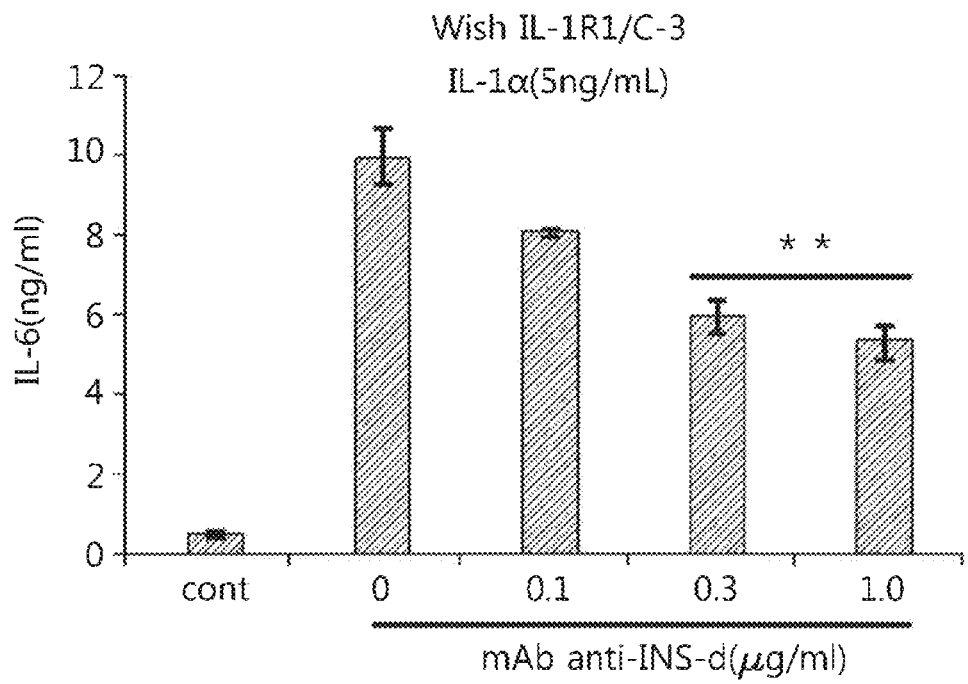
Figure 13D:
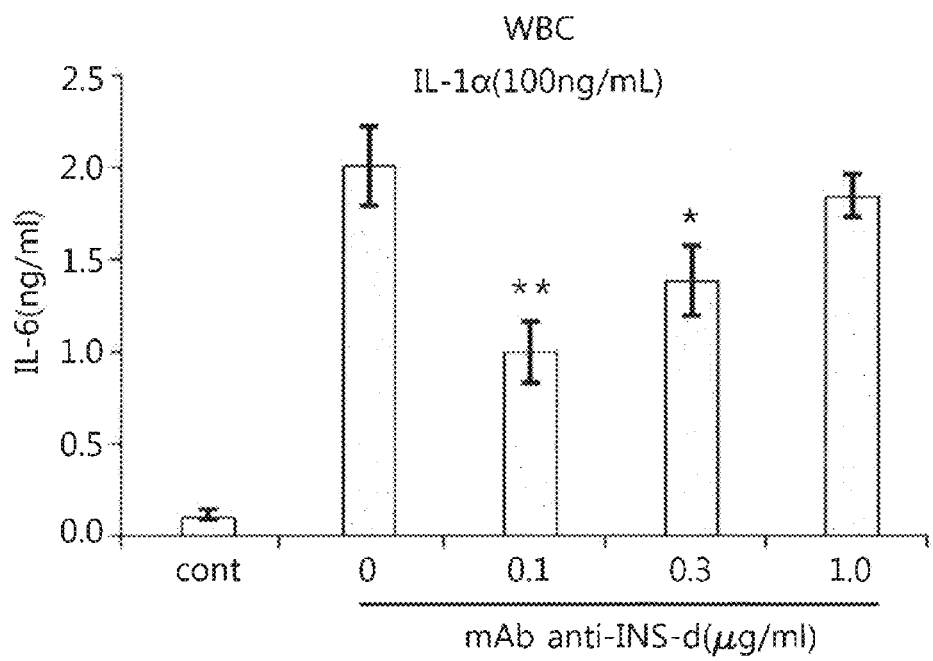
Figure 13E:
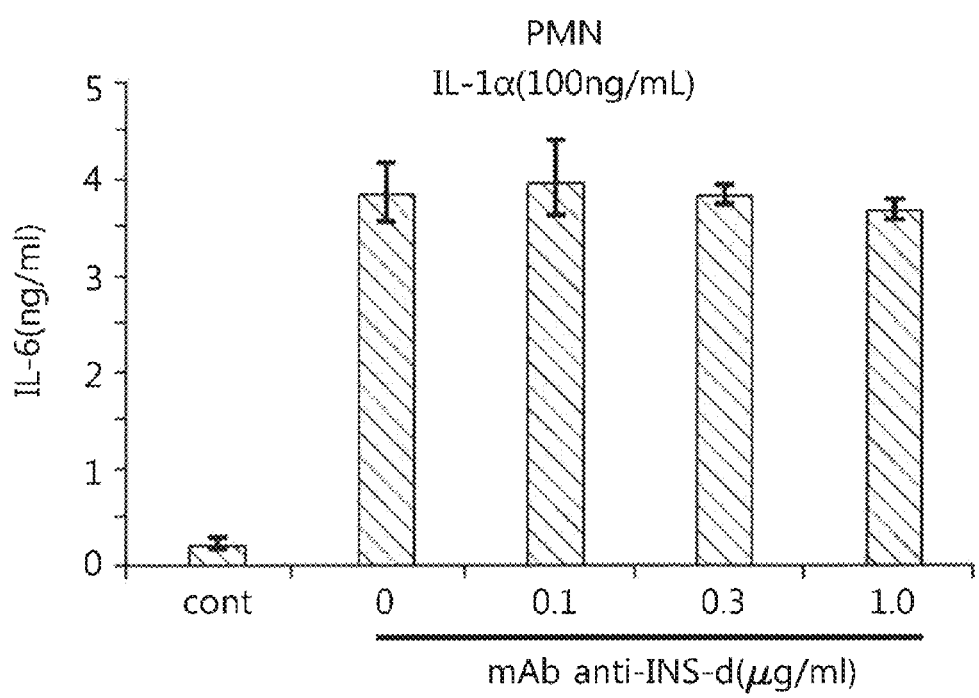
Figure 14A:
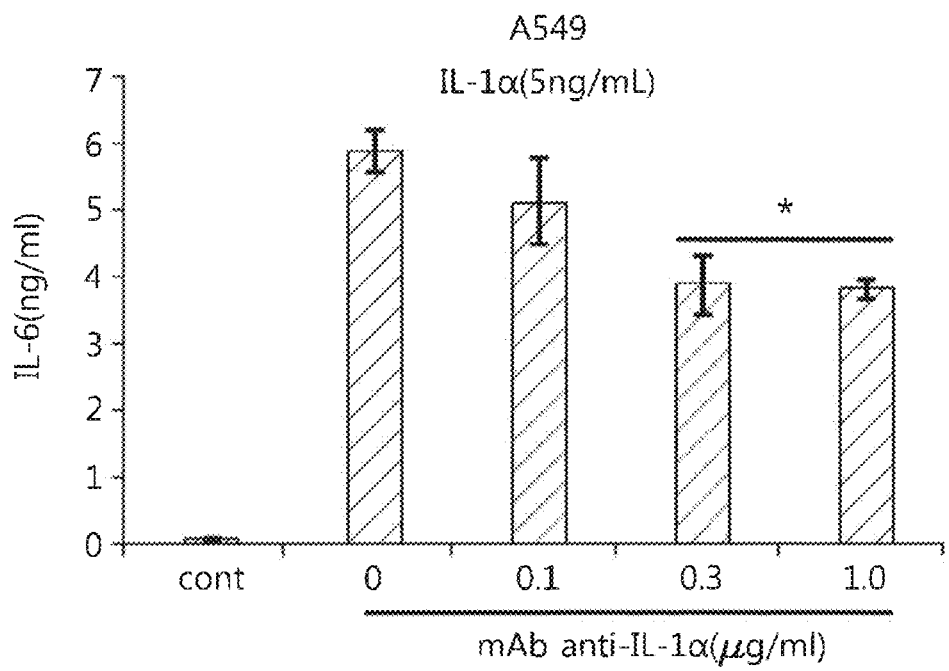
FIGS. 14A-14E illustrate the suppression of IL-1α-mediated IL-6 production by mAb generated against IL-1α in various cell types.
Figure 14B:
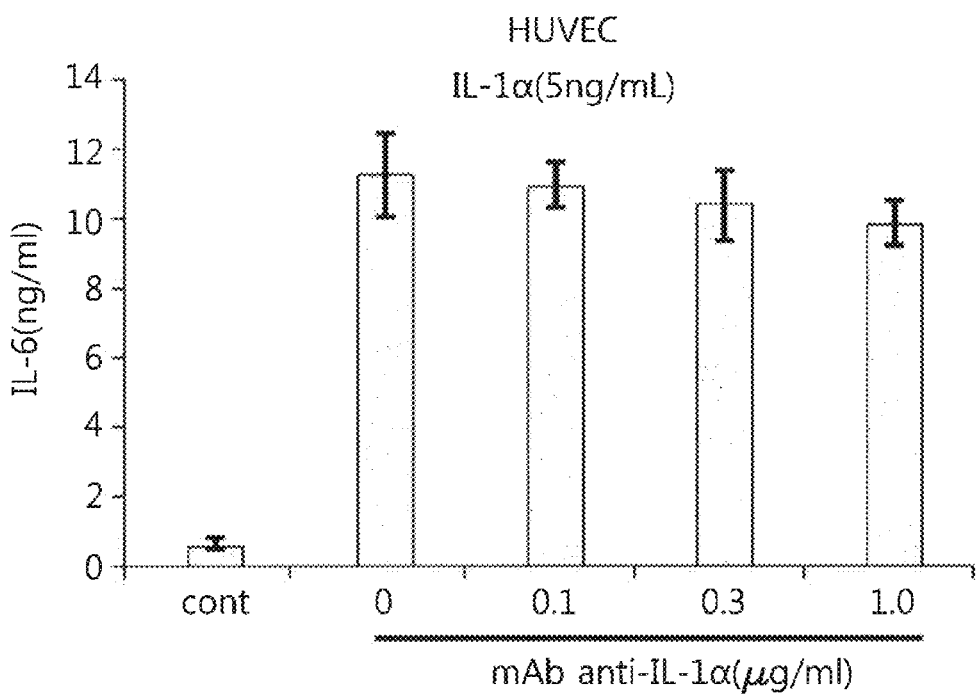
Figure 14C:
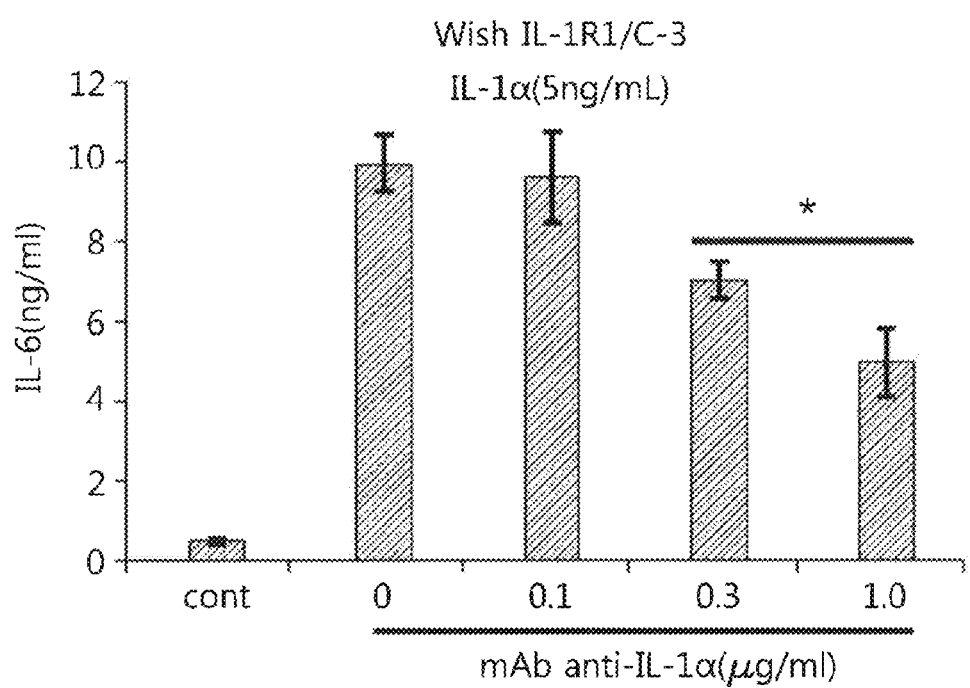
Figure 14D:
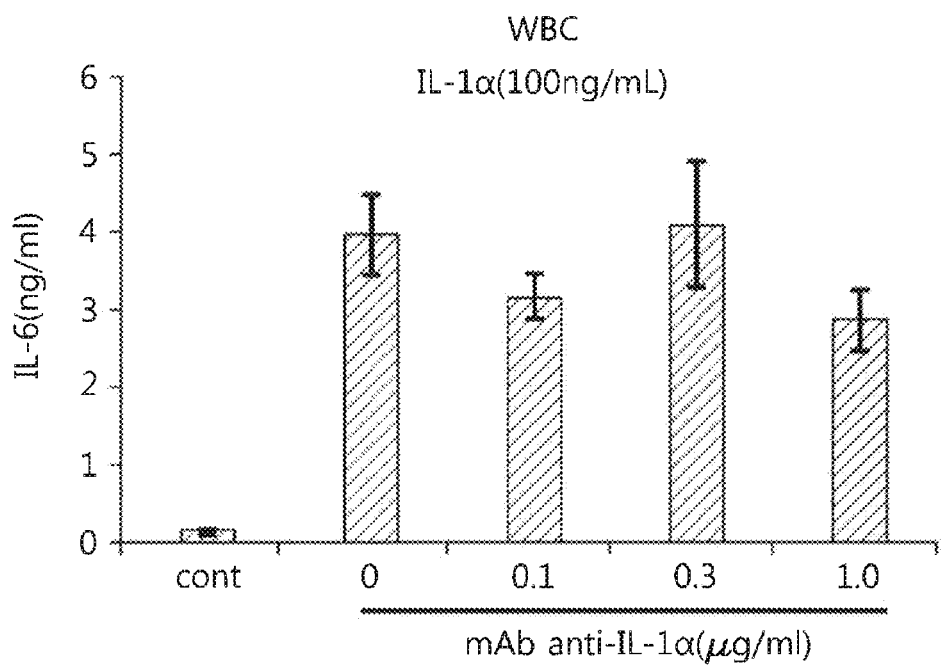
Figure 14E:
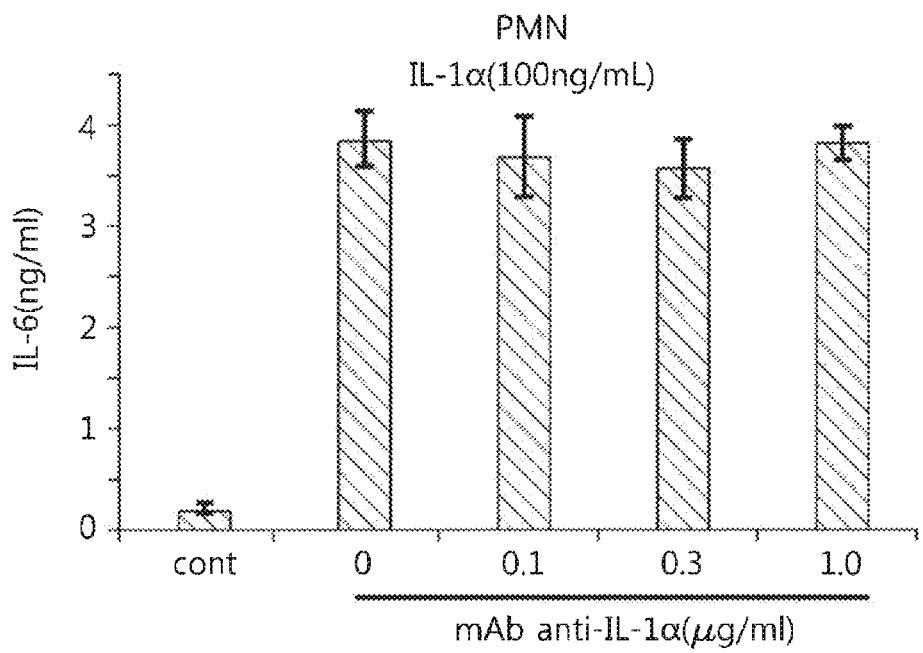
Figure 15A:
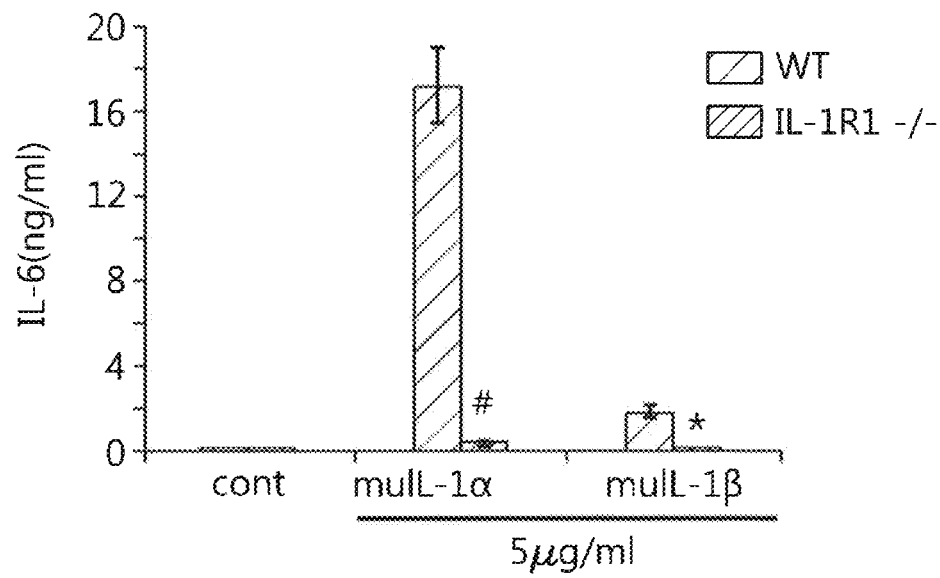
FIGS. 15A-15E illustrate that IL-1α and IL-1β-mediated cytokine productions decreased in IL-1R1 deficient mice.
Figure 15B:
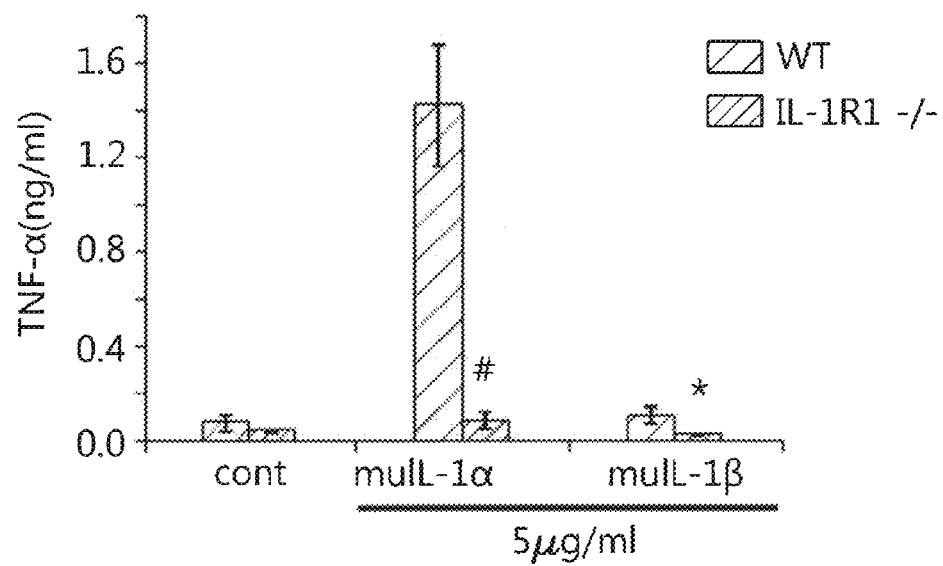
Figure 15C:
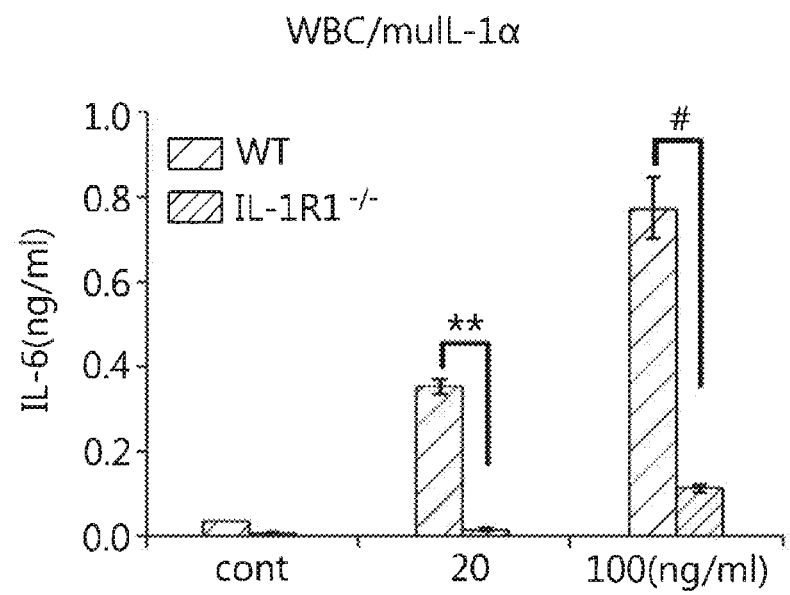
Figure 15D:
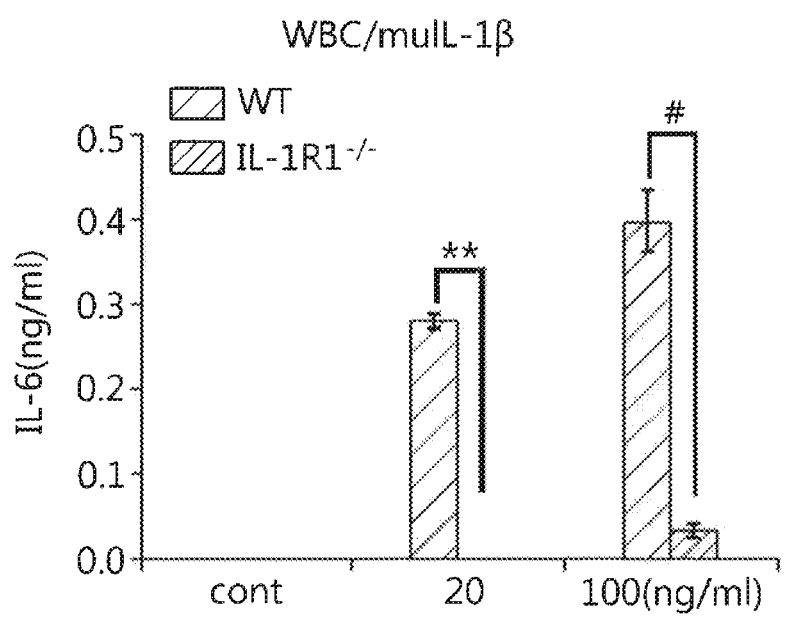
Figure 15E:
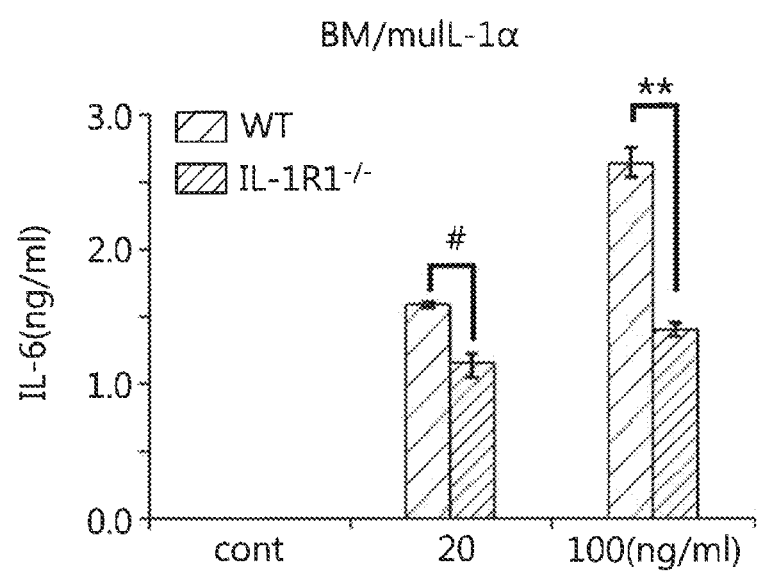
Figures 16A, 16B:
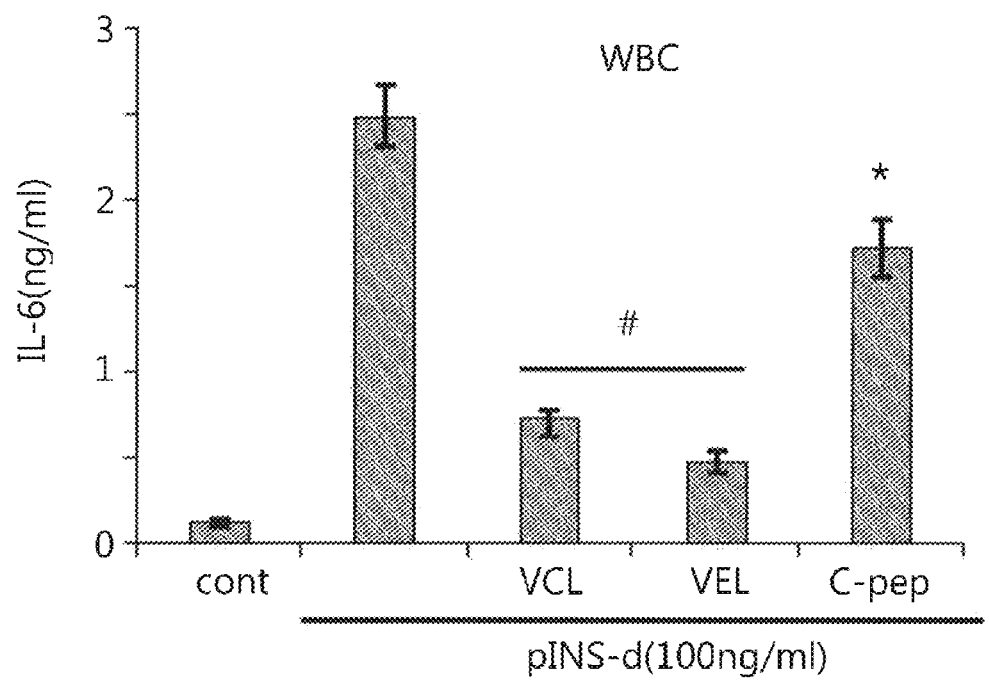
FIGS. 16A-16G illustrate that the negative effect of synthetic peptide of the INS/IL-1α motif on INS-d and IL-1α activity is corresponded to natural occurred two insulin isoforms.
Figure 16C:
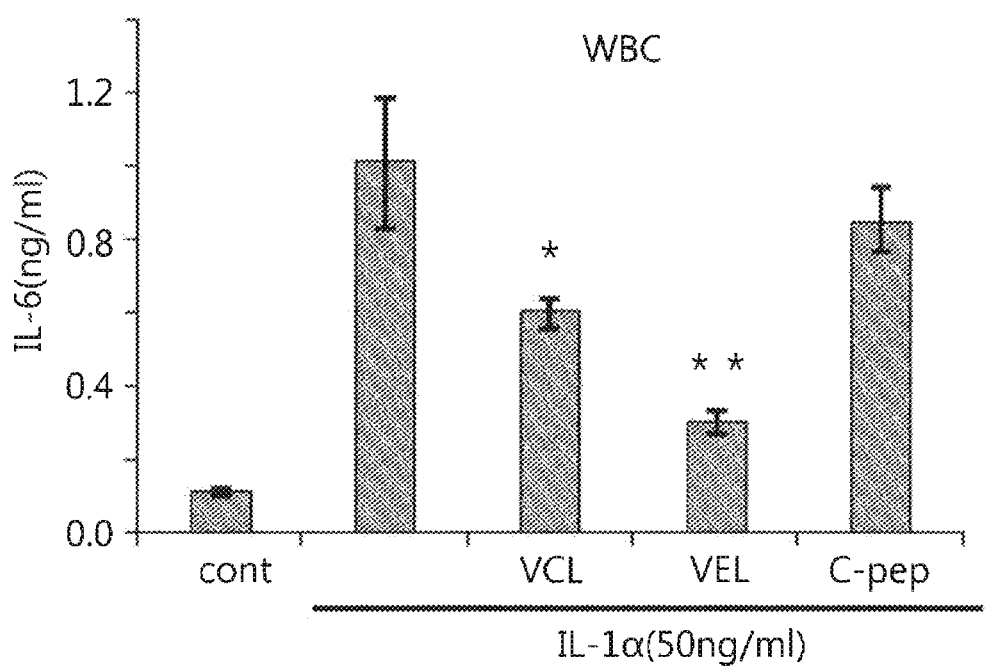
Figure 16D:
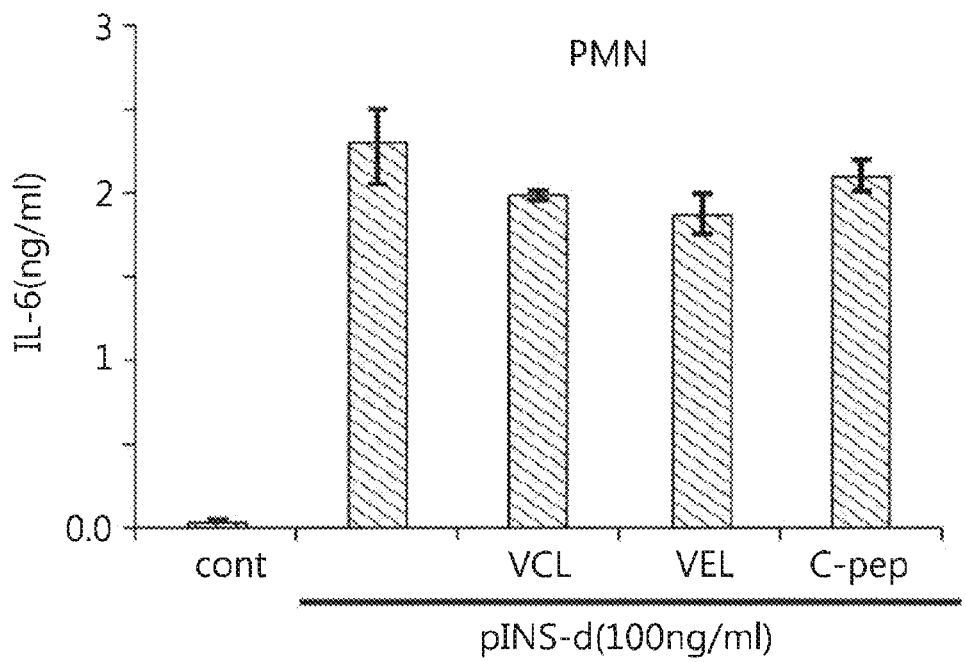
Figure 16E:
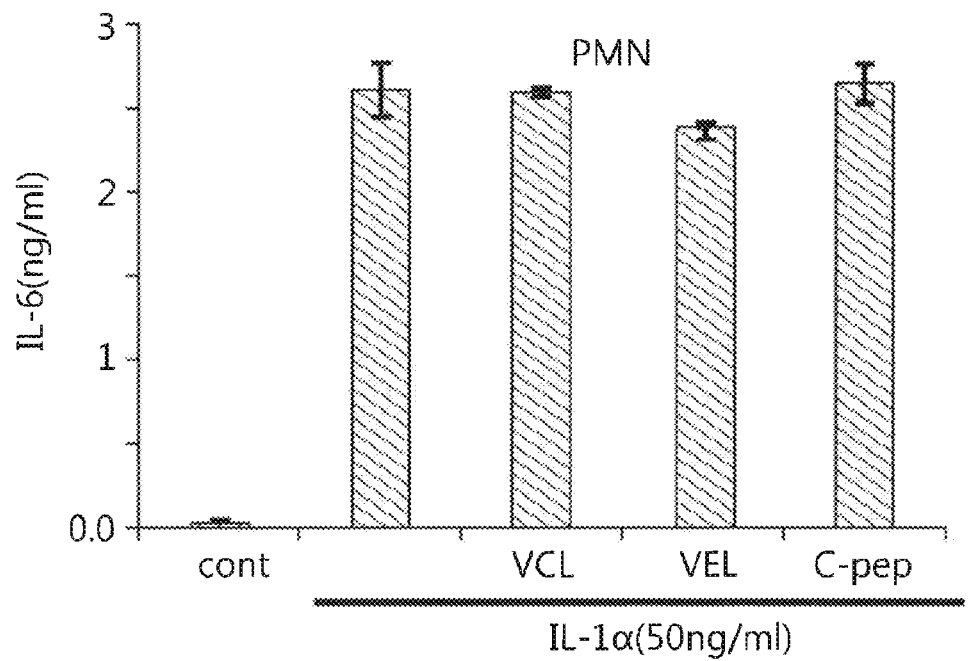
Figures 16F, 16G:
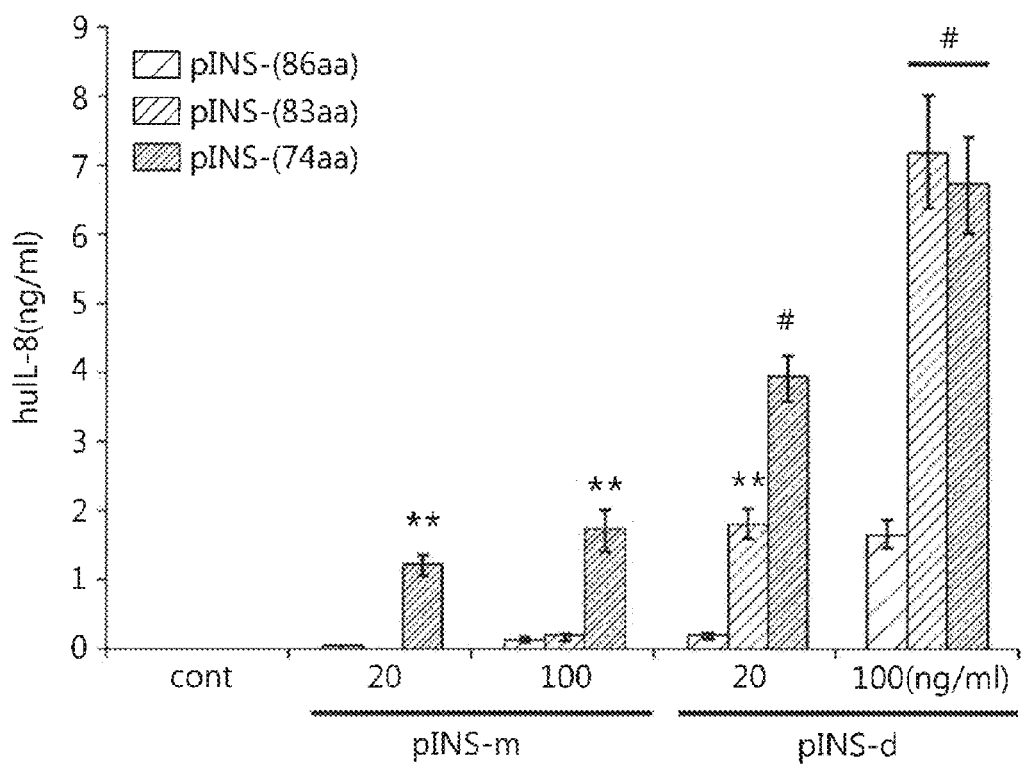

The cDNA of the plasmid vector from WT pINS and mature IL-1α were used as templates to generate mutant pINS/C1 and pINS/C2 as well as IL-1α/C1 and IL-1α/C2. The inventors of the present disclosure designed a specific sense and reverse primer (C1 sense-5' GGTGGGGCA-GGGTGCAGGCA (SEQ ID NO: 8), reverse-5' TGCCTG-CACCCTGCCCCACC (SEQ ID NO: 9), C2 sense-5' GGTGGGGCAGGCCCTGGAGG (SEQ ID NO: 10), and reverse-5' CCTCCAGGGCCTGCCCCACC (SEQ ID NO: 11)) that overlapped with the deletion site and removed the C1 and C2 motifs (FIG. 12). The inventors of the present disclosure generated an N-terminal piece PCR product and a C-terminal piece PCR product using the same sense and reverse primer from pProEx/HTa. The N and C-terminal PCR products were mixed in a 1:1 ratio and then used as a template to obtain a full length open reading frame of each cDNA-deleted the C1 and C2 sequence in pINS and mature IL-1α as shown in FIG. 12. The sequence of mutant vectors were confirmed (CosmoGen).

Figure 1A:
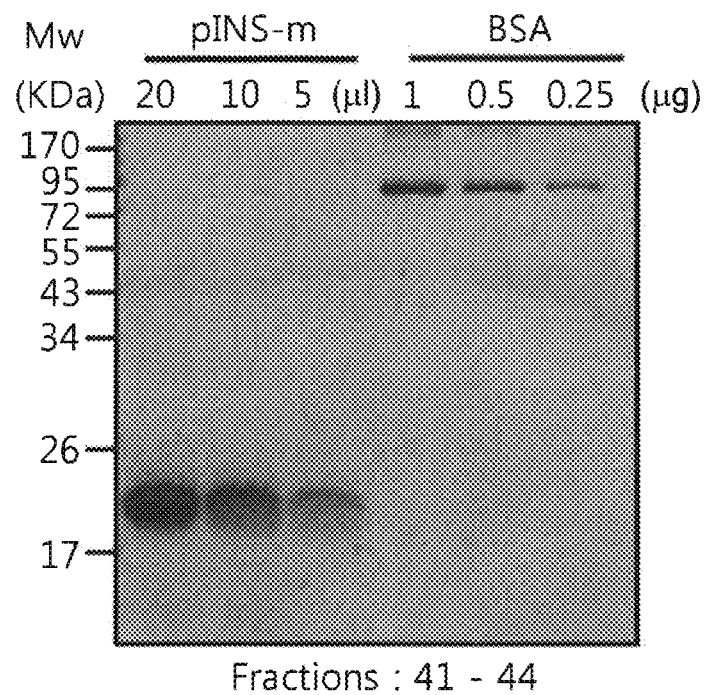
FIGS. 1A-1G illustrate expression and bioassay of recombinant pINS.
Figure 1B:
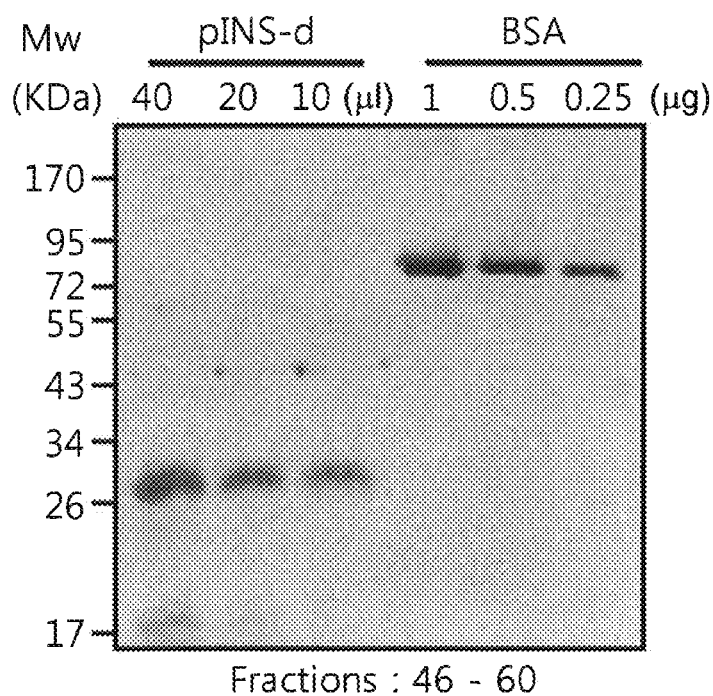
Figure 1C:
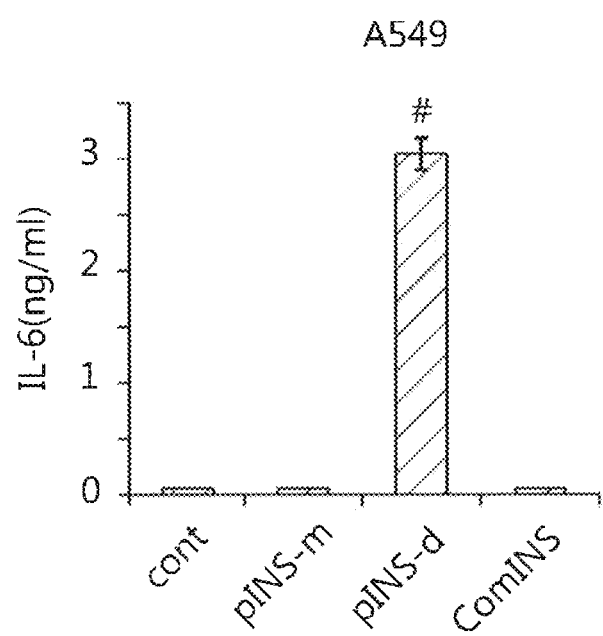
Figure 1D:
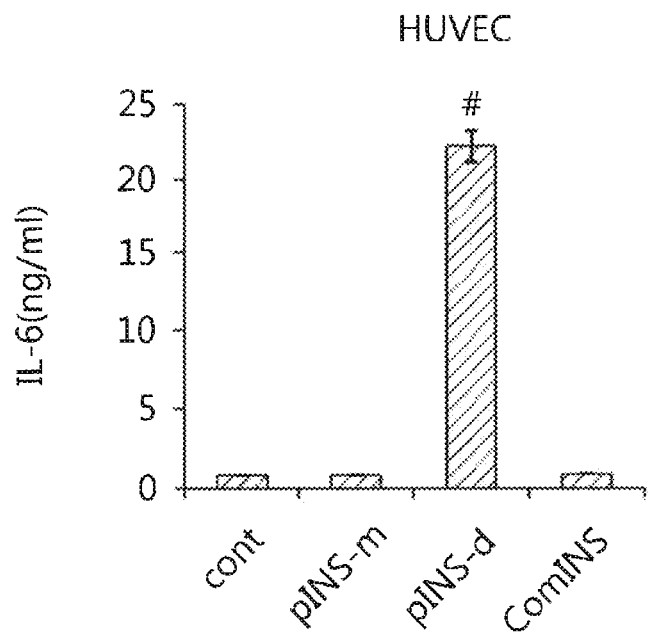
Figure 1E:
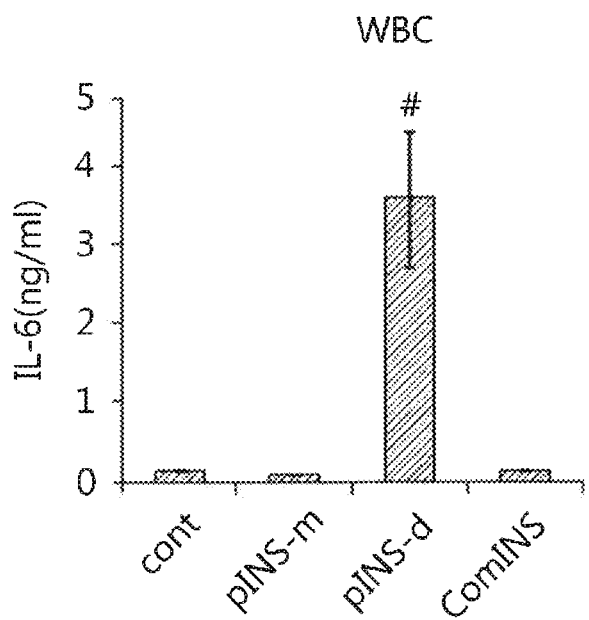
Figure 1F:
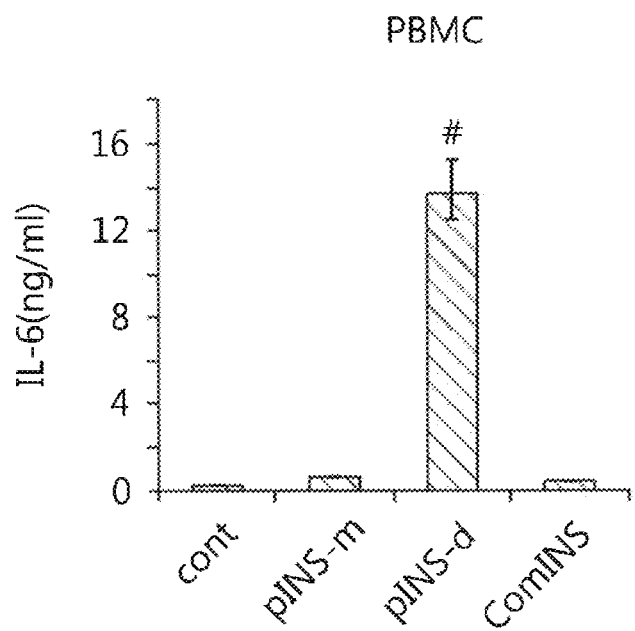
Figure 1G:
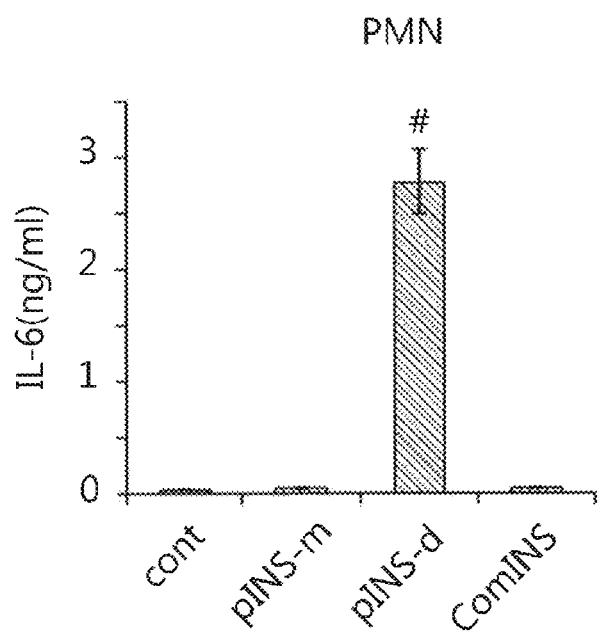
Figure 2A:
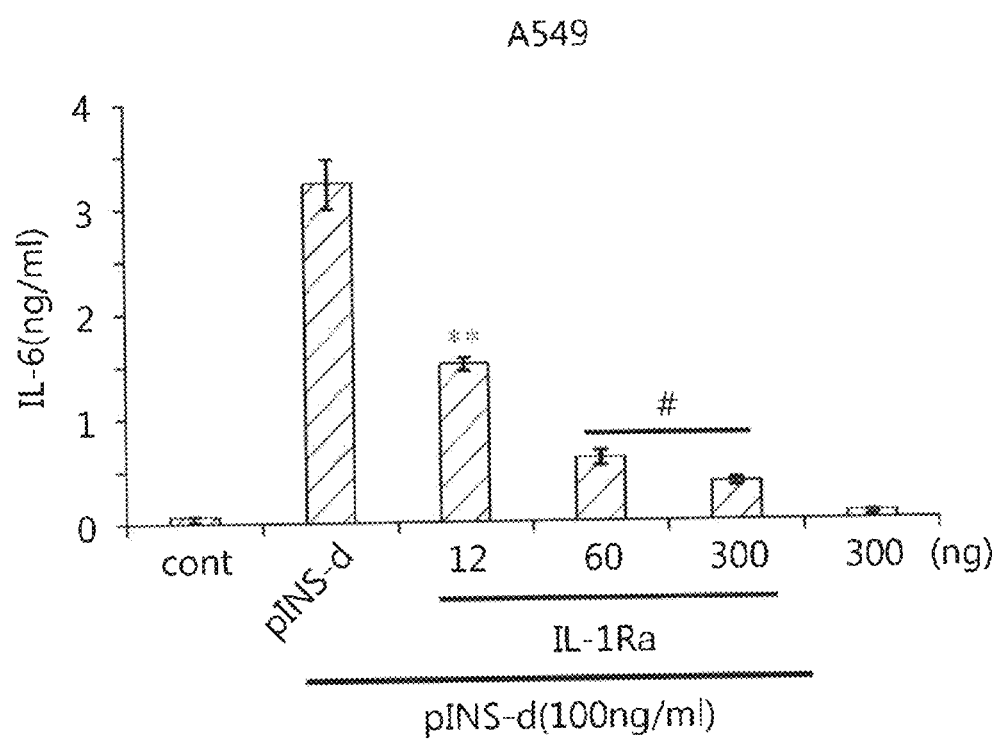
FIGS. 2A-2H illustrate the inhibition of pINS-d-mediated IL-6 production by IL-1Ra.
Figure 2B:
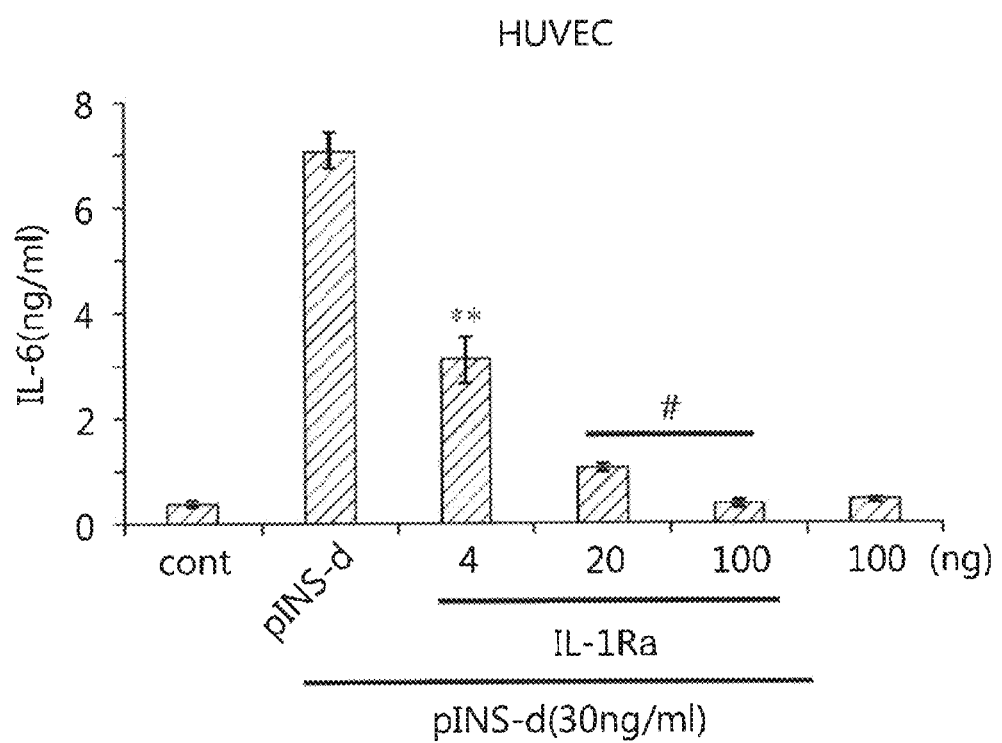
Figure 2C:
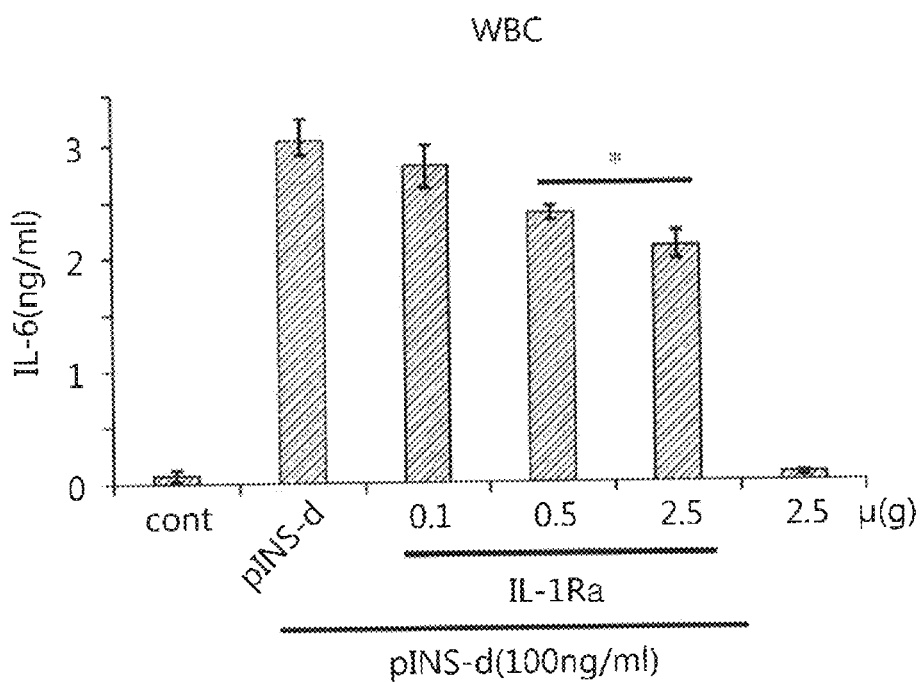
Figure 2D:
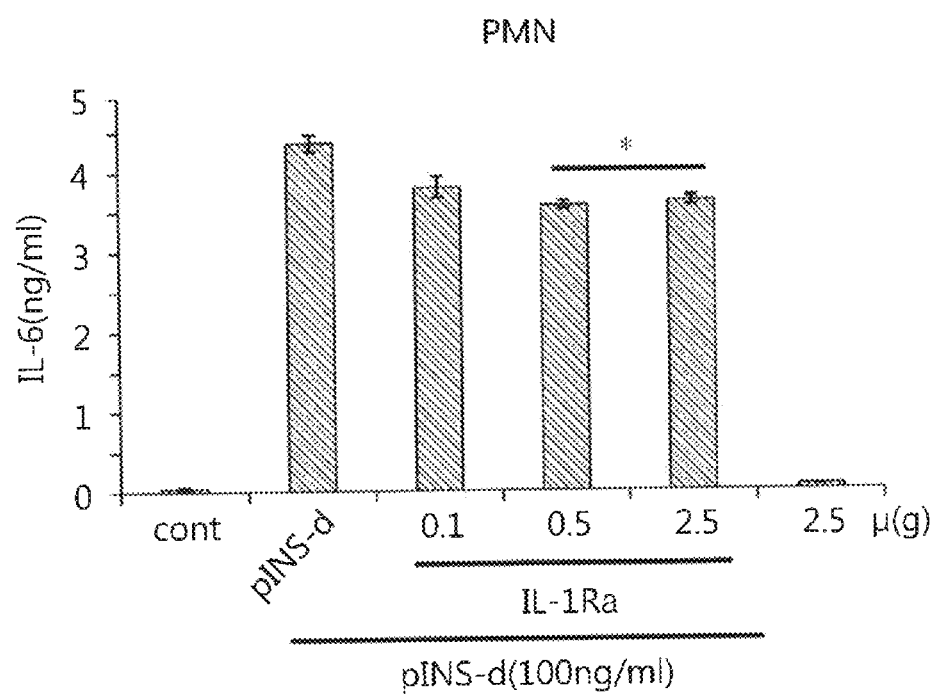
Figure 2E:
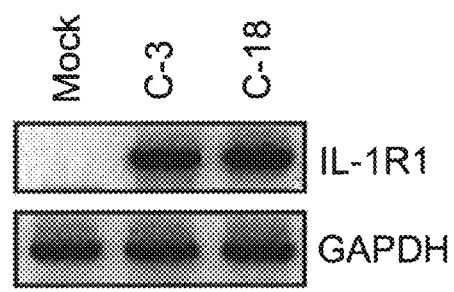
Figure 2F:
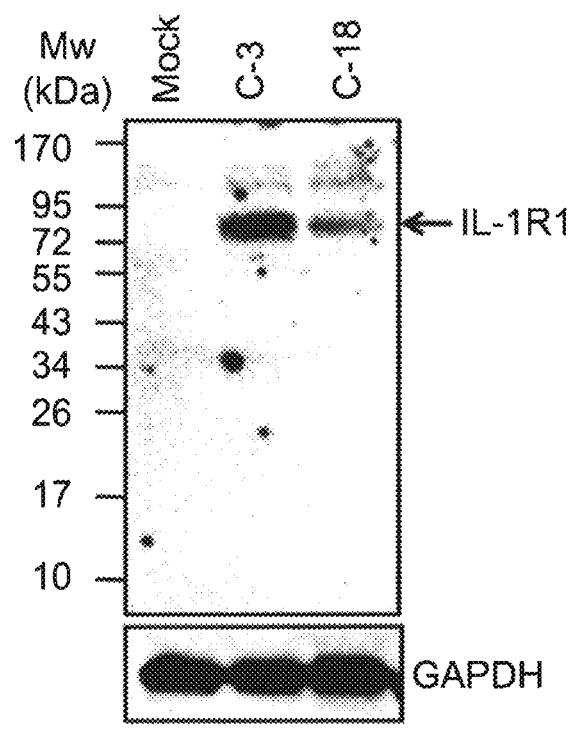
Figure 2G:
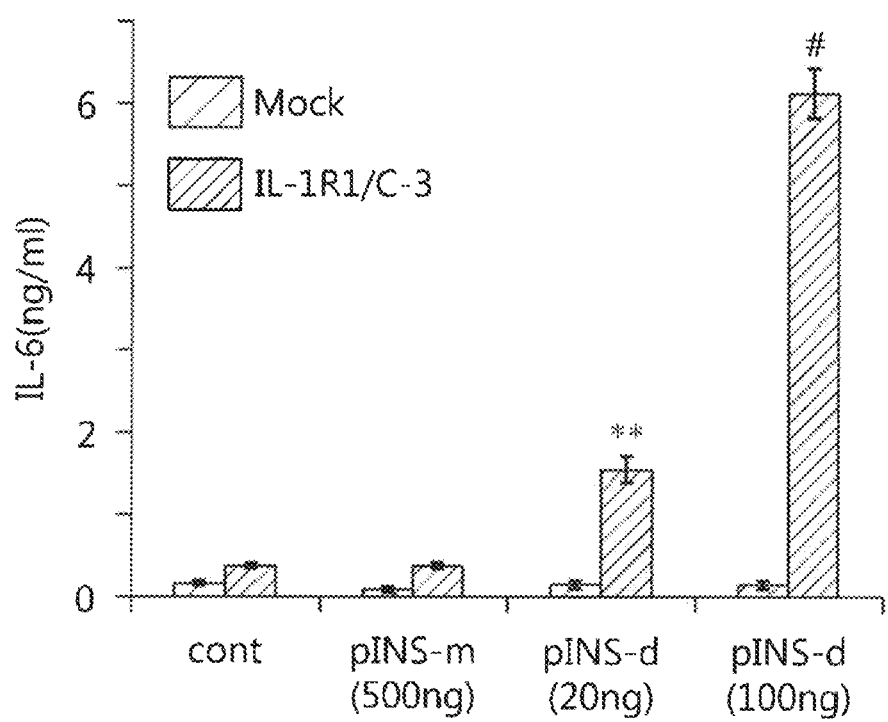
Figure 2H:
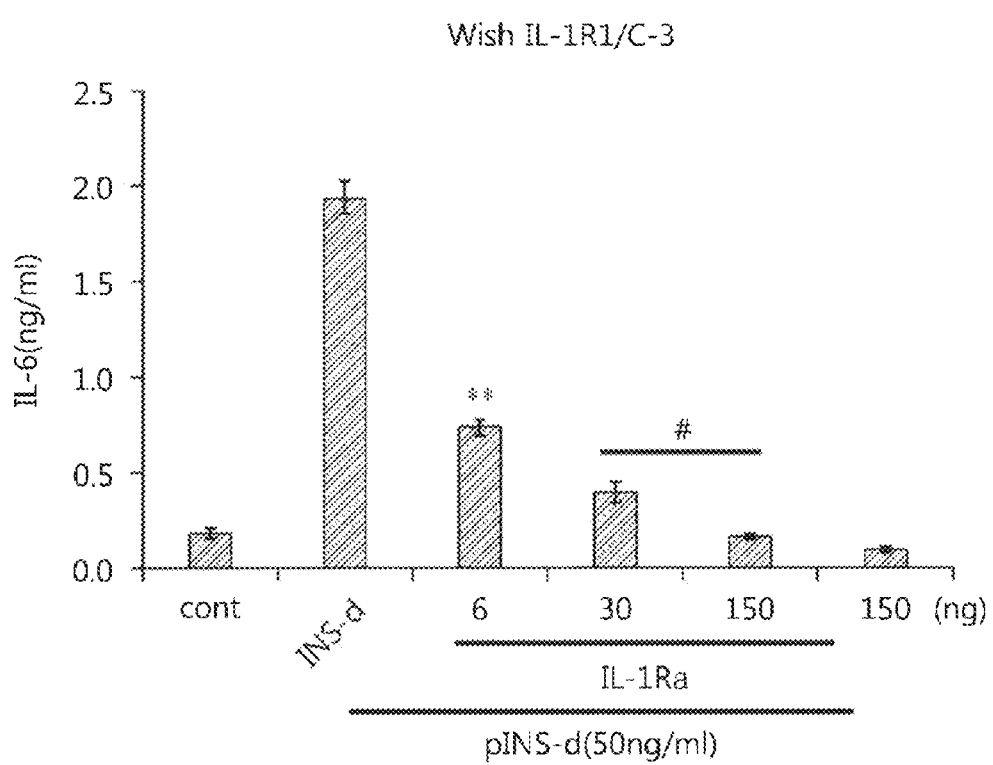
Figure 3A:
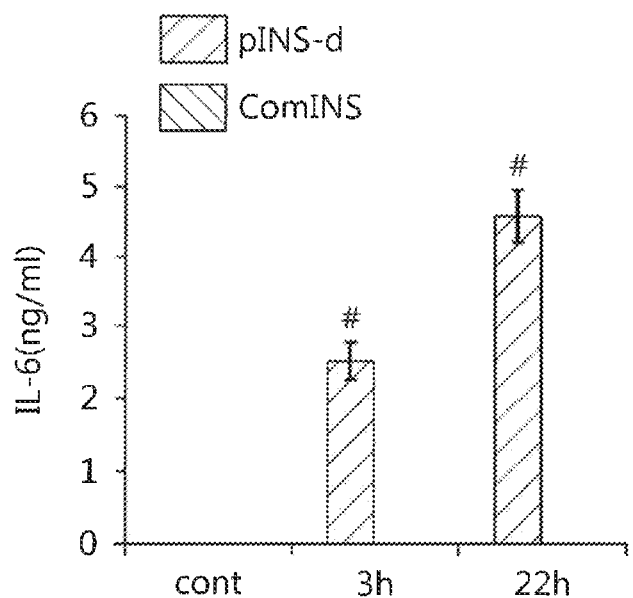
FIGS. 3A-3J illustrate that mAb anti-IL-1α recognized a motif in pINS-d.
Figure 3B:
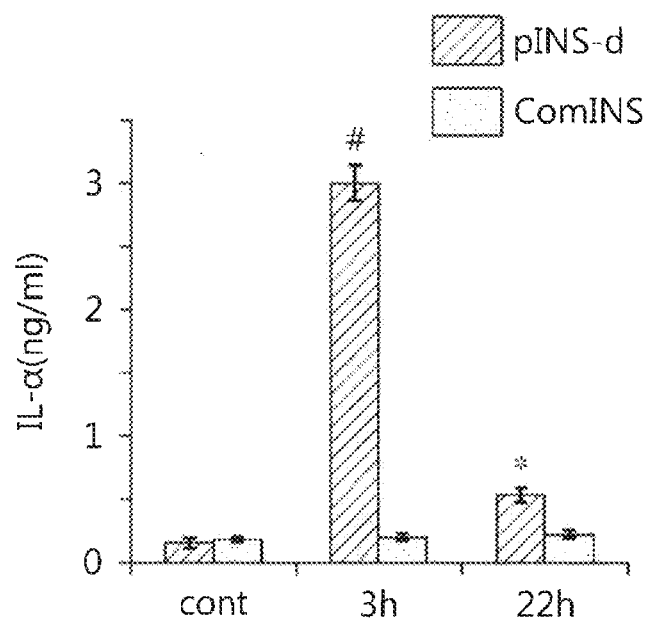
Figure 3C:
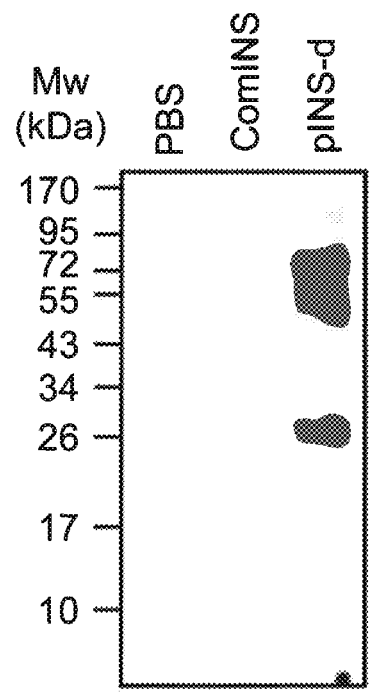
Figure 3D:
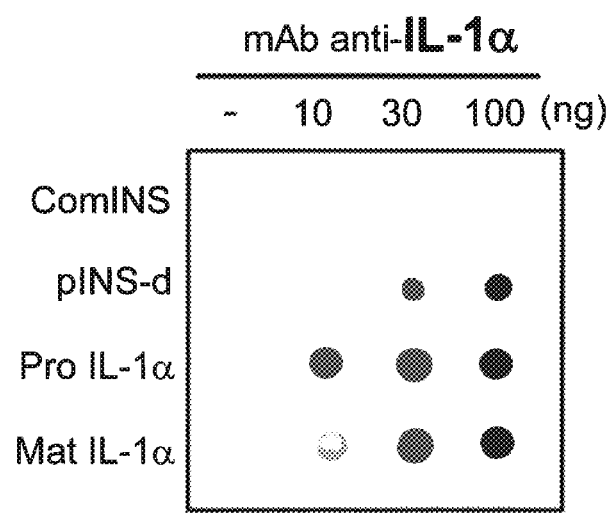
Figure 3E:
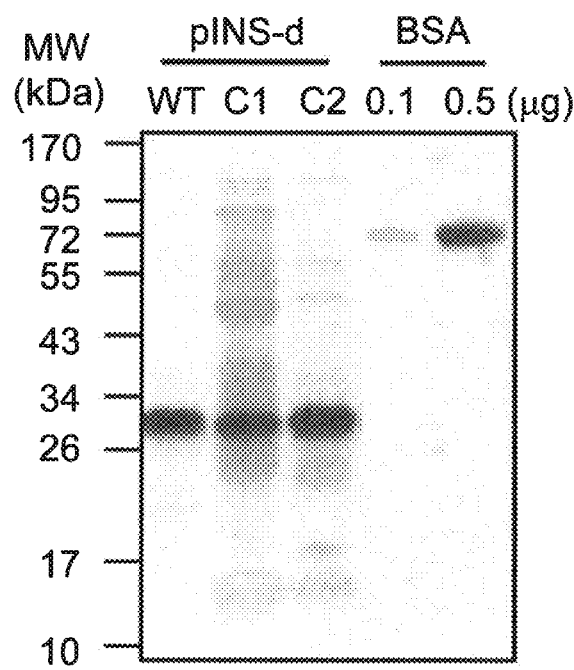
Figure 3F:
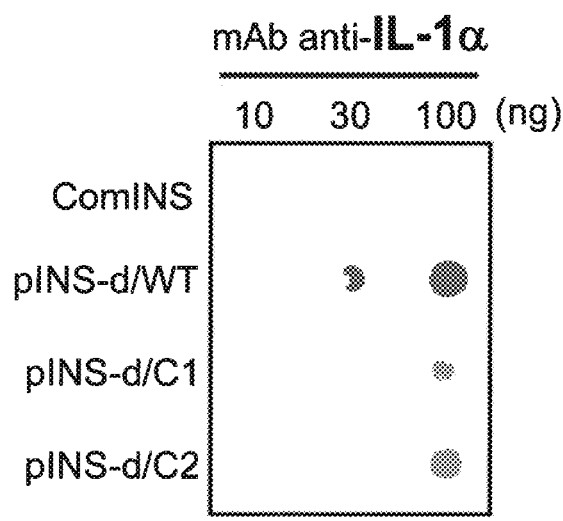
Figure 3G:
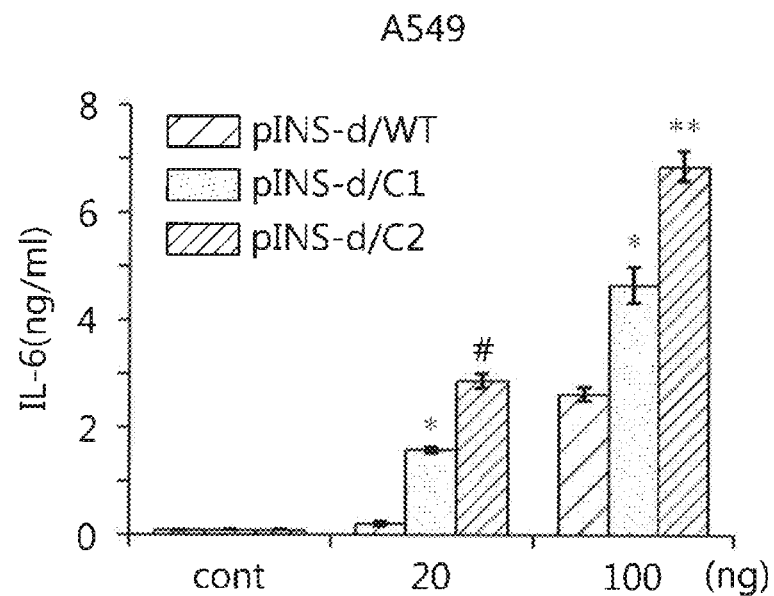
Figure 3H:
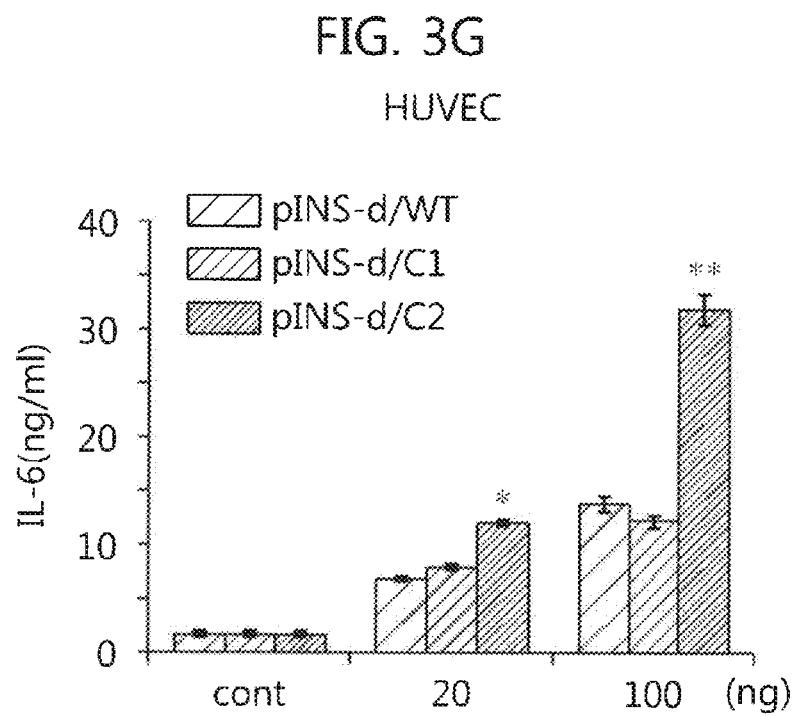
Figure 3I:
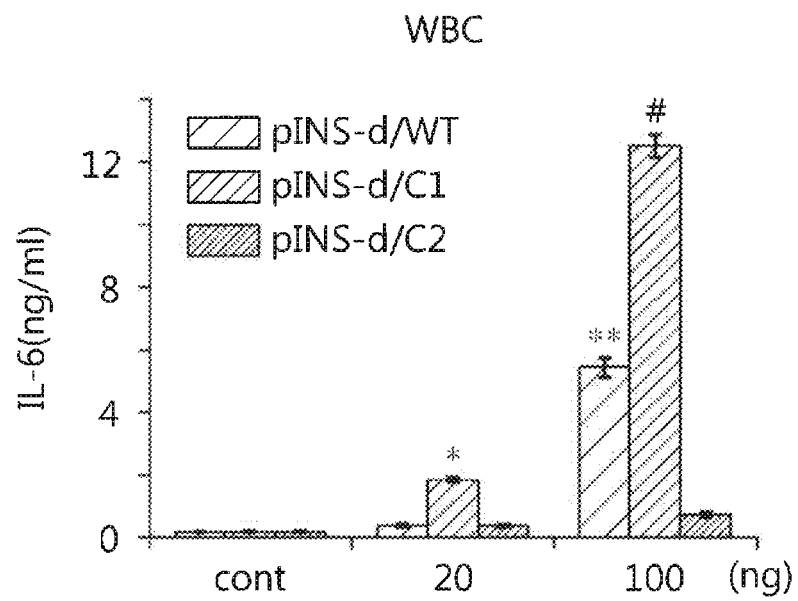
Figure 3J:
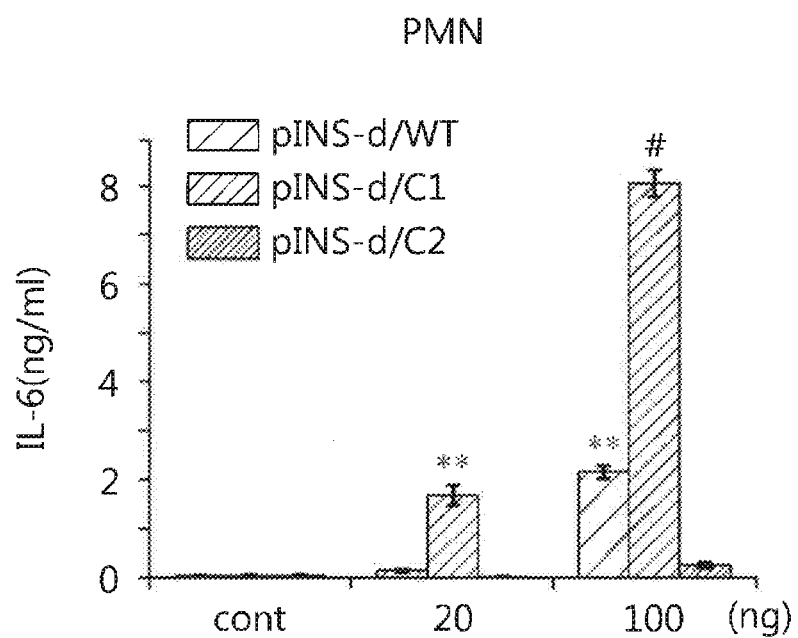
Figure 4A:
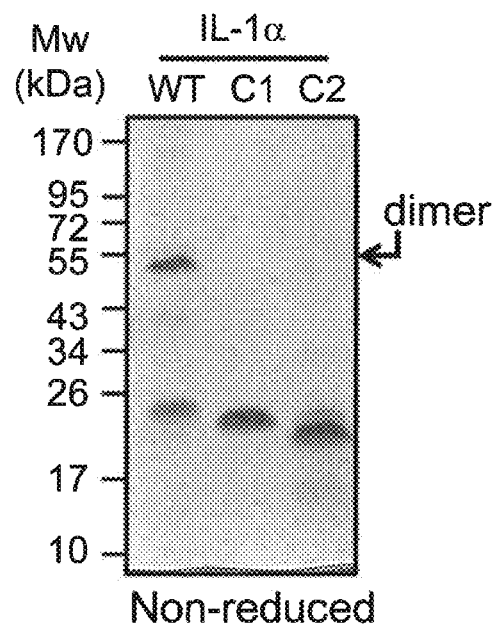
FIGS. 4A-4F illustrate generation and bioassay of the motif-deleted IL-1α mutants.
Figure 4B:
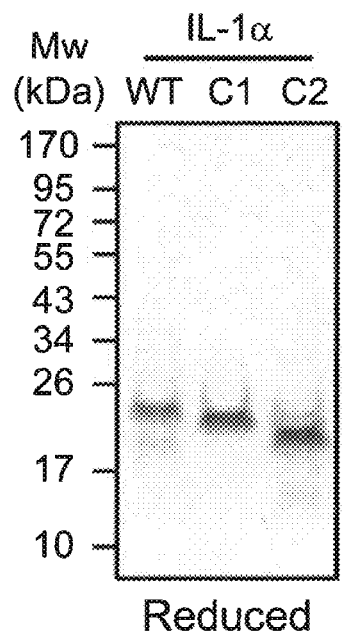
Figure 4C:
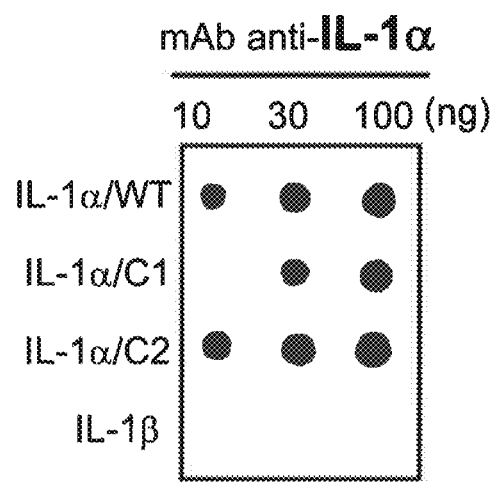
Figure 4D:
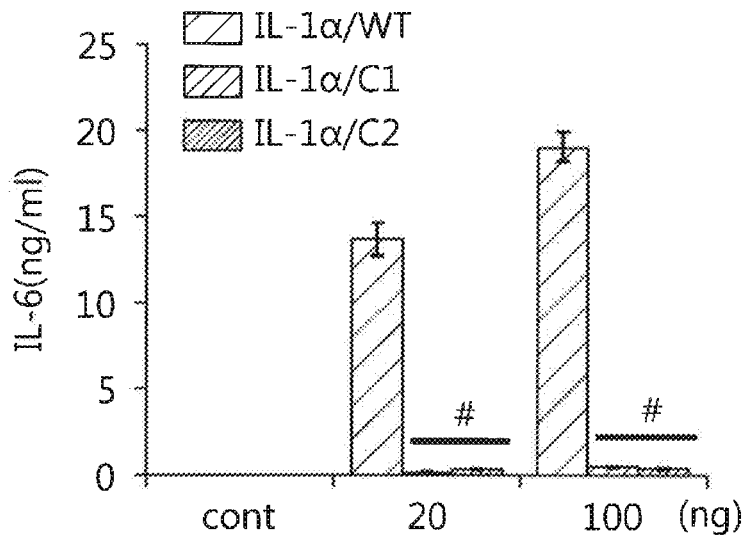
Figure 4E:
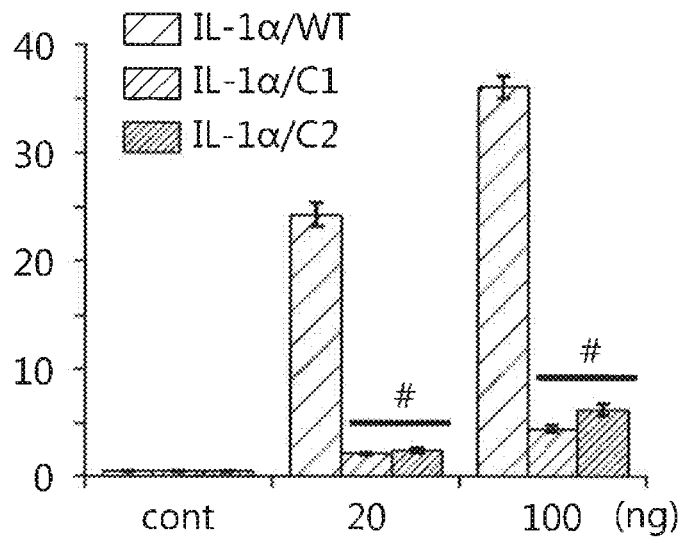
Figure 4F:
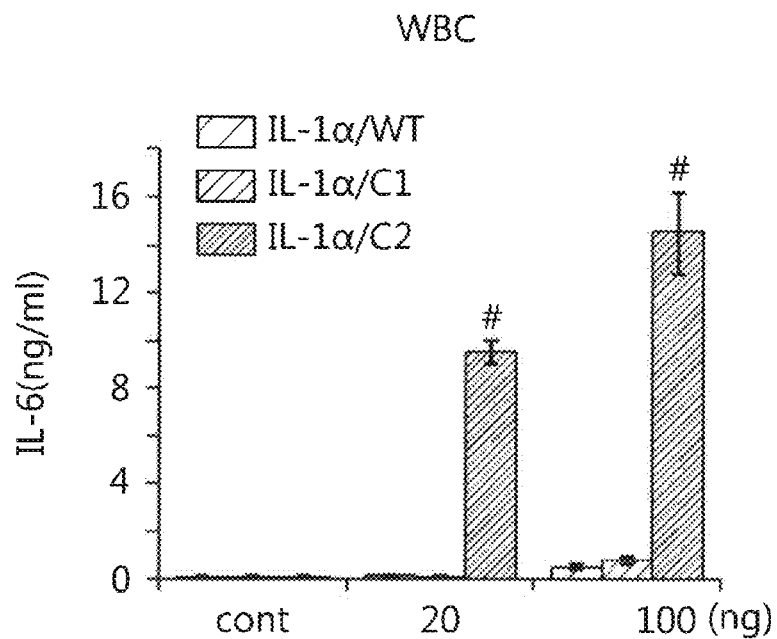
Figure 4G:
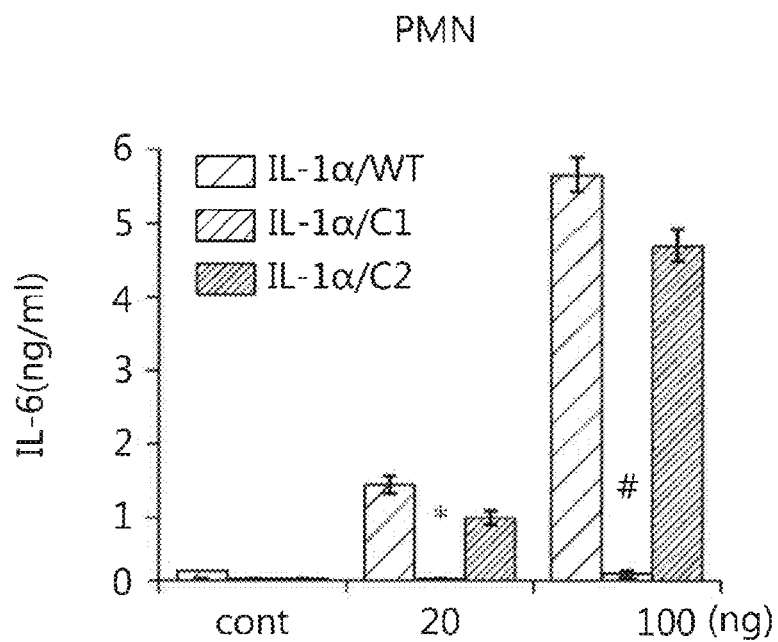
Figure 5A:
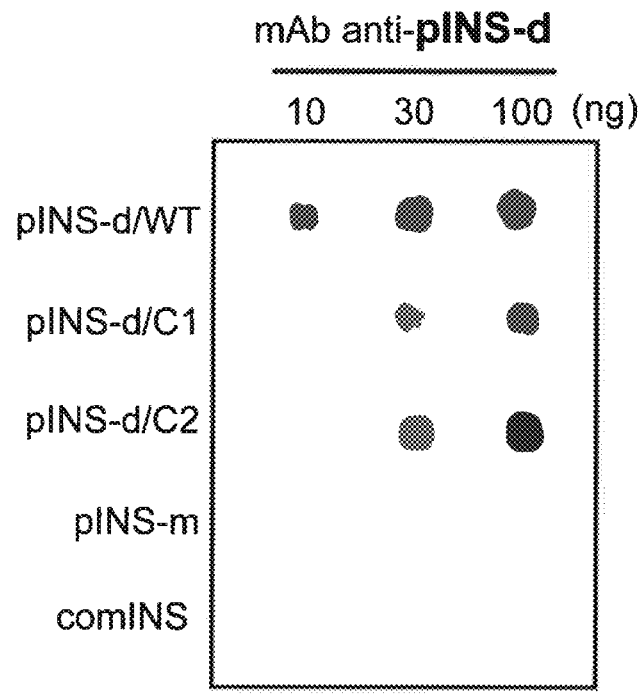
FIGS. 5A-5G illustrate mAb anti-pINS-d recognized IL-1α via an INS/IL-1α motif and exhibited an effect on pINS-d activity varying between cell types.
Figure 5B:
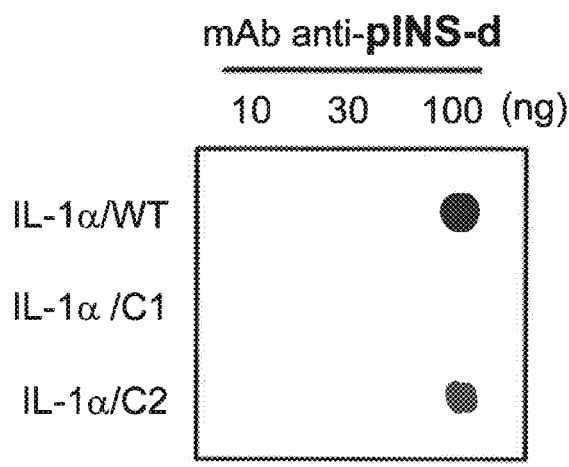
Figure 5C:
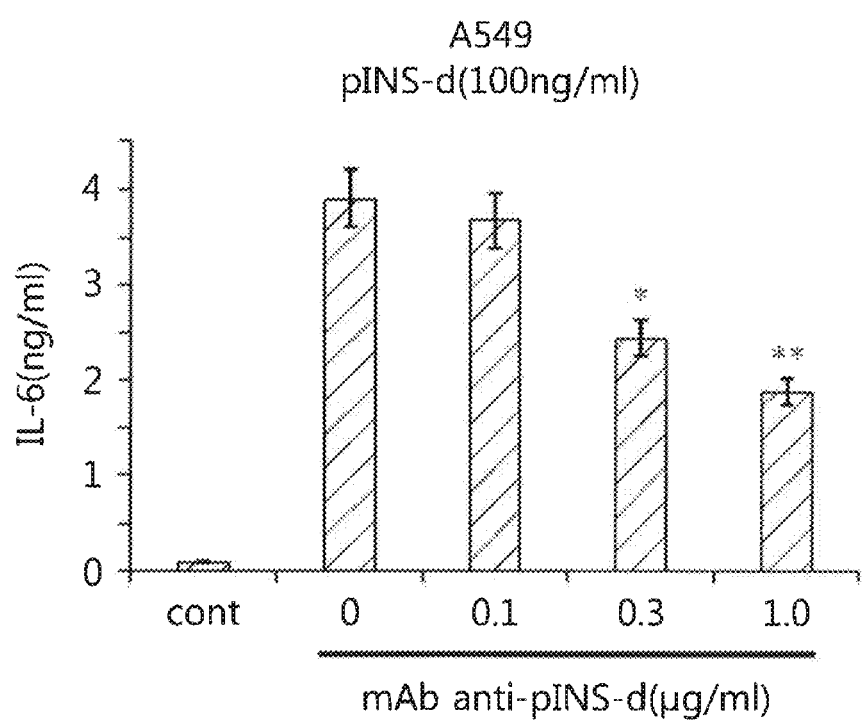
Figure 5D:
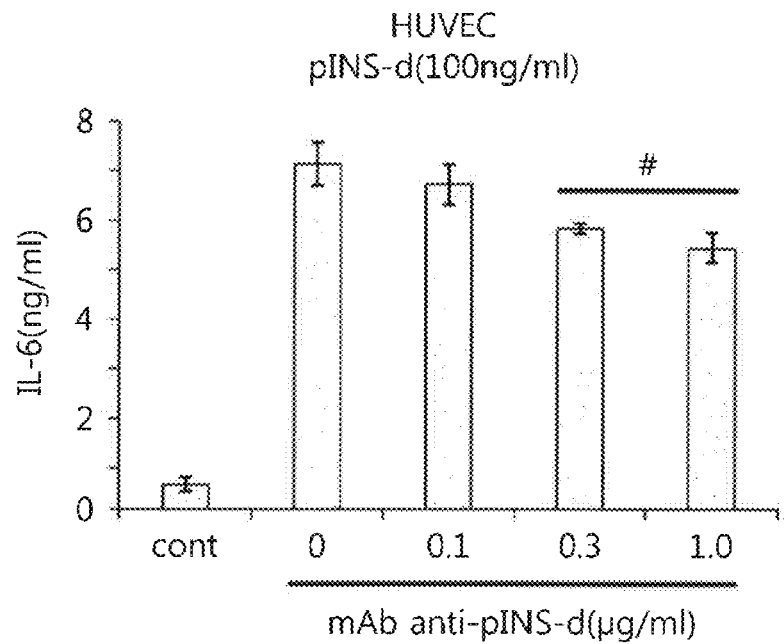
Figure 5E:
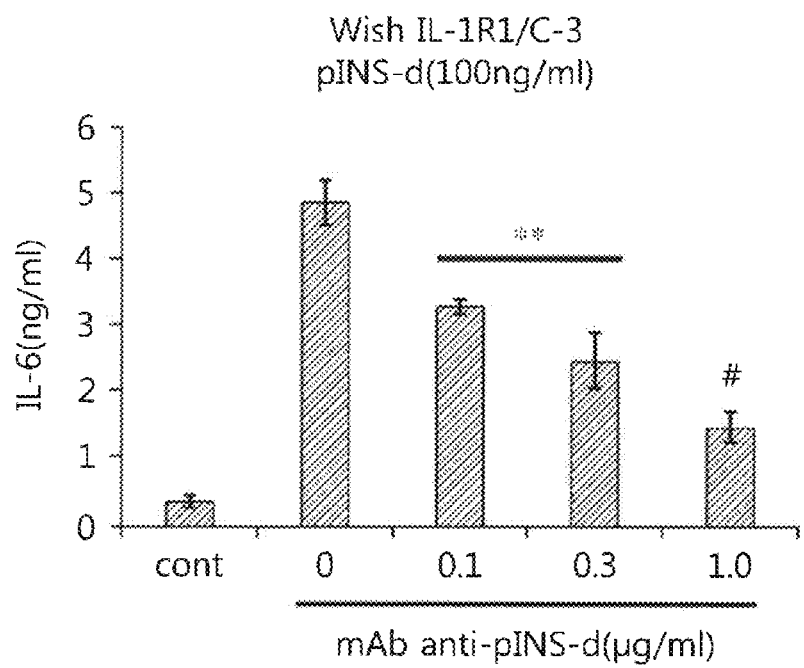
Figure 5F:
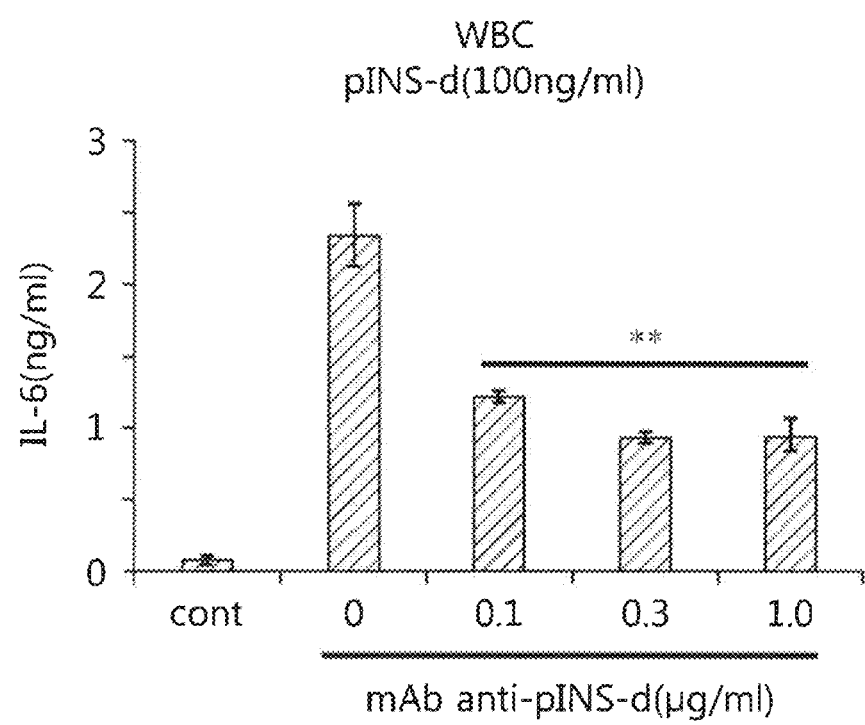
Figure 5G:
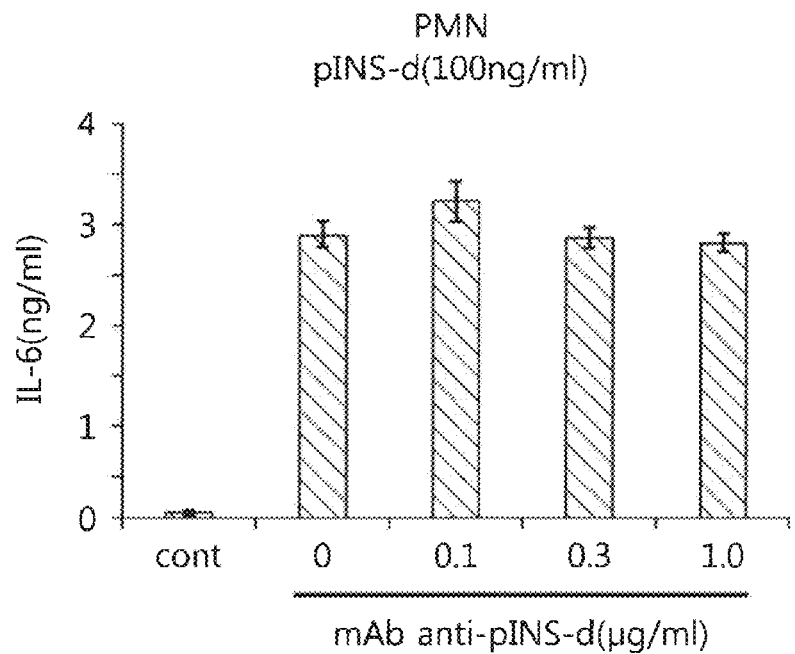
Figure 6A:
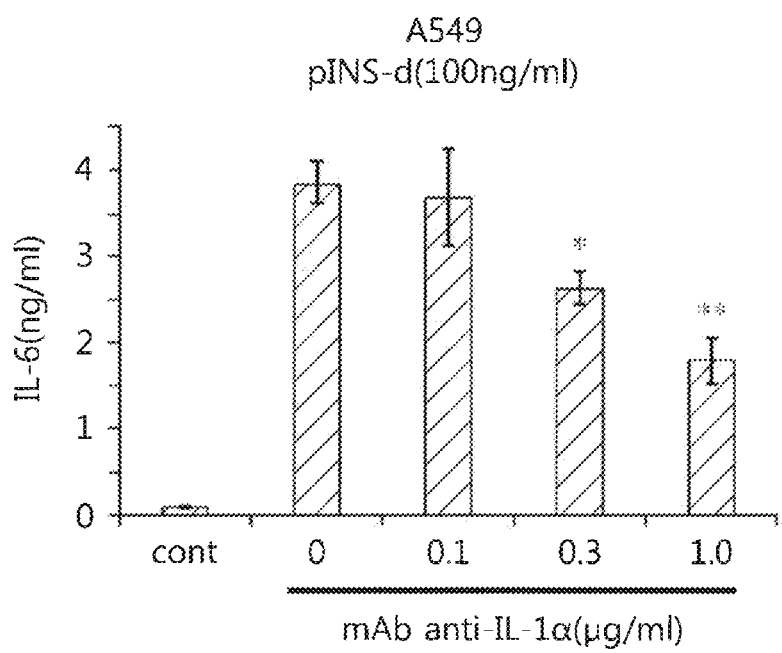
FIGS. 6A-6E illustrate suppression of pINS-d induced IL-6 by mAb anti-IL-1α.
Figure 6B:
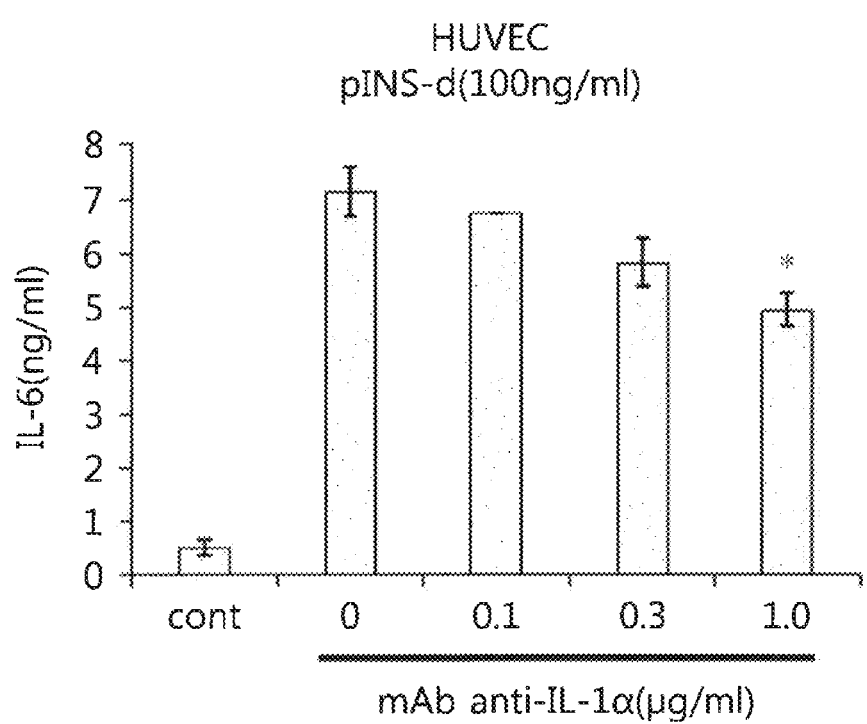
Figure 6C:
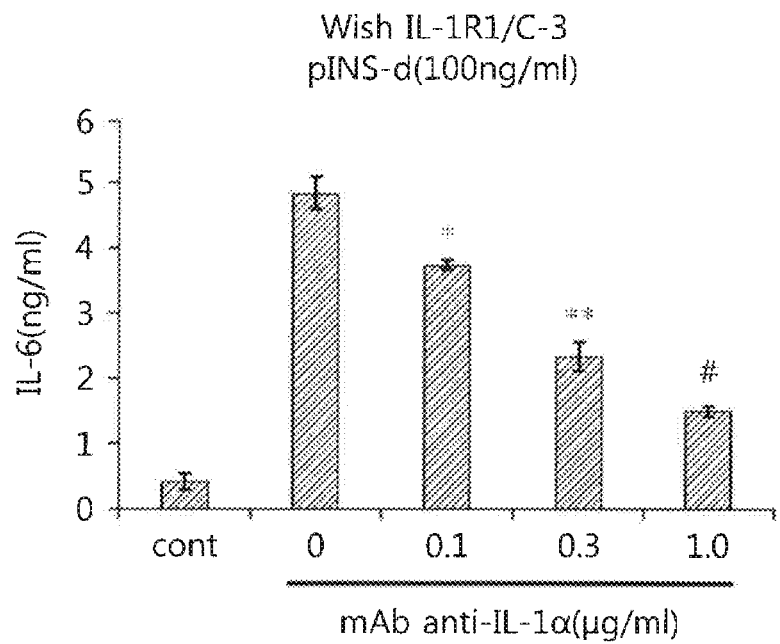
Figure 6D:
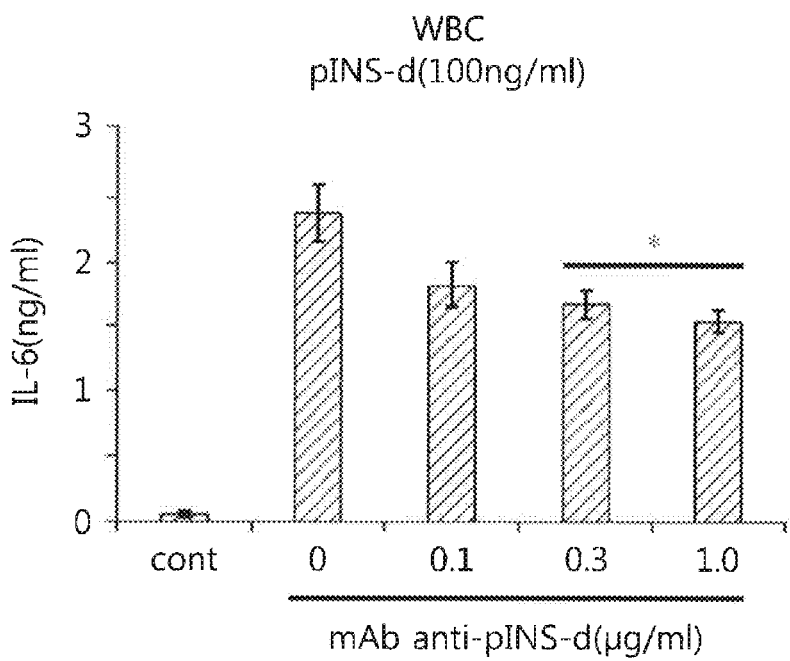
Figure 6E:
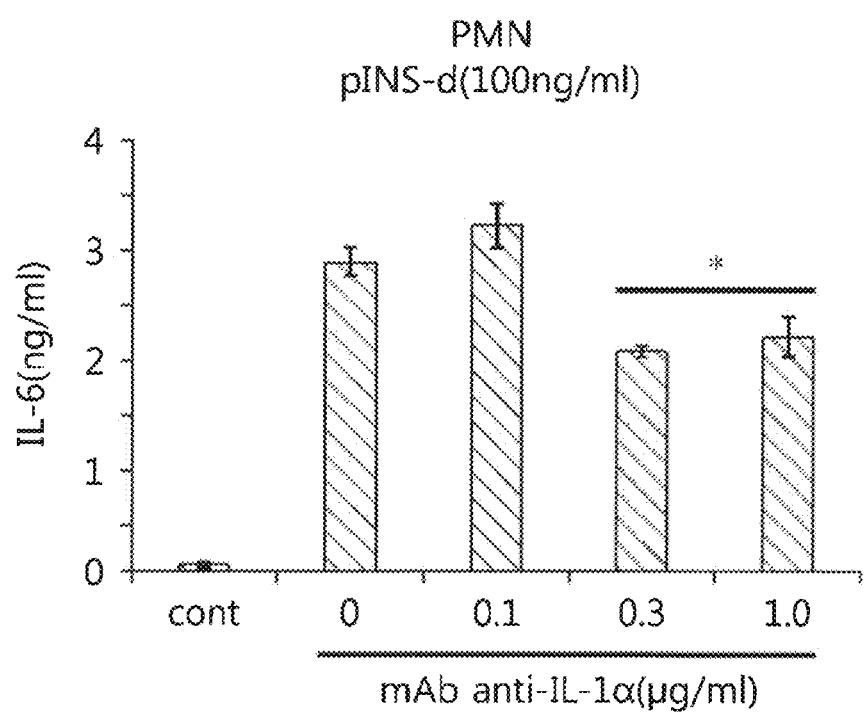
Figure 7A:
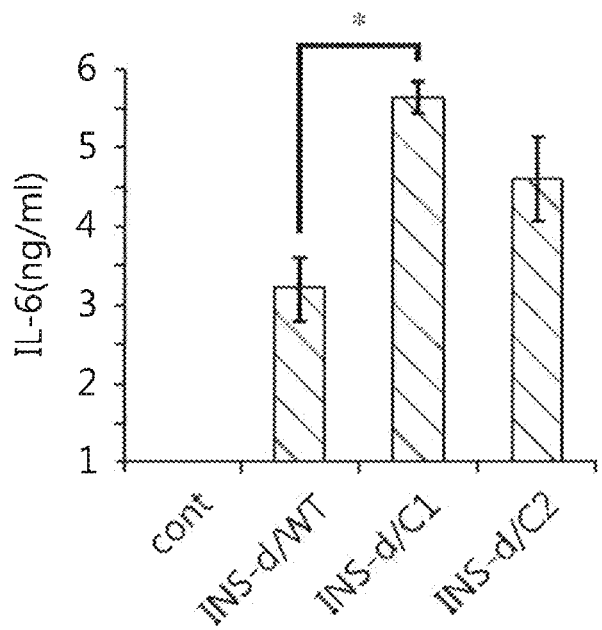
FIGS. 7A-7K illustrate an in vivo experiment of pINS-d with IL-1R1 deficient mice.
Figure 7B:
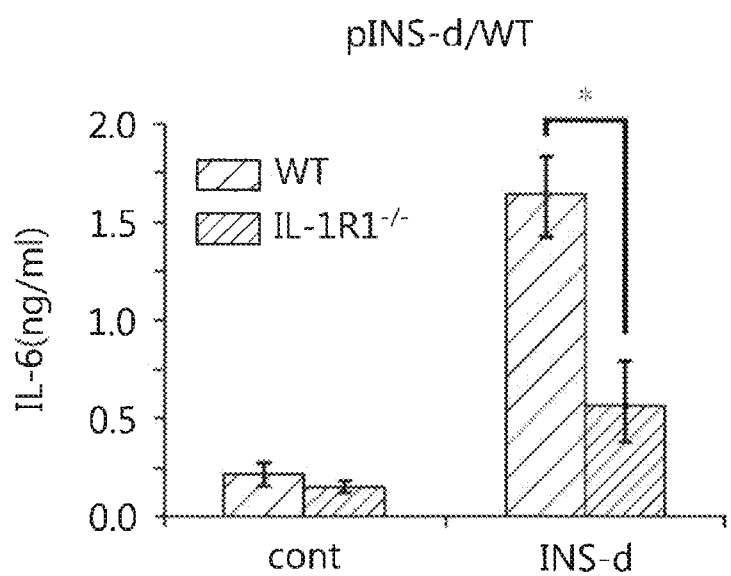
Figure 7C:
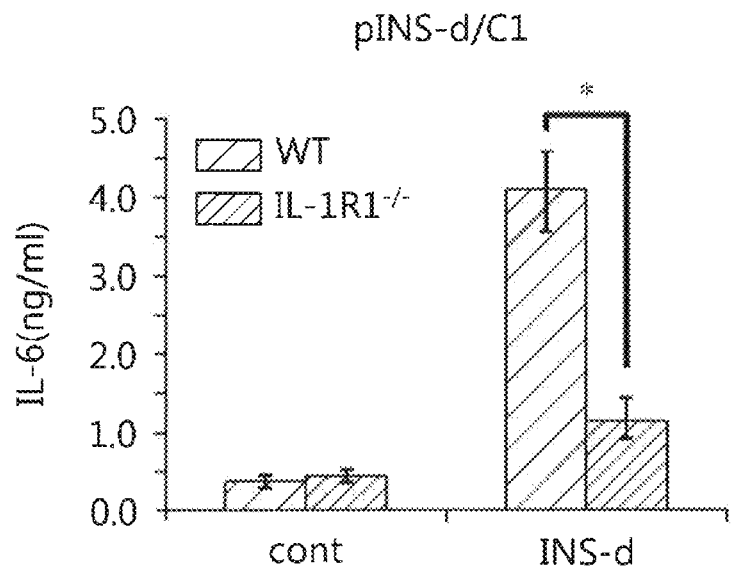
Figure 7D:
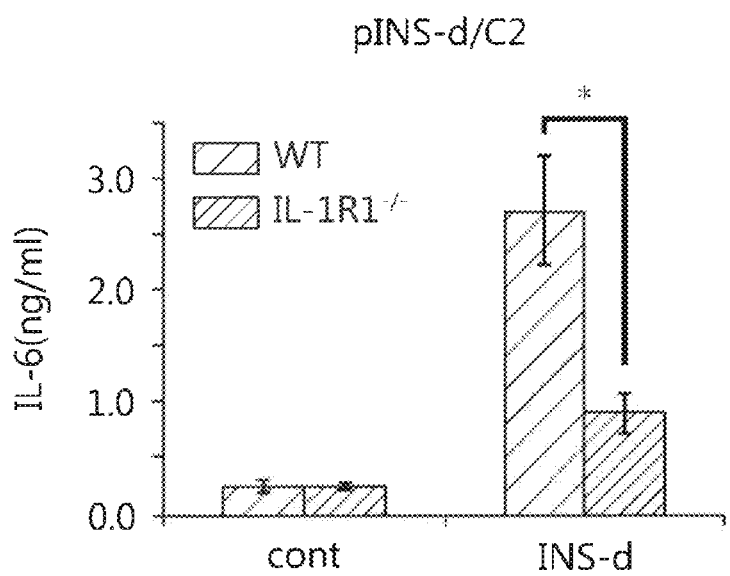
Figure 7E:
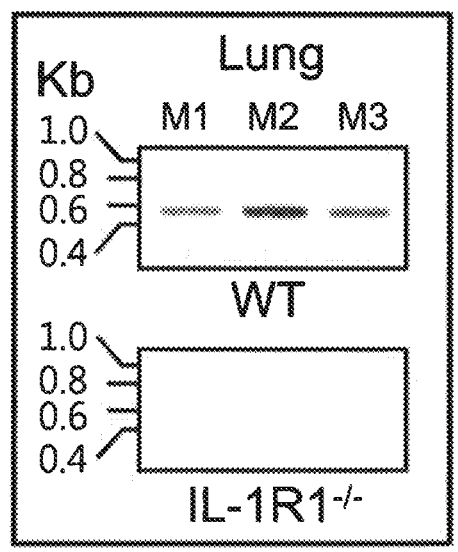
Figure 7F:
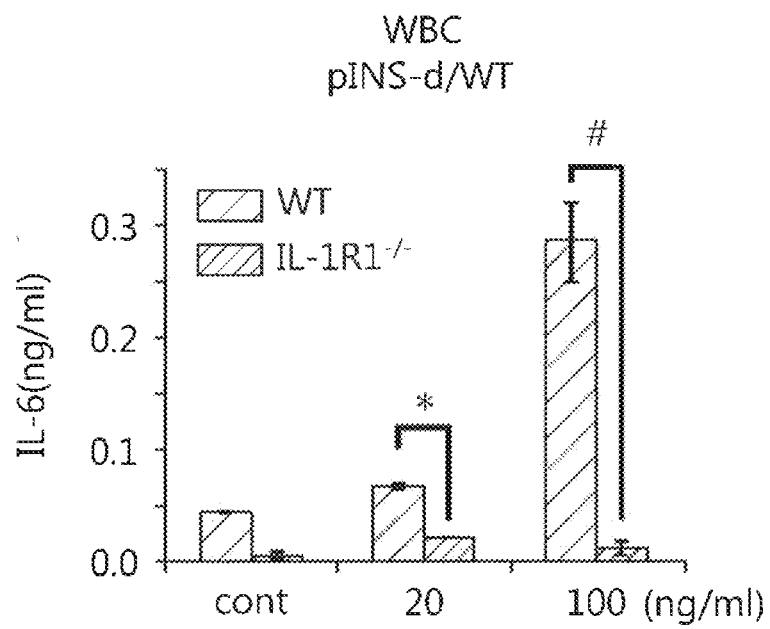
Figure 7G:
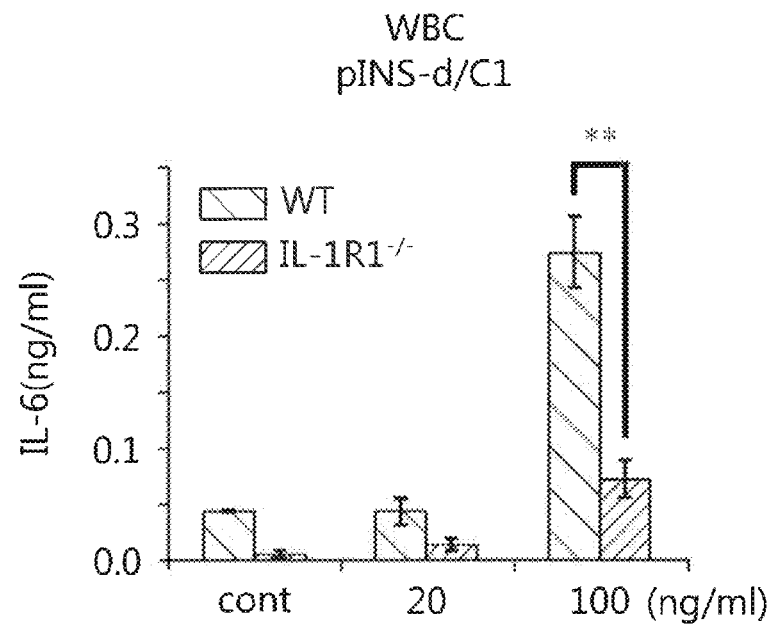
Figure 7H:
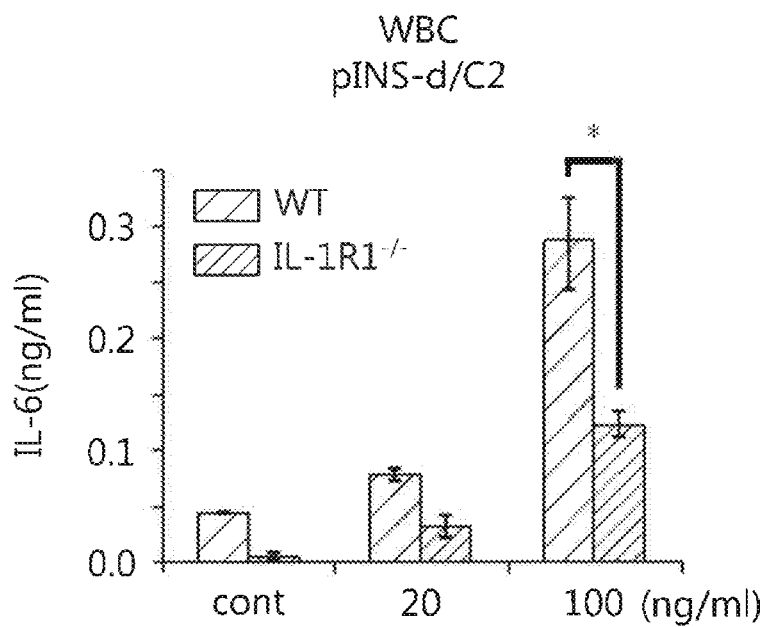
Figure 7I:
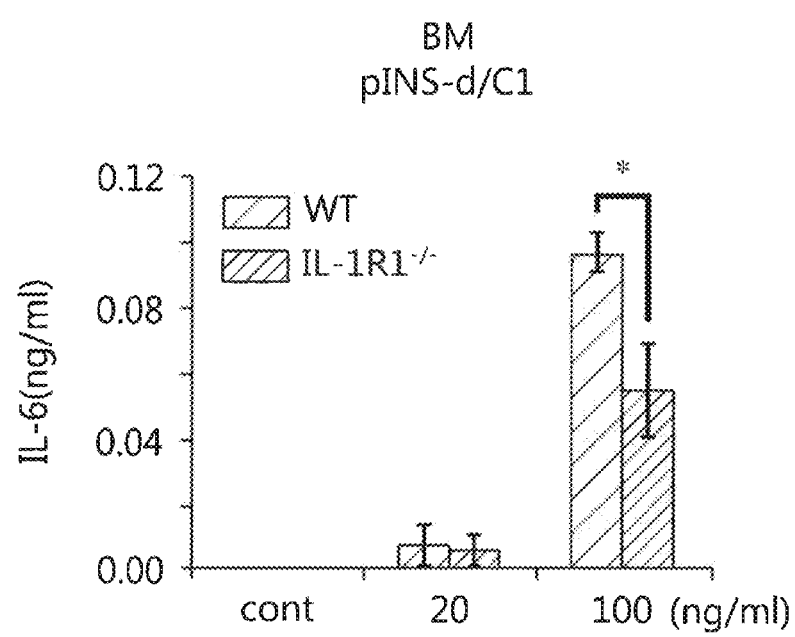
Figure 7J:
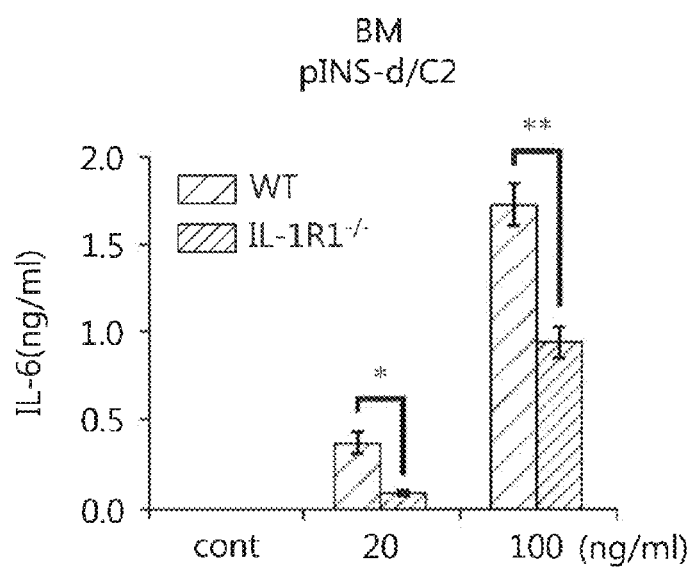
Figure 7K:
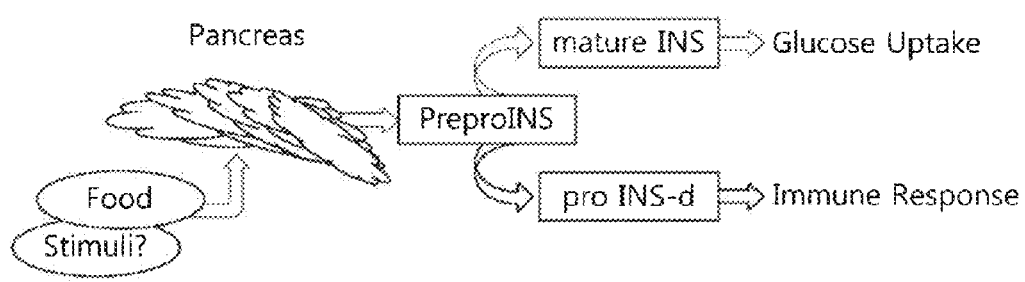
Figure 8A:
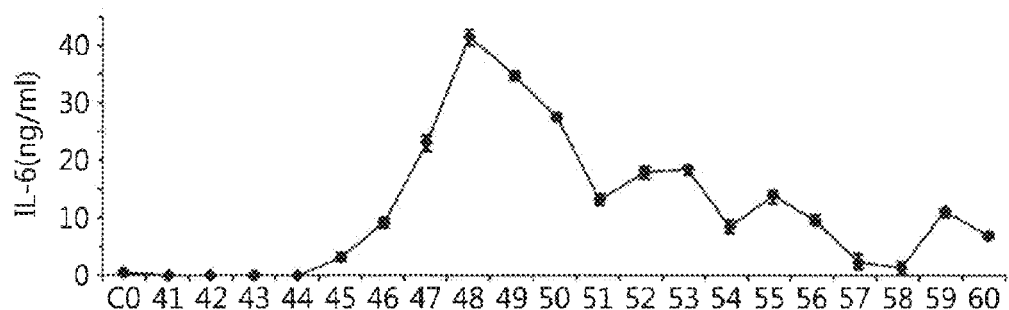
FIGS. 8A-8I show biological activity of pINS and HPLC purified pINS in silver staining.
Figure 8B:
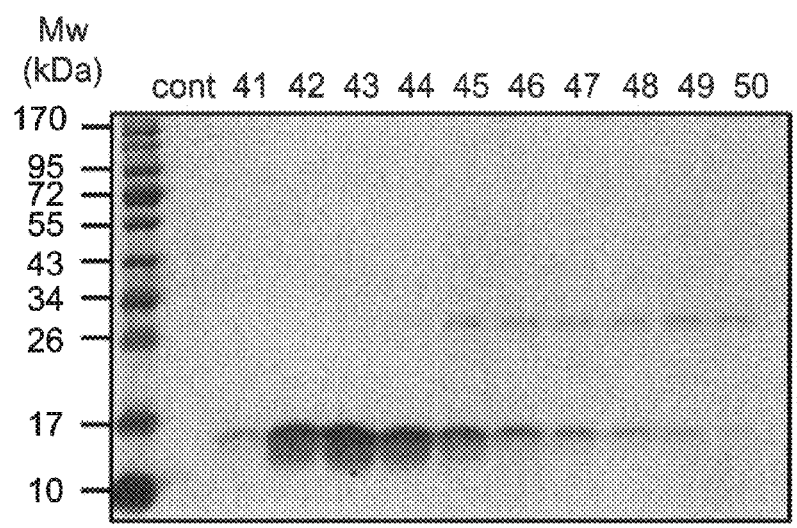
Figure 8C:
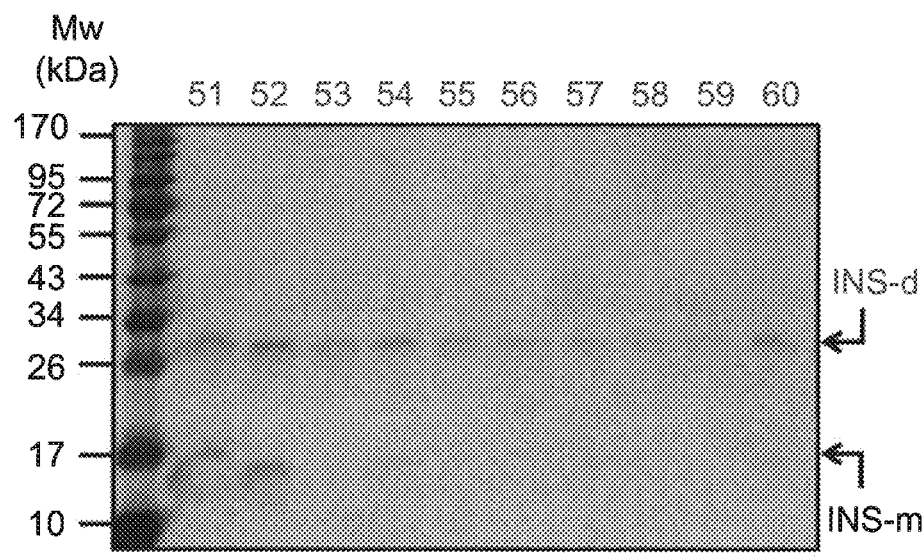
Figure 8D:
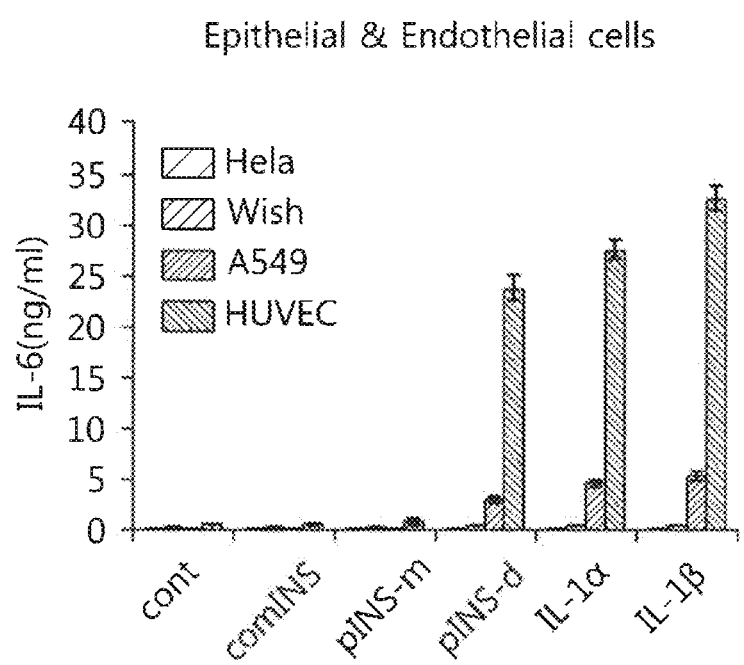
Figure 8E:
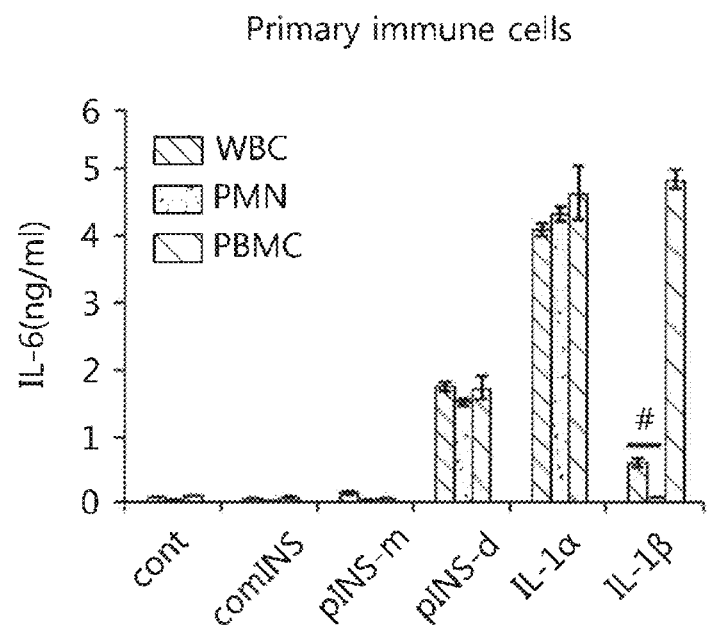
Figure 8F:
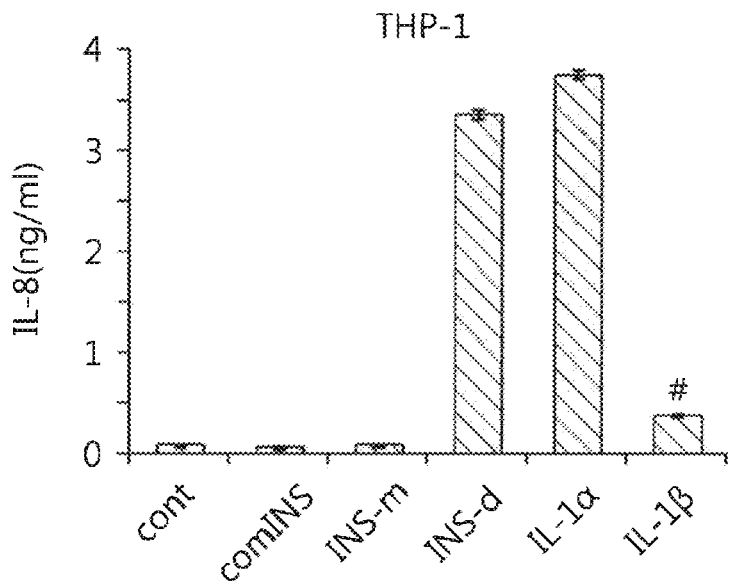
Figure 8G:
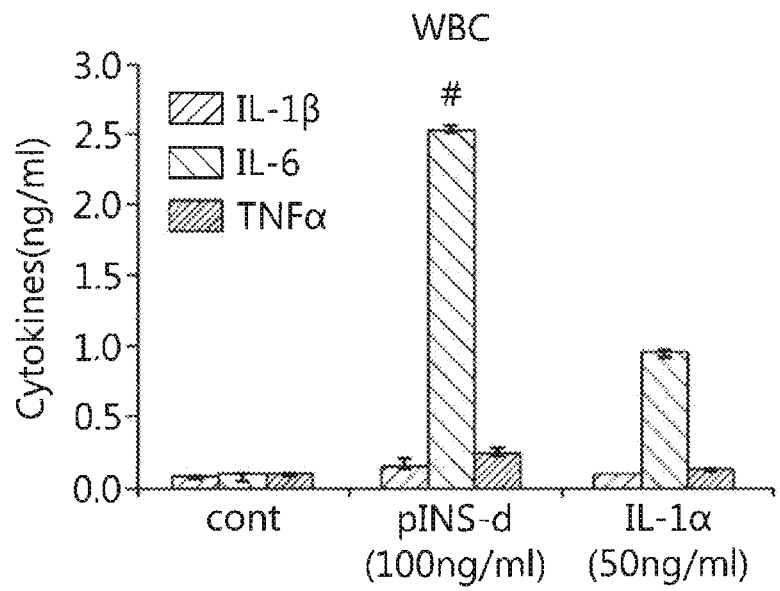
Figure 8H:
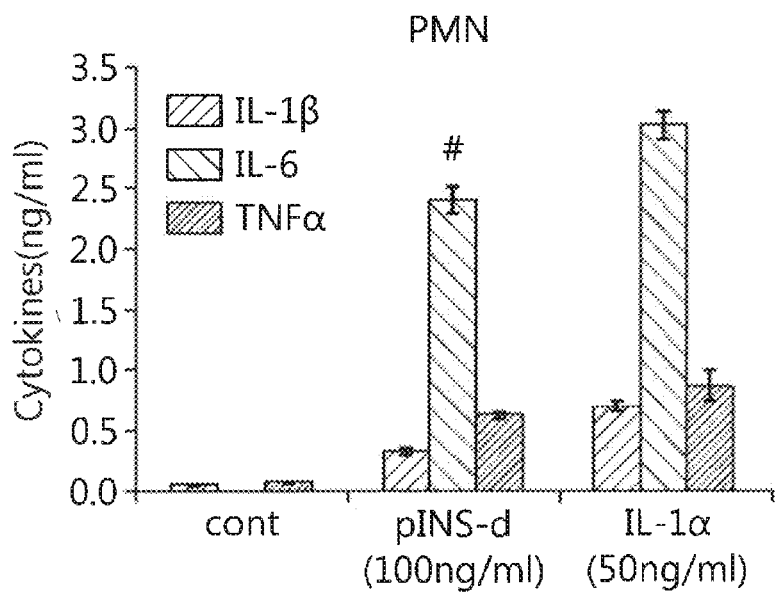
Figure 8I:
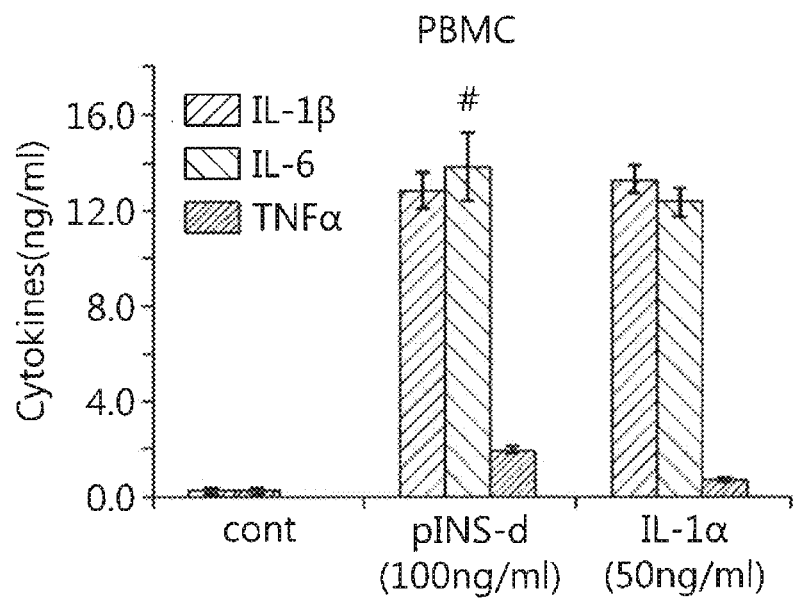
Figure 9A:
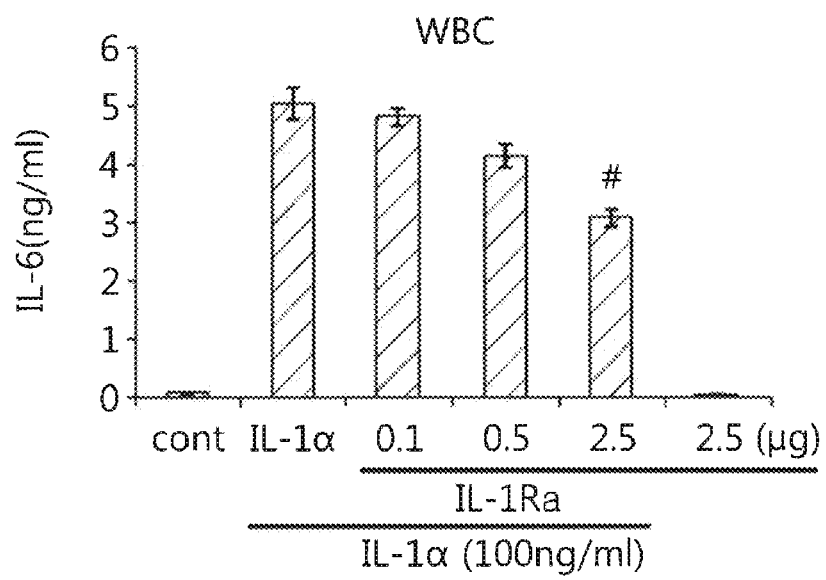
FIGS. 9A-9D illustrate the inhibitory effect of IL-1Ra on IL-1α and IL-1β-induced cytokine production.
Figure 9B:
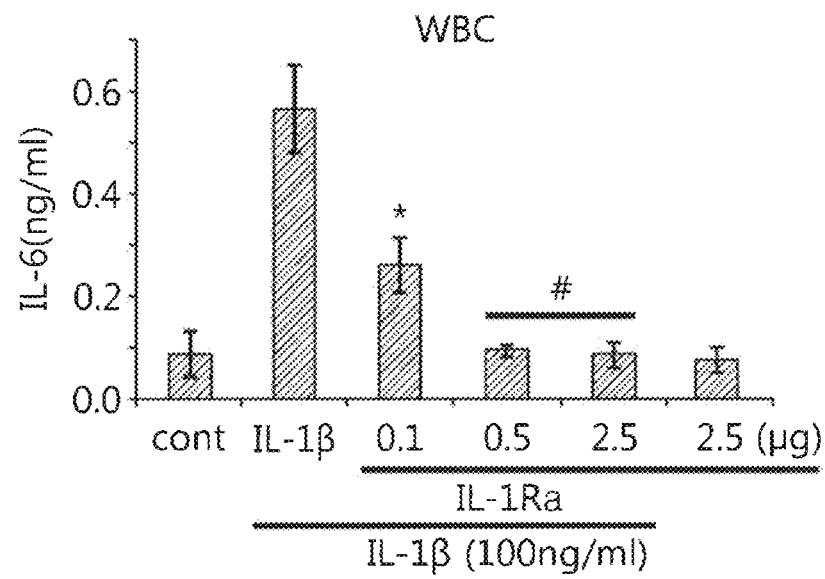
Figure 9C:
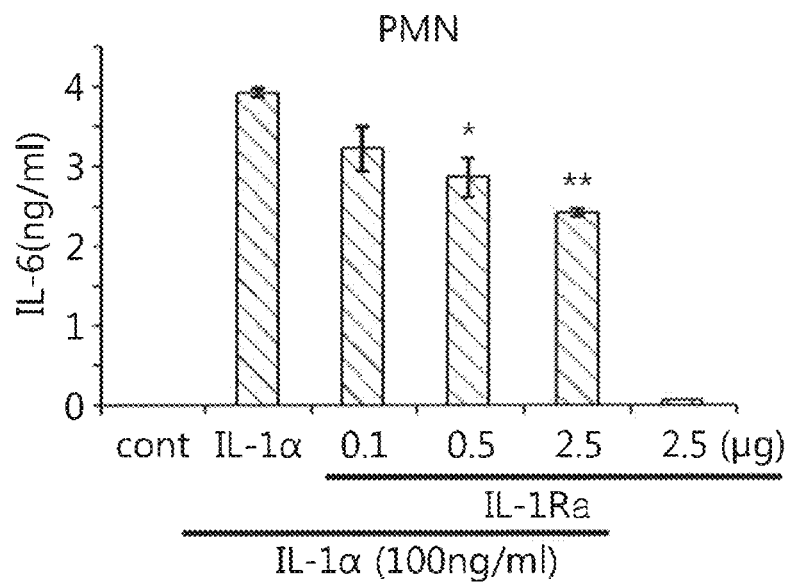
Figure 9D:
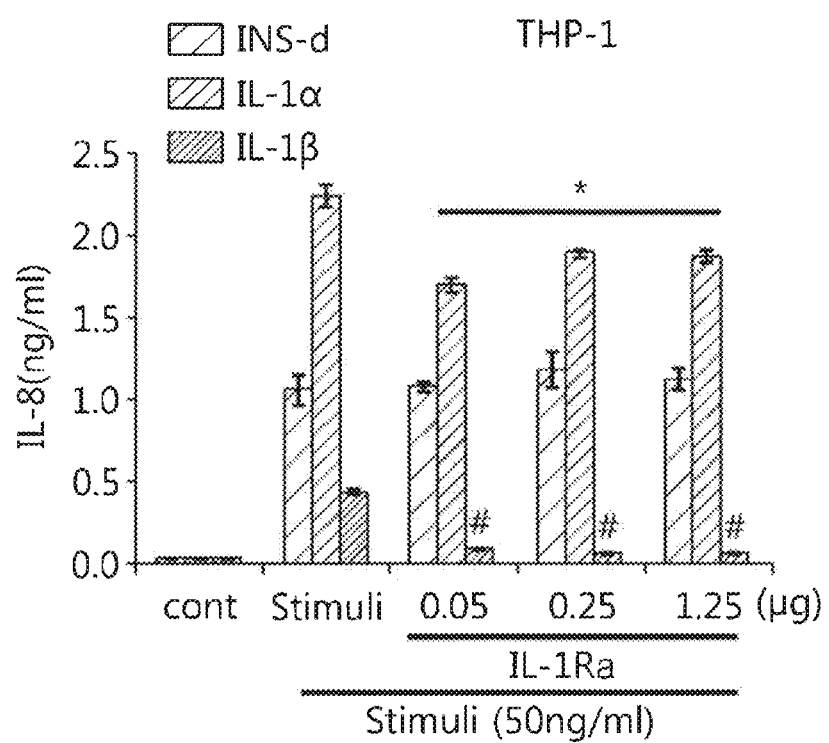

Example 3: Expression of Recombinant Protein pINS/WT, pINS/C1, and pINS/C2 lacking the signal peptide of 24 amino acid residues at the N-terminus as well as mature IL-1α/WT, IL-1α/C1, and IL-1α/C2 were expressed in *E. coli*. The inventors of the present disclosure used BL21-CodonPlus competent cells from Agilent Technologies (Santa Clara, Calif.). The inventors of the present disclosure purified the recombinant proteins from the inclusion body lysing with urea (8 M) in a phosphate buffer of pH 8. The supernatant of the recombinant protein was passed through a mini-Talon column and eluted with imidazole (0.3 M). The eluted fractions were directly applied to high-performance liquid chromatography (HPLC). The peaks of each fraction (OD 280 nm) were visualized with silver staining (FIG. 8B/C), but peaks of IL-1α proteins are not shown. Human IL-1Ra, mouse IL-1α, and IL-1β were expressed as described in Kim, B. et al., *Front Immunol* 4, 391 (2013). Similarly sized bands were pooled and lyophilized for further testing on purity and quantity evaluation. Only qualified batches of recombinant protein were kept for use in the in vitro and in vivo experiments. The comINS was obtained from Green Cross (Kyeonggi-do, Korea).

Example 4: Cell Line and Overexpression for IL-1R1

Figure 10A:
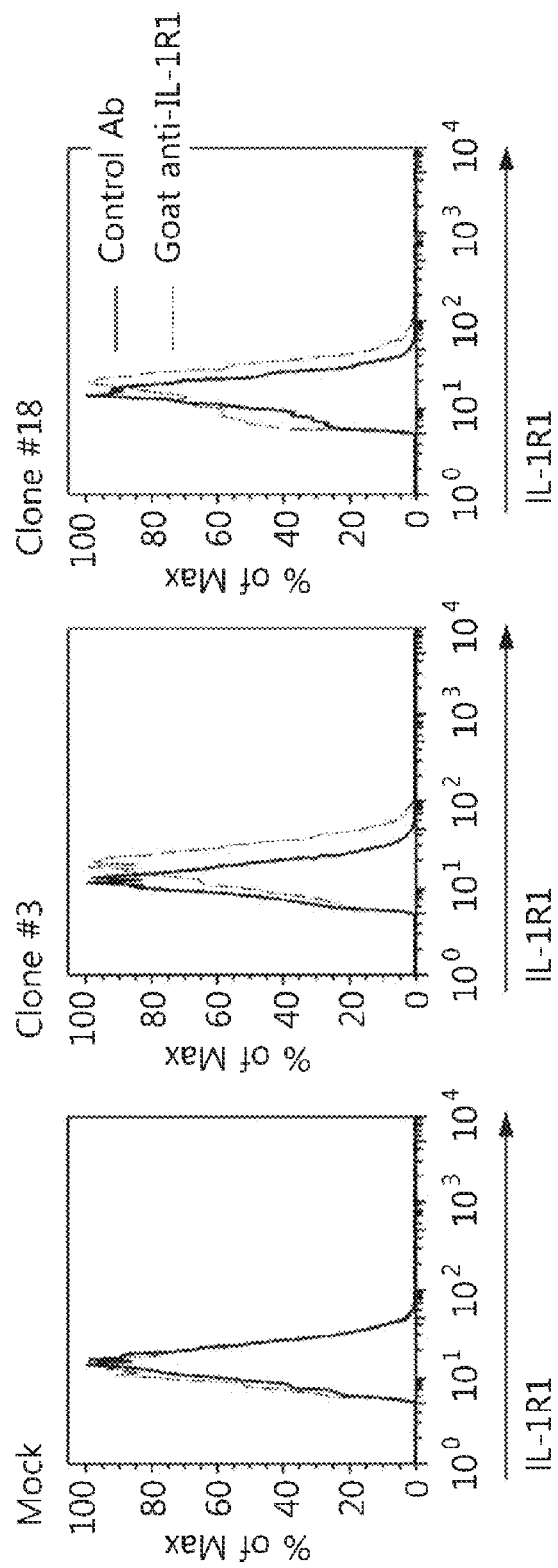
FIGS. 10A-10D illustrate expression and reconstitution of IL-1R1 on Wish cells.
Figure 10B:
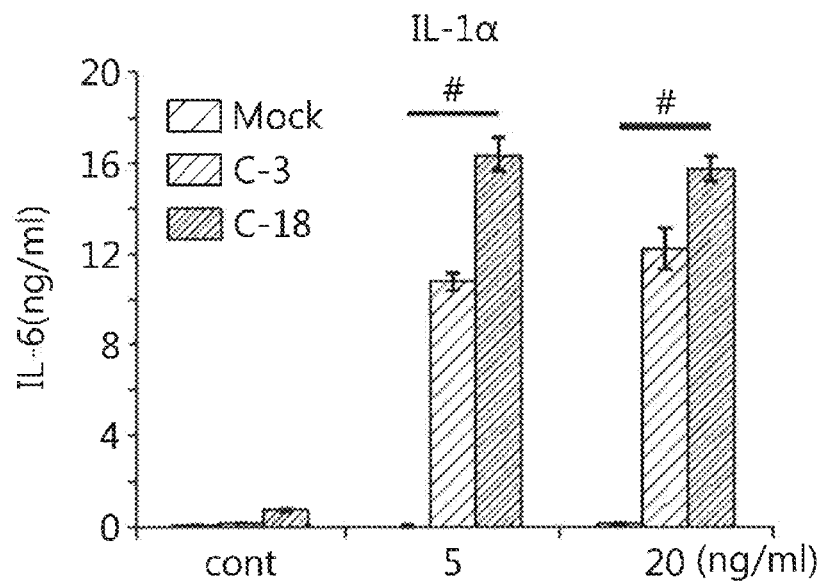
Figure 10C:
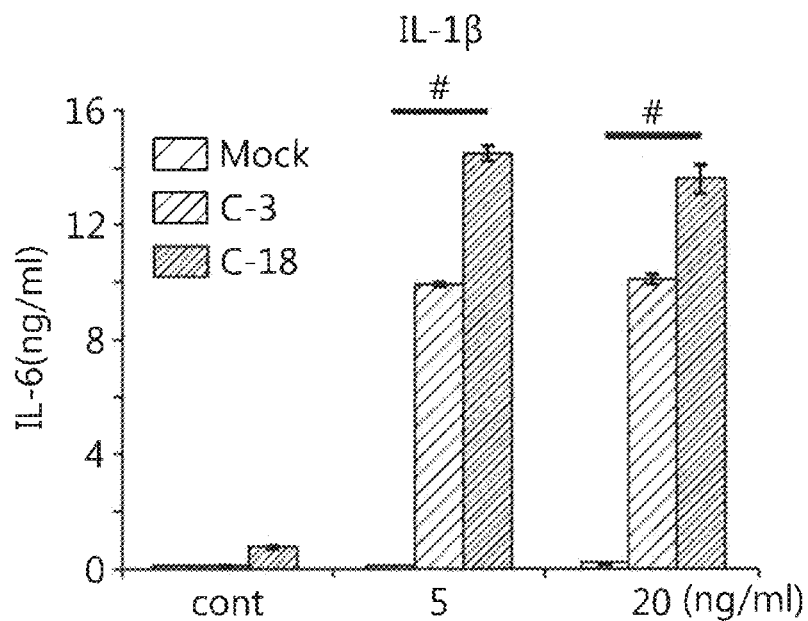
Figure 10D:
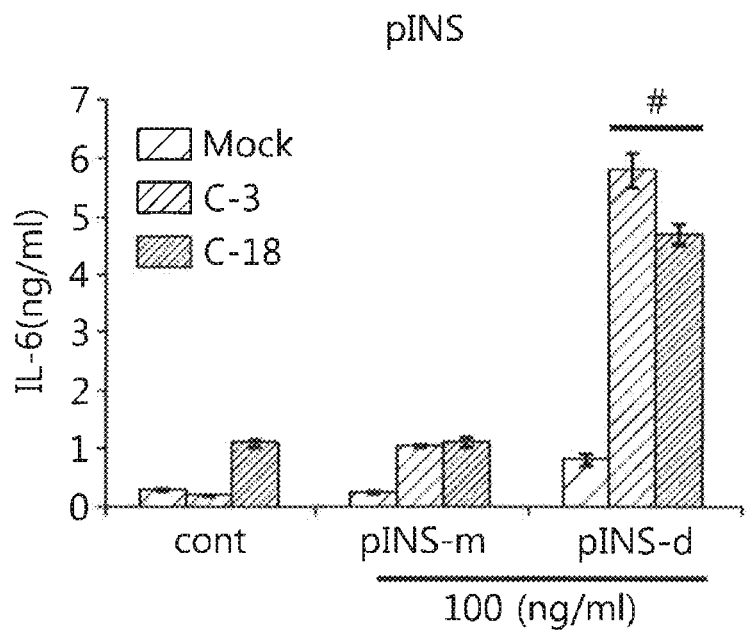
Figure 11A:
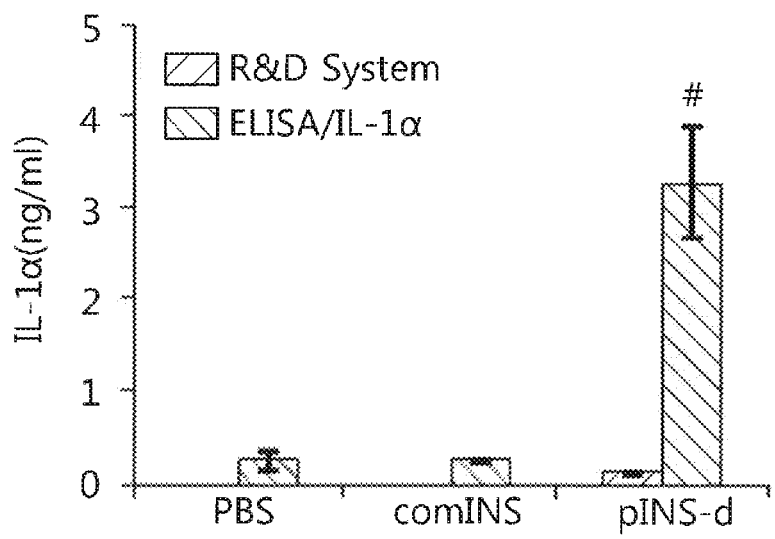
FIGS. 11A-11C illustrate that anti-IL-1α mAb recognized pINS-d.
Figure 11B:
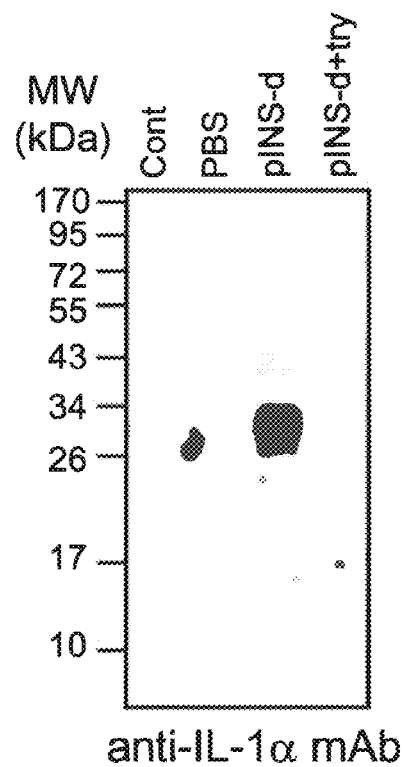
Figure 11C:
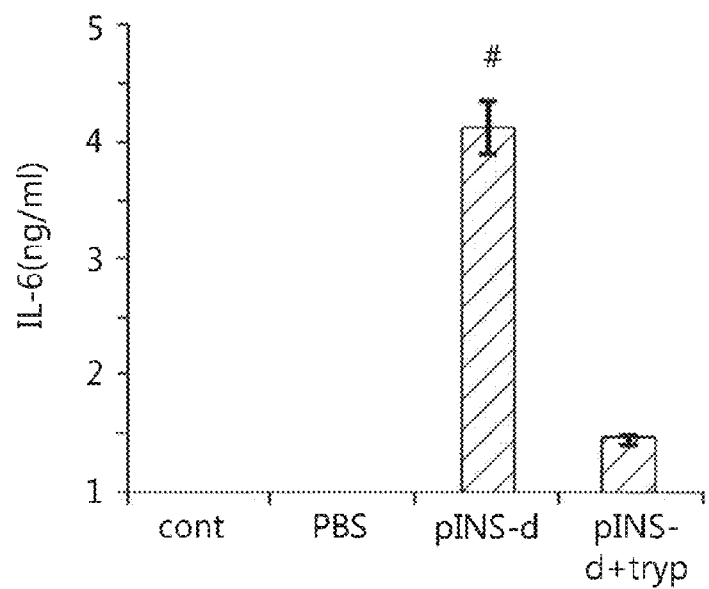

Prior to transfection of pCAGGs/Neo-human IL-1R1 into parent Wish cells, the inventors of the present disclosure examined the expression of IL-1R1 with RT-PCR, western blot, and FACS analysis as shown in FIG. 10A. Wish cells ($5\times10^5$) in a 6-well plate were transfected with empty pCAGGs or /Neo-human IL-1R1 plasmid DNA (2 mg) by using Lipofectamine® 2000 from Life Technologies. The next day, the inventors of the present disclosure transferred the transfectants into a large cell culture plate (9 cm$^2$) for Neomycine (0.2 mg/ml, Life Technologies) selection. After 10 days, an individual colony was picked up with trypsin-wet (50 mm round) Whatman 3MM paper (Sigma-Aldrich, St Louis, Mo.) and transferred into a 24-well plate. A positive clone of Wish IL-1R1 was first screened with RT-PCR and then further confirmed with western blot and FACS analysis (FIG. 2 and FIG. 10). The selected positive clones were frozen until use for assays.

Example 5: Western and Dot Blot

Wish IL-1R1/C-3 and mock clone were cultured in a 6-well plate then harvested for western blots. Cell lysate was obtained by directly adding lysis buffer (Cell Signaling, Danvers, Mass.) to the plate after removing the cell culture medium with PBS washing. For the A549 cell supernatant of the pINS-d treated cell, standalone pINS-d (100 ng/ml) or pINS-d preincubated with trypsin (20 ng/ml, Sigma-Aldrich) was treated as indicated times without FBS. The supernatant was harvested for western blotting. The cell lysate (100 mg) or the supernatant (60 ml) was mixed with loading buffer, boiled for 10 min and loaded onto 10% SDS-PAGE gels. Proteins were separated by electrophoresis and blotted onto a nitrocellulose membrane (Whatman, Piscataway, N.J.). The membrane was blocked with 5% nonfat dry milk (in 0.1% Tween-20/PBS (PBST)). For the dot-blot, recombinant proteins were dropped on a nitrocellulose membrane and the amount was defined on each blot. The primary antibodies (1 mg/ml of the rabbit polyclonal anti-IL-1α, mAb anti-IL-1α, or mAb anti-pINS-d) were incubated at 4° C. overnight. After washing, the membranes were incubated in horseradish peroxidase (HRP)-coupled respected anti-IgG (Jackson Immuno Research Laboratories, West Grove, Pa.) and then Supex (Neuronex, Seoul Korea) and an LAS-4000 imaging device (Fujifilm, Japan) were used to develop the blot.

Example 6: Monoclonal and Polyclonal Antibody Development

The inventors of the present disclosure independently developed two monoclonal antibodies against pINS-d and IL-1α protein. The anti-IL-1α and pINS-d antibody producing B cells were generated by immunizing BALB/c mice four times with 50 ml of recombinant protein (10 mg) and an equal volume of adjuvant (Gerbu, Gaiberg, Germany). The titration of immunized mice sera was confirmed by using direct ELISA with each antigen. The splenocytes of immunized mice were fused with FO cells as described in Lee, S. et al., Hybridoma (Larchmt) 29 (6), 501-509 (2010). The immunoglobulin isotypes of the selected mAb clones were determined using an Immuno-Type™ mouse mAb isotyping kit (BD Bioscience, San Jose, Calif.) according to the manufacturer's instructions. Both anti-IL-1α and pINS-d mAb were $IgG_1$ heavy chain and kappa light chain (not shown). The mAbs were purified using protein G agarose (KPL, Gaithersburg, Md.) and their purity was confirmed using Coomassie blue stained SDS-PAGE gels (not shown). The mAbs were aliquot and stored at −80° C. until use.

Example 7: IL-1α ELISA Kit

The inventors of the present disclosure obtained single anti-IL-1α mAbs (not shown) and developed an IL-1α sandwich ELISA by using the anti-IL-1α mAb (1 mg/ml) as a capture antibody and affinity purified rabbit anti-IL-1α polyclonal antibody (0.1 mg/ml) as a detection antibody. After washing, the wells were incubated with HRP-conjugated goat anti-rabbit IgG (Jackson Immuno Research Laboratories) for 1 hour and then developed with 3, 3', 5, 5'-Tetramethyl-benzidine liquid substrate (Sigma-Aldrich). The development was terminated by adding 100 ml of $H_2SO_4$ (1 M). The absorbance at 450 nm was measured by using an ELISA plate reader (Molecular Devices, Sunnyvale, Calif.).

Example 8: Cell and Assay

A549, HUVEC, Wish, and THP-1 cell lines were obtained from American Type Culture Collection (ATCC) and maintained according to the instructions provided. Primary human/mouse WBC (1:4 dilution with RPMI), PBMC, PMN, and BM cells ($5\times10^5$ per well in 96-well plate) were isolated and treated with various stimuli with concentration as defined in each figure. Human PBMC was isolated by density centrifugation of blood over Ficoll-Paque™ PLUS (GE healthcare Life Sciences, Piscataway, N.J.). PBMCs were washed twice with saline (0.9% sodium chloride) and resuspended in a culture medium (RPMI 1640). The cells were washed twice with the same culture medium and resuspended in the same medium. The cell culture supernatant was harvested at different times for cytokine assay. Human cytokines (IL-6, IL-1α, IL-1β, and TNFα) and mouse cytokines (IL-6, IL-1α, IL-1β, and TNFα) were measured with ELISA kits (R&D systems) according to manufacturer's instructions. The data are expressed as means±SEM. Statistical significance of differences was analyzed by unpaired, two-tailed Student's t test. Values of $p<0.05$ were considered statistically significant.

Example 9: Mice Experiment

Male and female 6-week-old C57BL/6 mice were obtained from Orient Biology (Kyeonggi-do, Korea). IL-1R1 deficient mice were obtained from Jackson Immuno Research Laboratories. The animal experiments were approved by the Institutional Animal Care and Use Committee (IACUC) at Konkuk University. Each stimulus was administered to the mice intraperitoneally. Two hours after injection, the cytokine levels in serum were measured with ELISA kit (R&D Systems).

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method of promoting immune activity in a patient, comprising administering a protein selected from the group consisting of a dimeric proinsulin and a dimeric proinsulin mutant with C-peptide partially deleted to the patient in need thereof, wherein the dimeric proinsulin mutant with C-peptide partially deleted is a dimer of a peptide comprising the amino acid sequence of SEQ ID NO: 2.

2. The method of claim 1, wherein the protein induces pro-inflammatory cytokines.

3. The method of claim 2, wherein the pro-inflammatory cytokine is a cytokine selected from the group consisting of interleukin (IL)-6, IL-1β, IL-2, IL-10, IL-22, interferon γ, and INFα.

4. A method of promoting immune activity in a patient, comprising administering a dimeric proinsulin mutant with C-peptide partially deleted to the patient in need thereof, wherein the dimeric proinsulin mutant with C-peptide partially deleted is a dimer of a peptide comprising the amino acid sequence of SEQ ID NO: 2.

5. The method of claim 4, wherein the protein induces pro-inflammatory cytokines.

6. The method of claim 5, wherein the pro-inflammatory cytokine is a cytokine selected from the group consisting of interleukin (IL)-6, IL-1β, IL-2, IL-10, IL-22, interferon γ, and TNFα.

* * * * *